(12) United States Patent
O'Donnell et al.

(10) Patent No.: US 7,557,184 B2
(45) Date of Patent: Jul. 7, 2009

(54) **ISOLATED *STAPHYLOCOCCUS* DNAX SUBUNIT AND USE THEREOF**

(75) Inventors: Michael E. O'Donnell, Hastings-on-Hudson, NY (US); Dan Zhang, Great Neck, NY (US); Richard Whipple, Newton, MA (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 10/282,287

(22) Filed: Oct. 28, 2002

(65) Prior Publication Data

US 2003/0129633 A1    Jul. 10, 2003

Related U.S. Application Data

(63) Continuation of application No. 09/235,245, filed on Jan. 22, 1999, now abandoned.

(60) Provisional application No. 60/074,522, filed on Jan. 27, 1998, provisional application No. 60/093,727, filed on Jul. 22, 1998.

(51) Int. Cl.
C07K 1/00    (2006.01)
(52) U.S. Cl. .................................................... 530/350
(58) Field of Classification Search ................... 530/350
See application file for complete search history.

(56) References Cited

U.S. PATENT DOCUMENTS

| | | | |
|---|---|---|---|
| 5,151,350 A | 9/1992 | Colbert et al. | |
| 5,376,526 A | 12/1994 | Brown et al. | |
| 5,459,039 A | 10/1995 | Modrich et al. | |
| 5,556,750 A | 9/1996 | Modrich et al. | |
| 5,571,676 A | 11/1996 | Shuber | |
| 5,583,026 A | 12/1996 | O'Donnell | |
| 5,587,288 A * | 12/1996 | Cheung et al. | 435/6 |
| 5,635,349 A | 6/1997 | LaMarco et al. | |
| 5,679,522 A | 10/1997 | Modrich et al. | |
| 5,683,877 A | 11/1997 | Lu-Chang et al. | |
| 5,912,143 A | 6/1999 | Bandman et al. | |
| 6,077,664 A | 6/2000 | Slater et al. | |
| 6,083,924 A | 7/2000 | Earnshaw et al. | |
| 6,100,030 A | 8/2000 | McCasky Feazel et al. | |
| 6,156,502 A | 12/2000 | Beattie | |
| 6,420,161 B1 | 7/2002 | Earnshaw et al. | |
| 6,699,703 B1 | 3/2004 | Doucette-Stamm et al. | |

FOREIGN PATENT DOCUMENTS

| | | |
|---|---|---|
| EP | 0 786 519 | 7/1997 |
| WO | WO 96/06614 | 3/1996 |
| WO | WO 96/06614 A1 | 3/1996 |
| WO | WO 98/42845 A1 | 10/1998 |
| WO | WO 99/13060 A1 | 3/1999 |
| WO | WO 99/37661 A1 | 7/1999 |

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3):1247-1252, 1988.*
BIO Critical Synergy: The Biotechnology Industry and Intellectual Property Protection, Biotechnology Industry Organization, Presentations Oct. 17, 1994, p. 74-95.*
NCBI database Entrez Protein Database Accession No. Q9Y5S5, Serine/threonine-protein kinase MRCK beta.*
NCBI database Entrez Protein Database Accession No. CAC09993 ATP dependent Clp protease ATP binding subunit.*
Fraser et al., "The Minimal Gene Complement of *Mycoplasma genitulium,*" *Science*, 270:397-403 (1995).
Sauer et al., "Sporulation and Primary Sigma Factor Homologous Genes in *Clostridium acetobutylicum,*" *J. Bacteriol.*, 176(21):6572-6582 (1994).
Kunst et al., "The Complete Genome Sequence of the Gram-Positive Bacterium *Bacillus subtilis,*" *Nature*, 390:249-256 (1997).
Yurieva et al., *J. Biol. Chem.* 272(43):27131-27139 (1997).
U.S. Appl. No. 09/235,245, O'Donnell.
U.S. Appl. No. 10/048,071, O'Donnell.
U.S. Appl. No. 12/146,353, O'Donnell.
Bodnar et al., "Use of In-house Studies of Molecular Epidemiology and Full Species Identification for Controlling Spread of Vancomycin-resistant *Enterococcus faecalis* Isolates," *J. Clin. Microbiol.* 34(9):2129-32 (1996).
Cheng et al., "The com Locus Controls Genetic Transformation in *Streptococcus pneumoniae,*" *Mol. Microbiol.* 23(4):683-92 (1997).
Cullmann et al., "Characterization of the Five Replication Factor C Genes of *Saccharomyces cerevisiae,*" *Mol. Cell. Biol.* 15(9):4661-71 (1995).
GenBank Accession No. AF000658.
GenBank Accession No. AL009126.
GenBank Accession No. AP003130.
GenBank Accession No. AP003359.
GenBank Accession No. BAB41666.
GenBank Accession No. BAB56640.
GenBank Accession No. P28630.
GenBank Accession No. P43747.
GenBank Accession No. Z99104.
Guenther et al., "Crystal Structure of the β' Subunit of the Clamploader Complex of *E. coli* DNA Polymerase III," *Cell* 91:335-45 (1997).
Guenther, "Structural Studies on the DNA Replication Apparatus: X-Ray Crystal Structure of the β' Subunit of *Escherichia coli* DNA Pol III," at 129-135 (1996) (Ph.D. thesis, Rockefeller University).

(Continued)

Primary Examiner—Patricia A Duffy
(74) Attorney, Agent, or Firm—Nixon Peabody LLP

(57) ABSTRACT

The duplex DNA of chromosomes is replicated in a multicomponent process. A helicase unwinds the DNA, a replicase synthesizes new DNA, and primase repeatedly synthesizes new primed starts on the lagging strand. The present invention is directed to the genes from Gram positive bacterium encoding these proteins, and their characterization.

1 Claim, 11 Drawing Sheets

OTHER PUBLICATIONS

Jobling & Holmes, "Analysis of Structure and Function of the B Subunit of Cholera Toxin by the Use of Site-directed Mutagenesis," *Mol. Microbiol.* 5(7):1755-67 (1991).

Larry Snyder & Wendy Champness, Molecular Genetics of Bacteria (1997).

Lee & Walker, "*Escherichia coli* DnaX Product, the τ Subunit of DNA Polymerase III, Is a Multifunctional Protein with Single-stranded DNA-dependent ATPase Activity," *Proc. Nat'l Acad. Sci. U.S.A.* 84:2713-7 (1987).

McHenry et al., "A DNA Polymerase III Holoenzyme-like Subassembly from an Extreme Thermophilic Eubacterium," *J. Mol. Biol.* 272:178-89 (1997).

Moriya et al., "Structure and Function of the Region of the Replication Origin of the *Bacillus subtilis* Chromosome. III. Nucleotide Sequence of Some 10,000 Base Pairs in the Origin Region," *Nucleic Acids Res.* 13(7):2251-65 (1985).

Morrison et al., "A Third Essential DNA Polymerase in *S. cerevisiae*," *Cell* 62:1143-51 (1990).

Pacitti et al., "Characterization and Overexpression of the Gene Encoding *Staphylococcus aureus* DNA Polymerase III," *Gene* 165:51-6 (1995).

Pestova et al., "Regulation of Competence for Genetic Transformation in *Streptococcus pneumoniae* by an Auto-induced Peptide Pheromone and a Two-component Regulatory System," *Mol. Microbiol.* 21(4):853-62 (1996).

Seville et al., "Fluorometric Assay for DNA Polymerases and Reverse Transcriptase," *BioTechniques* 21(4):664-72 (1996).

Guy P. Youmans et al., The Biological and Clinical Basis of Infectious Disease 624, 802 (1985).

Cullmann et al., "Characterization of the Five Replication Factor C Genes of *Saccharomyces cerevisiae*," *Mol. Cell. Biol.* 15(9):4661-71 (1995).

GenBank Accession No. AF000658 1997.
GenBank Accession No. AL009126 2007.
GenBank Accession No. AP003130 2003.
GenBank Accession No. AP 003359 2004.
GenBank Accession No. BAB41666 2007.
GenBank Accession No. BAB56640 2007.
GenBank Accession No. P28630 2007.
GenBank Accession No. P43747 2007.
GenBank Accession No. Z99104 2007.

Guenther et al., "Crystal Sturcture of the 8'Subunit of the Clamp-loader Complex of *E. Coli* DNA Polymerase III", *Cell* 91:335-45 (1997).

Guenther, "Structural Studies on the DNA Replication Apparatus: X-Ray Crystal Structure of the 8' Subunit of *Escherichia coli* DNA Pol III," at 129-135 (1996) (Ph.D. thesis, Rockefeller University).

Jobling & Holmes, "Analysis of Stucture and Function of the B Subunit of Cholera Toxin by the Use of Site-directed Mutagenesis," *Mol. Microbiol.* 5(7):1755-57 (1991).

Larry Snyder & Wendy Champness, Molecular Genetics of Bacteria (1997).

Lee & Walker, "*Escherichia coli* DnaX Product, the τ Subunit of DNA Polymerase III, Is a Multifunctional Protein with Single-stranded DNA-dependent ATPase Activity," *Proc. Nat'l Acad. Sci. U.S.A.* 84:2713-7 (1987).

McHenry et al., "A DNA Polymerase III Holoenzyme-like Subassembly from an Extreme Thermophilic Eubacterium," *J. Mol. Biol.* 272:178-89 (1997).

Moriya et al., "Structure and Function of the Region of the Replication Origin of the *Bacillus Subtilis* Chromosome. III. Nucleotide Sequence of Some 10,000 Base Pairs in the Origin Region," *Nucleic Acids Res.* 13(7):2251-65 (1985).

Morrison et al., "A Third Essential DNA Polymerase in *S. cerevisiae*," *Cell* 62:1143-51 (1990).

* cited by examiner

A)

— PolIII$_L$

B) Mono Q

C) Phosphocellulose

A) Induction

B) Nickel column

C) Mono Q

A) Linear DNA

B) Circular DNA

A) MonoQ

B) P-Cell

A) Agarose Gel

B) DNA Synthesis

| Addition | DNA Synthesis (pmol) PEAK | | | |
| --- | --- | --- | --- | --- |
| | Peak 1 | Peak 2 | Peak 3 | Peak 4 |
| None | 22.7 | 70.6 | 146.1 | 4.7 |
| E. coli β, γ complex | 72.9 | 61.2 | 71.4 | 25.9 |

```
S. aureus    KIWRATCIWNCDFRSSACKAVAKDVGRIMGFDEVTLNEISSLIPHKLGITLDEAYQID--D
E. coli      MYGRDAVSQIITFGTMAAKAVIRDVGRVLGHPYGFVDRISKLIPPDPGMTLAKAFEAEPQ
Sal.typ      MYGRDAVSQIITFGTMAAKAVIRDVGRVLGHPYGFVDRISKLVPPDPGMTLAKAFEAEPQ
                  *  *** *  ****  *      **  *** *    * ***

S. aureus    FKKFVHRNHRHQRWFSICKKLEGLPRHTSTHAAGIIINDHPLYEYAPLTKGDTG--LLTQ
E. coli      LPEIYEADEEVKALIDMARKLEGVTRNAGKHAGGVVIAPTKITDFAPLYCDEEGKHPVTQ
Sal.typ      LPEIYEADEEVRALIDMARKLEGVTRNAGKHAGGVVIAPTKITDFAPLYCDEEGKHPVTQ
                 *      *      ****  *  * *  *** * * *    * ***     *

S. aureus    WIMTEAERIGLLKIDFLGLRNLSIHQILTRVEKDLGFN----IDIEKIPFDDQKVFELL
E. coli      FDKSDVEYAGLVKFDFLGLRTLTIINWALEMINKRAKNGEPPLDIAAIPLDDKKSFDML
Sal.typ      FDKSDVEYAGLVKFDFLGLRTLTIINWALEMINKRRAKNGEPPLDIAAIPLDDKKSFDML
              .  *   * ** *****     *    *    *  ** **  ** *****   *  *

S. aureus    SQGDTTGIFQLESDGVRSVLKKLKPEHFEDIVAVTSLYRPGMEE----IPTYITRRHDPS-
E. coli      QRSETTAVFQLESRGMKDLIKRLQPDCFEDMIALVALFRPGPLQSGMVDNFIDRKHGREE
Sal.typ      QRSETTAVFQLESRGMKDLIKRLQPDCFEDMIALVALFRPGPLQSGMVDNFIDRKHGREE
              .   . ***** *  . ** * *  *** **.**  **** *     *   .   .

S. aureus    ----KVQYLHPLEPILKNTYGVIIYQEQIMQIASTFANFSYGEADILRRAMSKKNRAVL
E. coli      ISYPDVQWQHESLKPVLEPTYGIILYQEQVMQIAQVLSGYTLGGADMLRRAMGKKKPEEM
Sal.typ      LSYPDVQWQHESLKPVLEPTYGIILYQEQVMQIAQVLSGYTLGGADMLRRAMGKKKPEEM
                  *      * * *** ***  ****  ****       *  ***  ***

S. aureus    ERDAQHFIEGTKQNGYHEDISKQIFDLI-------------
E. coli      AKQRSVFAEGAEKNGINAELAMKIFDLVEKFAGYGFNKSHSAAYALVSYQTLWLKAHYPA
Sal.typ      AKQRSVFEEGAKKNGIDGELAMKIFDLVEKFAGYGFNKSHSAAYALVSYQTLWLKAHYPA
              *   *   *  .**    .  ****
```

```
                                                                    ATP site
S.aureus  MKGYCLWRCNLDYQALFVVPTP-KFEDVVGQEHSEDCAMG------SHAYLFSGPRGTGKT
B.sub.    ---------MSYQALYRVFRPQRFEDVVGQEHITKTLQNALLQKKFSHAYLFSGPRGTGKT
E.coli    --------MSYQVLARKWRPQTFADVVGQEHVLTALANGLSLGRIHHAYLFSGTRGVGKT
                   *  *  *    * ********  ****** ** ***

Zn++ finger
                                 |      | |
S.aureus  IAKVFAKAINCLNSTDGEPCNECHICKGITQGTNSDVIEIDAASNNGVDEIRNIRDKVTKYA
B.sub     SAAKIFAKAVNCEHAPVDEPCNECAACKGITNGSISDVIEIDAASNNGVDEIRDIRDKVKFA
E.coli    SIARLLAKGLNCETGITATPCGVCDNCREIEQGRFVDLIEIDAASRTKVEDTRDLLDNVQYA
            *  **    **  *   ** *      *    ********* *   * **   *  *

S.aureusPSESKYKVYIIDEVHMLTTGAFNALLKTLEEPPAHAIFILATTEPHKIPPTIISRA
B.sub    PSAVTYKVYIIDEVHMLSIGAFNALLKTLEEPPEHCIFILATTEPHKIPLTIISRC
E.coli   PARGRFKVYLIDEVHMLSRHSFNALLKTLEEPPEHVKFLLATTDPQKLPVTILSRC
           *  ***:*********   *********** *  :****:* :*:* **:**
```

FIGURE 10

```
S.aureus  ALNIANKIERMKIYLAVGIFSLEMGADQLTRMICSSGNVDSNRLRTGTMTEEDWSRFTI
B.sub     ALNIAQNVA-TKTDFSVAIFSLFMGAEQLVMRMLCAEGNINAQNLRTGNLTEEDWGKLTM
E.coli    AMNLVENAA-MLQDKPVLIFSLEMPSEQIMRSLASLSRVDQTKIRTGQLDDEDWARISG
Sal.typ   AMNLCENAA-MLQDKPVLIFSLEMPGEQIMRMLASLSRVDQTRIRTGQLDDEDWARISG
          *.*.                 .  *     .     .  *    ***     .

S.aureus  AVGKLS-RTKIFIDDTPGIPINDLRSKCRRLKQEHG-LYVIVIDYLQLIPGVGSRASDNR
B.sub     AMGSLS-NSGIYIDDIPGIRVSEIRAKCRRLKQESG-LGMILIDYLQLIQGSG-RSKDNR
E.coli    TMGILLEKRNIYIDDSSGLTPTEVRSRARRIAREHGGIGLIMIDYLQLMRVPA---LSDNR
Sal.typ   TMGILLEKRNMYIDDSSGLTPTEVRSRARRIFREHGGLSLIMIDYLQLMRVPS---LSDNR
           * *       ***  *     .   **     * .   ******         ***

S.aureus  QQEVSEISRTLKALARELECPVIADSQLSPALPPRATRPDLPRH------------
B.sub     QQEVSEISRELKSIARELQVPVIALSQLSRGVEQRQDKRPMMSDIRESGSIEQDADIVAF
E.coli    TLEIAEISRSLKALAKELNVPVVALSQLNRSLEQRADKRPVNSDLRESGSIEQDADLIMF
Sal.typ   TLEIAEISRSLKALAKELQVPVVALSQLNRSLEQRADKRPVNSDLRESGSIEQDADLIMF
          *..****.**..**    **   * ***    *              **
```

FIGURE 11

SEQUENCE LISTING

<160> NUMBER OF SEQ ID NOS: 44

<210> SEQ ID NO 1
<211> LENGTH: 1726
<212> TYPE: DNA
<213> ORGANISM: Staphylococcus aureus

<400> SEQUENCE: 1

```
gatatagata tggactggga agatacacgc cgagaaaagg tcattcagta cgtccaagaa      60
aaatatggcg agctacatgt atctggaatt gtgactttcg gtcatctgct tgcaaaagcg     120
gttgctaaag atgttggacg aattatgggg tttgatgaag ttacattaaa tgaaatttca     180
agtttaatcc cacataaatt aggaattaca cttgatgaag catatcaaat tgacgatttt     240
aaaaagtttg tacatcgaaa ccatcgacat caacgctggt tcagtatttg taaaaagtta     300
gaaggtttac caagacatac atctacacat gcggcaggaa ttattattaa tgaccatcca     360
ttatatgaat atgcccsttt aacgaaaggg gatacaggat tattaacgca atggacaatg     420
actgaagccg aacgtattgg tttattaaaa atagattttc tagggttacg aaatttatca     480
attatccatc aaattttgac tcgagtcgaa aaagatttag gttttaatat tgatattgaa     540
aaaattccat ttgatgatca aaaagtgttt gaattgttgt cgcaaggaga tacgactggc     600
atatttcaat tagagtctga cggtgttaga agtgtattaa aaaaattaaa gccggaacac     660
tttgaggata ttgttgctgt aacttctttg tatagaccag gtccaatgga agaaattcca     720
acttacatta caagaagaca tgatccaagc aaagttcaat atttacatcc ccatttagaa     780
cctatattaa aaaatactta cggtgttatt atttatcaag aacaaattat gcaaatagcg     840 agcactttg caaacttcag ttatggtgaa gcggatattt taagaagagc aatgagtaaa     900
aaaaatagag ctgttcttga aagagacgct caacatttta tagaaggtac aaagcaaaat     960
ggttatcacg aagacttagt aagtaagcag atatttgatt tgattctgaa atttgctgat    1020
```

```
gatggatttc ctagagcaca tgctgtcagc tattctaaaa ttgcatacat tatgagcttt   1080
ttaaaagtcc attatccaaa ttattttac gcaaatattt taagtaatgt tattggaagt    1140
gagaagaaaa ctgctcaaat gatagaagaa gcaaaaaaac aaggtatcac tatattgcca   1200
ccgaacatta acgaaagtca ttggttttat aaaccttccc aagaaggcat ttatttatca   1260
attggtacaa ttaaaggtgt aggttatcaa agtgtgaaag tgattgttga agaacgtttt   1320
cagaacggca aatttaaaga tttctttgat tctgctagac gtataccgaa gagagtcaaa   1380
acgagaaagt tacttgaagc attgatttta gtgggagcgt tgatgctttt ggtaaaaca    1440 cgttcaacgt tgttgcaagc tattgatcaa gtgttggatg gtgatttaaa cattgaacaa   1500
gatggttttt tatttgatat tttaacgcca aaacagatgt atgaagataa agaagaattg   1560
cctgatgcac ttattagtca gtatgaaaaa gaatatttag gattttatgt ttcgcaacac   1620
ccagtagata agaagtttgt tgccaaacaa tatttaacga tattttcttg cgaaaacgtt   1680
gctaaagatg ttcgacgaat tatggggttt gatgaagtta aacaaa                 1726
```

<210> SEQ ID NO 2
<211> LENGTH: 573
<212> TYPE: PRT
<213> ORGANISM: Staphylococcus aureus

<400> SEQUENCE: 2

```
Asp Ile Asp Met Asp Trp Glu Asp Thr Arg Arg Glu Lys Val Ile Gln
 1               5                  10                  15

Tyr Val Gln Glu Lys Tyr Gly Glu Leu His Val Ser Gly Ile Val Thr
            20                  25                  30

Phe Gly His Leu Leu Ala Lys Ala Val Ala Lys Asp Val Gly Arg Ile
        35                  40                  45

Met Gly Phe Asp Glu Val Thr Leu Asn Glu Ile Ser Ser Leu Ile Pro
    50                  55                  60

His Lys Leu Gly Ile Thr Leu Asp Glu Ala Tyr Gln Ile Asp Asp Phe
65                  70                  75                  80

Lys Lys Phe Val His Arg Asn His Arg His Gln Arg Trp Phe Ser Ile
                85                  90                  95

Cys Lys Lys Leu Glu Gly Leu Pro Arg His Thr Ser Thr His Ala Ala
            100                 105                 110

Gly Ile Ile Ile Asn Asp His Pro Leu Tyr Glu Tyr Ala Pro Leu Thr
        115                 120                 125

Lys Gly Asp Thr Gly Leu Leu Thr Gln Trp Thr Met Thr Glu Ala Glu
    130                 135                 140

Arg Ile Gly Leu Leu Lys Ile Asp Phe Leu Gly Leu Arg Asn Leu Ser
145                 150                 155                 160

Ile Ile His Gln Ile Leu Thr Arg Val Glu Lys Asp Leu Gly Phe Asn
                165                 170                 175

Ile Asp Ile Glu Lys Ile Pro Phe Asp Asp Gln Lys Val Phe Glu Leu
            180                 185                 190

Leu Ser Gln Gly Asp Thr Thr Gly Ile Phe Gln Leu Glu Ser Asp Gly
        195                 200                 205

Val Arg Ser Val Leu Lys Lys Leu Lys Pro Glu His Phe Glu Asp Ile
    210                 215                 220

Val Ala Val Thr Ser Leu Tyr Arg Pro Gly Pro Met Glu Glu Ile Pro
225                 230                 235                 240

Thr Tyr Ile Thr Arg Arg His Asp Pro Ser Lys Val Gln Tyr Leu His
```

```
                245                 250                 255
Pro His Leu Glu Pro Ile Leu Lys Asn Thr Tyr Gly Val Ile Ile Tyr
            260                 265                 270
Gln Glu Gln Ile Met Gln Ile Ala Ser Thr Phe Ala Asn Phe Ser Tyr
        275                 280                 285
Gly Glu Ala Asp Ile Leu Arg Arg Ala Met Ser Lys Lys Asn Arg Ala
    290                 295                 300
Val Leu Glu Arg Asp Ala Gln His Phe Ile Glu Gly Thr Lys Gln Asn
305                 310                 315                 320
Gly Tyr His Glu Asp Ile Ser Lys Gln Ile Phe Asp Leu Ile Leu Lys
                325                 330                 335
Phe Ala Asp Gly Phe Pro Arg Ala His Ala Val Ser Tyr Ser Lys Ile
            340                 345                 350
Ala Tyr Ile Met Ser Phe Leu Lys Val His Tyr Pro Asn Tyr Phe Tyr
        355                 360                 365
Ala Asn Ile Leu Ser Asn Val Ile Gly Ser Glu Lys Lys Thr Ala Gln
    370                 375                 380
Met Ile Glu Glu Ala Lys Lys Gln Gly Ile Thr Ile Leu Pro Pro Asn
385                 390                 395                 400
Ile Asn Glu Ser His Trp Phe Tyr Lys Pro Ser Gln Glu Gly Ile Tyr
                405                 410                 415
Leu Ser Ile Gly Thr Ile Lys Gly Val Gly Tyr Gln Ser Val Lys Val
            420                 425                 430
Ile Val Glu Glu Arg Phe Gln Asn Gly Lys Phe Lys Asp Phe Phe Asp
        435                 440                 445
Ser Ala Arg Arg Ile Pro Lys Arg Val Lys Thr Arg Lys Leu Leu Glu
    450                 455                 460
Ala Leu Ile Leu Val Gly Ala Phe Asp Ala Phe Gly Lys Thr Arg Ser
465                 470                 475                 480
Thr Leu Leu Gln Ala Ile Asp Gln Val Leu Asp Gly Asp Leu Asn Ile
                485                 490                 495
Glu Gln Asp Gly Phe Leu Phe Asp Ile Leu Thr Pro Lys Gln Met Tyr
            500                 505                 510
Glu Asp Lys Glu Glu Leu Pro Asp Ala Leu Ile Ser Gln Tyr Glu Lys
        515                 520                 525
Glu Tyr Leu Gly Phe Tyr Val Ser Gln His Pro Val Asp Lys Lys Phe
    530                 535                 540
Val Ala Lys Gln Tyr Leu Thr Ile Phe Ser Cys Glu Asn Val Ala Lys
545                 550                 555                 560
Asp Val Arg Arg Ile Met Gly Phe Asp Glu Val Lys Gln
                565                 570
```

<210> SEQ ID NO 3
<211> LENGTH: 1698
<212> TYPE: DNA
<213> ORGANISM: Staphylococcus aureus

<400> SEQUENCE: 3
ttgaattatc aagccttata tcgtatgtac agaccccaaa gtttcgagga tgtcgtcgga     60
caagaacatg tcacgaagac attgcgcaat gcgatttcga agaaaaaaca gtcgcatgca    120 tatatttta gtggtccgag aggtacgggg aaaacgagta ttgccaaagt gtttgctaaa    180
gcaatcaact gtttaaatag cactgatgga gaaccttgta tgaatgtca tatttgtaaa    240 ggcattacgc aggggactaa ttcagatgtg atagaaattg atgctgctag taataatggc    300

```
gttgatgaaa taagaaatat tagagacaaa gttaaatatg caccaagtga atcgaaatat    360
aaagtttata ttatagatga ggtgcacatg ctaacaacag gtgcttttaa tgccctttta    420
aagacgttag aagaacctcc agcacacgct atttttatat tggcaacgac agaaccacat    480
aaaatccctc caacaatcat ttctagggca caacgttttg attttaaagc aattagccta    540
gatcaaattg ttgaacgttt aaaatttgta gcagatgcac aacaaattga atgtgaagat    600
gaagccttgg catttatcgc taaagcgtct gaaggggta tgcgtgatgc attaagtatt     660
atggatcagg ctattgcttt cggcgatggc acattgacat acaagatgc cctaaatgtt     720 acgggtagcg ttcatgatga agcgttggat cacttgtttg atgatattgt acaaggtgac    780
gtacaagcat cttttaaaaa ataccatcag tttataacag aaggtaaaga agtgaatcgc    840
ctaataaatg atatgattta ttttgtcaga gatacgatta tgaataaaac atctgagaaa    900
gatactgagt atcgagcact gatgaactta gaattagata tgttatatca atgattgat    960 cttattaatg atacattagt gtcgattcgt tttagtgtga atcaaaacgt tcattttgaa    1020
gtattgttag taaaattagc tgagcagatt aagggtcaac cacaagtgat tgcgaatgta    1080
gctgaaccag cacaaattgc ttcatcgcca aacacagatg tattgttgca acgtatggaa    1140
cagttagagc aagaactaaa aacactaaaa gcacaaggag tgagtgttgc tcctactcaa    1200
aaatcttcga aaaagcctgc gagaggtata caaaaatcta aaaatgcatt tcaatgcaa    1260 caaattgcaa aagtgctaga taaagcgaat aaggcagata tcaaattgtt gaaagatcat    1320
tggcaagaag tgattgacca tgcccaaaac aatgataaaa aatcactcgt tagtttattg    1380
caaaattcgg aacctgtggc ggcaagtgaa gatcacgtcc ttgtgaaatt tgaggaagag    1440
atccattgtg aaatcgtcaa taaagacgac gagaaacgta gtagtataga aagtgttgta    1500
tgtaatatcg ttaataaaaa cgttaaagtt gttggtgtac catcagatca atggcaaaga    1560
gttcgaacgg agtatttaca aaatcgtaaa acgaaggcg atgatatgcc aaagcaacaa    1620
gcacaacaaa cagatattgc tcaaaaagca aaagatcttt tcggtgaaga aactgtacat    1680
gtgatagatg aagagtga                                                  1698

<210> SEQ ID NO 4
<211> LENGTH: 566
<212> TYPE: PRT
<213> ORGANISM: Staphylococcus aureus

<400> SEQUENCE: 4

Leu Asn Tyr Gln Ala Leu Tyr Arg Met Tyr Arg Pro Gln Ser Phe Glu
 1               5                  10                  15

Asp Val Val Gly Gln Glu His Val Thr Lys Thr Leu Arg Asn Ala Ile
            20                  25                  30

Ser Lys Glu Lys Gln Ser His Ala Tyr Ile Phe Ser Gly Pro Arg Gly
        35                  40                  45

Thr Gly Lys Thr Ser Ile Ala Lys Val Phe Ala Lys Ala Ile Asn Cys
    50                  55                  60

Leu Asn Ser Thr Asp Gly Glu Pro Cys Asn Glu Cys His Ile Cys Lys
65                  70                  75                  80

Gly Ile Thr Gln Gly Thr Asn Ser Asp Val Ile Glu Ile Asp Ala Ala
                85                  90                  95

Ser Asn Asn Gly Val Asp Glu Ile Arg Asn Ile Arg Asp Lys Val Lys
            100                 105                 110

Tyr Ala Pro Ser Glu Ser Lys Tyr Lys Val Tyr Ile Ile Asp Glu Val
```

-continued

```
            115                 120                 125
His Met Leu Thr Thr Gly Ala Phe Asn Ala Leu Leu Lys Thr Leu Glu
        130                 135                 140

Glu Pro Pro Ala His Ala Ile Phe Ile Leu Ala Thr Thr Glu Pro His
145                 150                 155                 160

Lys Ile Pro Pro Thr Ile Ile Ser Arg Ala Gln Arg Phe Asp Phe Lys
                165                 170                 175

Ala Ile Ser Leu Asp Gln Ile Val Glu Arg Leu Lys Phe Val Ala Asp
            180                 185                 190

Ala Gln Gln Ile Glu Cys Glu Asp Ala Leu Ala Phe Ile Ala Lys
        195                 200                 205

Ala Ser Glu Gly Gly Met Arg Asp Ala Leu Ser Ile Met Asp Gln Ala
210                 215                 220

Ile Ala Phe Gly Asp Gly Thr Leu Thr Leu Gln Asp Ala Leu Asn Val
225                 230                 235                 240

Thr Gly Ser Val His Asp Glu Ala Leu Asp His Leu Phe Asp Asp Ile
                245                 250                 255

Val Gln Gly Asp Val Gln Ala Ser Phe Lys Lys Tyr His Gln Phe Ile
            260                 265                 270

Thr Glu Gly Lys Glu Val Asn Arg Leu Ile Asn Asp Met Ile Tyr Phe
        275                 280                 285

Val Arg Asp Thr Ile Met Asn Lys Thr Ser Glu Lys Asp Thr Glu Tyr
    290                 295                 300

Arg Ala Leu Met Asn Leu Glu Leu Asp Met Leu Tyr Gln Met Ile Asp
305                 310                 315                 320

Leu Ile Asn Asp Thr Leu Val Ser Ile Arg Phe Ser Val Asn Gln Asn
                325                 330                 335

Val His Phe Glu Val Leu Leu Val Lys Leu Ala Glu Gln Ile Lys Gly
            340                 345                 350

Gln Pro Gln Val Ile Ala Asn Val Ala Glu Pro Ala Gln Ile Ala Ser
        355                 360                 365

Ser Pro Asn Thr Asp Val Leu Leu Gln Arg Met Glu Gln Leu Glu Gln
370                 375                 380

Glu Leu Lys Thr Leu Lys Ala Gln Gly Val Ser Val Ala Pro Thr Gln
385                 390                 395                 400

Lys Ser Ser Lys Lys Pro Ala Arg Gly Ile Gln Lys Ser Lys Asn Ala
                405                 410                 415

Phe Ser Met Gln Gln Ile Ala Lys Val Leu Asp Lys Ala Asn Lys Ala
            420                 425                 430

Asp Ile Lys Leu Leu Lys Asp His Trp Gln Glu Val Ile Asp His Ala
        435                 440                 445

Gln Asn Asn Asp Lys Lys Ser Leu Val Ser Leu Leu Gln Asn Ser Glu
450                 455                 460

Pro Val Ala Ala Ser Glu Asp His Val Leu Val Lys Phe Glu Glu Glu
465                 470                 475                 480

Ile His Cys Glu Ile Val Asn Lys Asp Glu Lys Arg Ser Ser Ile
                485                 490                 495

Glu Ser Val Val Cys Asn Ile Val Asn Lys Asn Val Lys Val Gly
            500                 505                 510

Val Pro Ser Asp Gln Trp Gln Arg Val Arg Thr Glu Tyr Leu Gln Asn
        515                 520                 525

Arg Lys Asn Glu Gly Asp Asp Met Pro Lys Gln Gln Ala Gln Gln Thr
530                 535                 540
```

-continued

Asp Ile Ala Gln Lys Ala Lys Asp Leu Phe Gly Glu Glu Thr Val His
545                 550                 555                 560

Val Ile Asp Glu Glu Glx
            565

<210> SEQ ID NO 5
<211> LENGTH: 2034
<212> TYPE: DNA
<213> ORGANISM: Staphylococcus aureus

<400> SEQUENCE: 5

| | | | | | |
|---|---|---|---|---|---|
| atggatagaa | tgtatgagca | aaatcaaatg | ccgcataaca | atgaagctga | acagtctgtc | 60 |
| ttaggttcaa | ttattataga | tccagaattg | attaatacta | ctcaggaagt | tttgcttcct | 120 |
| gagtcgtttt | ataggggtgc | ccatcaacat | attttccgtg | caatgatgca | cttaaatgaa | 180 |
| gataataaag | aaattgatgt | tgtaacattg | atggatcaat | tatcgacgga | aggtacgttg | 240 |
| aatgaagcgg | gtggcccgca | atatcttgca | gagttatcta | caaatgtacc | aacgacgcga | 300 |
| aatgttcagt | attatactga | tatcgtttct | aagcatgcat | taaaacgtag | attgattcaa | 360 |
| actgcagata | gtattgccaa | tgatggatat | aatgatgaac | ttgaactaga | tgcgatttta | 420 |
| agtgatgcag | aacgtcgaat | tttagagcta | tcatcttctc | gtgaaagcga | tggctttaaa | 480 |
| gacattcgag | acgtcttagg | acaagtgtat | gaaacagctg | aagagcttga | tcaaaatagt | 540 |
| ggtcaaacac | caggtatacc | tacaggatat | cgagatttag | accaaatgac | agcagggttc | 600 |
| aaccgaaatg | atttaattat | ccttgcagcg | cgtccatctg | taggtaagac | tgcgttcgca | 660 |
| cttaatattg | cacaaaaagt | tgcaacgcat | gaagatatgt | atacagttaa | aagcaacagg | 720 |
| aagtttctga | atctctcgt | acattaaaag | cattagcccg | tgaattaaaa | tgtccagtta | 780 |
| tcgcattaag | tcagttatct | cgtggtgttg | aacaacgaca | agataaacgt | ccaatgatga | 840 |
| gtgatattcg | tgaatctggt | tcgattgagc | aagatgccga | tatcgttgca | ttcttatacc | 900 |
| gtgatgatta | ctataaccgt | ggcggcgatg | aagatgatga | cgatgatggt | ggtttcgagc | 960 |
| cacaaacgaa | tgatgaaaac | ggtgaaattg | aaattatcat | tgttaagcaa | cgtaacggtc | 1020 |
| caacaggcac | agttaagtta | cattttatga | acaatataa | taaattttag | agctatcatc | 1080 |
| ttttcgtgaa | agcgatggct | ttaaagacat | tcgagacgtc | ttaggacaag | tgtatgaaac | 1140 |
| agctgaagag | cttgatcaaa | atagtggtca | acaccaggt | ataccttacag | gatatcgaga | 1200 |
| tttagaccaa | atgacagcag | ggttcaaccg | aaatgattta | attatccttg | cagcgcgtcc | 1260 |
| atctgtaggt | aagactgcgt | tcgcacttaa | tattgcacaa | aaagttgcaa | cgcatccgca | 1320 |
| cttaatattg | ccaataagtt | ggaacgcatg | aagatatatc | tagcagttgg | tattttctca | 1380 |
| ctagagatgg | gtgctgatca | gttaaccaca | cgtatgattt | gtagttctgg | taatgttgac | 1440 |
| tcaaaccgct | taagaaccgg | tactatgact | gaggaagatt | ggagtcgttt | tactatagcg | 1500 |
| gttggtaaat | tatcacgtac | gaagattttt | attgatgata | caccgggtat | tcgaattaat | 1560 |
| gatttacgtt | ctaaatgtcg | tcgattaaag | caagaacatg | gcttagacat | gattgtgatt | 1620 |
| gactacttac | agttgattca | aggtagtggt | tcacgtgcgt | ccgataacag | acaacaggaa | 1680 |
| gtttctgaaa | tctctcgtac | attaaaagca | ttagcccgtg | aattaaaatg | tccagttatc | 1740 |
| gcattaagtc | agttatctcg | tggtgttgaa | caacgacaag | ataaacgtcc | aatgatgagt | 1800 |
| gatattcgtg | aatctggttc | gattgagcaa | gatgccgata | tcgttgcatt | cttataccgt | 1860 |
| gatgattact | ataaccgtgg | cggcgatgaa | gatgatgacg | atgatggtgg | tttcgagccc | 1920 |

-continued

```
caaacgaatg atgaaaacgg tgaaattgaa attatcattg ctaagcaacg ttacggtcca    1980
acaggcacag ttaagttact ttttatgaaa caatatggta aatttaccga tatc           2034
```

<210> SEQ ID NO 6
<211> LENGTH: 457
<212> TYPE: PRT
<213> ORGANISM: Staphylococcus aureus

<400> SEQUENCE: 6

| | | | | | | | | | | | | | | |
|---|---|---|---|---|---|---|---|---|---|---|---|---|---|---|
| Met | Asp | Arg | Met | Tyr | Glu | Gln | Asn | Gln | Met | Pro | His | Asn | Asn | Glu | Ala |
| 1 | | | | 5 | | | | | 10 | | | | | 15 | |
| Glu | Gln | Ser | Val | Leu | Gly | Ser | Ile | Ile | Ile | Asp | Pro | Glu | Leu | Ile | Asn |
| | | | 20 | | | | | 25 | | | | | 30 | | |
| Thr | Thr | Gln | Glu | Val | Leu | Leu | Pro | Glu | Ser | Phe | Tyr | Arg | Gly | Ala | His |
| | | | 35 | | | | | 40 | | | | | 45 | | |
| Gln | His | Ile | Phe | Arg | Ala | Met | Met | His | Leu | Asn | Glu | Asp | Asn | Lys | Glu |
| | | 50 | | | | | 55 | | | | | 60 | | | |
| Ile | Asp | Val | Val | Thr | Leu | Met | Asp | Gln | Leu | Ser | Thr | Glu | Gly | Thr | Leu |
| 65 | | | | | 70 | | | | | 75 | | | | | 80 |
| Asn | Glu | Ala | Gly | Gly | Pro | Gln | Tyr | Leu | Ala | Glu | Leu | Ser | Thr | Asn | Val |
| | | | | 85 | | | | | 90 | | | | | 95 | |
| Pro | Thr | Thr | Arg | Asn | Val | Gln | Tyr | Tyr | Thr | Asp | Ile | Val | Ser | Lys | His |
| | | | 100 | | | | | 105 | | | | | 110 | | |
| Ala | Leu | Lys | Arg | Arg | Leu | Ile | Gln | Thr | Ala | Asp | Ser | Ile | Ala | Asn | Asp |
| | | | 115 | | | | | 120 | | | | | 125 | | |
| Gly | Tyr | Asn | Asp | Glu | Leu | Glu | Leu | Asp | Ala | Ile | Leu | Ser | Asp | Ala | Glu |
| | | 130 | | | | | 135 | | | | | 140 | | | |
| Arg | Arg | Ile | Leu | Glu | Leu | Ser | Ser | Ser | Arg | Glu | Ser | Asp | Gly | Phe | Lys |
| 145 | | | | | 150 | | | | | 155 | | | | | 160 |
| Asp | Ile | Arg | Asp | Val | Leu | Gly | Gln | Val | Tyr | Glu | Thr | Ala | Glu | Glu | Leu |
| | | | | 165 | | | | | 170 | | | | | 175 | |
| Asp | Gln | Asn | Ser | Gly | Gln | Thr | Pro | Gly | Ile | Pro | Thr | Gly | Tyr | Arg | Asp |
| | | | 180 | | | | | 185 | | | | | 190 | | |
| Leu | Asp | Gln | Met | Thr | Ala | Gly | Phe | Asn | Arg | Asn | Asp | Leu | Ile | Ile | Leu |
| | | | 195 | | | | | 200 | | | | | 205 | | |
| Ala | Ala | Arg | Pro | Ser | Val | Gly | Lys | Thr | Ala | Phe | Ala | Leu | Asn | Ile | Ala |
| | | 210 | | | | | 215 | | | | | 220 | | | |
| Gln | Lys | Leu | Glu | Arg | Met | Lys | Ile | Tyr | Leu | Ala | Val | Gly | Ile | Phe | Ser |
| 225 | | | | | 230 | | | | | 235 | | | | | 240 |
| Leu | Glu | Met | Gly | Ala | Asp | Gln | Leu | Thr | Thr | Arg | Met | Ile | Cys | Ser | Ser |
| | | | | 245 | | | | | 250 | | | | | 255 | |
| Gly | Asn | Val | Asp | Ser | Asn | Arg | Leu | Arg | Thr | Gly | Thr | Met | Thr | Glu | Glu |
| | | | 260 | | | | | 265 | | | | | 270 | | |
| Asp | Trp | Ser | Arg | Phe | Thr | Ile | Ala | Val | Gly | Lys | Leu | Ser | Arg | Thr | Lys |
| | | | 275 | | | | | 280 | | | | | 285 | | |
| Ile | Phe | Ile | Asp | Asp | Thr | Pro | Gly | Ile | Arg | Ile | Asn | Asp | Leu | Arg | Ser |
| | | 290 | | | | | 295 | | | | | 300 | | | |
| Lys | Cys | Arg | Arg | Leu | Lys | Glu | His | Gly | Leu | Asp | Met | Ile | Val | Ile |
| 305 | | | | | 310 | | | | | 315 | | | | | 320 |
| Asp | Tyr | Leu | Gln | Leu | Ile | Gln | Gly | Ser | Gly | Ser | Arg | Ala | Ser | Asp | Asn |
| | | | | 325 | | | | | 330 | | | | | 335 | |
| Arg | Gln | Gln | Glu | Val | Ser | Glu | Ile | Ser | Arg | Thr | Leu | Lys | Ala | Leu | Ala |
| | | | 340 | | | | | 345 | | | | | 350 | | |
| Arg | Glu | Leu | Lys | Cys | Pro | Val | Ile | Ala | Leu | Ser | Gln | Leu | Ser | Arg | Gly |

```
                 355                 360                 365
Val Glu Gln Arg Gln Asp Lys Arg Pro Met Met Ser Asp Ile Arg Glu
    370                 375                 380

Ser Gly Ser Ile Glu Gln Asp Ala Asp Ile Val Ala Phe Leu Tyr Arg
385                 390                 395                 400

Asp Asp Tyr Tyr Asn Arg Gly Gly Asp Glu Asp Asp Asp Asp Asp Gly
                405                 410                 415

Gly Phe Glu Pro Gln Thr Asn Asp Glu Asn Gly Glu Ile Glu Ile Ile
            420                 425                 430

Ile Ala Lys Gln Arg Tyr Gly Pro Gly Thr Val Lys Leu Leu Phe Met
        435                 440                 445

Lys Gln Tyr Gly Lys Phe Thr Asp Ile
    450                 455

<210> SEQ ID NO 7
<211> LENGTH: 4266
<212> TYPE: DNA
<213> ORGANISM: Staphylococcus aureus

<400> SEQUENCE: 7
atgacagagc aacaaaaatt taaagtgctt gctgatcaaa ttaaaatttc aaatcaatta      60
gatgctgaaa ttttaaattc aggtgaactg cacgtatag atgtttctaa caaaaacaga     120
acatgggaat tcatattac attaccacaa ttcttagctc atgaagatta tttattattt     180
ataaatgcaa tagagcaaga gtttaaagat atcgccaacg ttacatgtcg ttttacggta     240
acaaatggca cgaatcaaga tgaacatgca attaaatact tgggcactg tattgaccaa     300
acagctttat ctccaaaagt taaggtcaa ttgaaacaga aaaagcttat tatgtctgga     360
aaagtattaa aagtaatggt atcaaatgac attgaacgta tcattttga taaggcatgt     420
aatggaagtc ttatcaaagc gtttagaaat tgtggttttg atatcgataa aatcatattc     480
gaaacaaatg ataatgatca agaacaaaac ttagcttctt tagaagcaca tattcaagaa     540
gaagacgaac aaagtgcacg attggcaaca gagaaacttg aaaaaatgaa agctgaaaaa     600
gcgaaacaac aagataacaa gcaaagtgct gtcgataagt gtcaaattgg taagccgatt     660
caaattgaaa atattaaacc aattgaatct attattgagg aagagtttaa agttgcaata     720
gagggtgtca ttttttgatat aaacttaaaa gaacttaaaa gtggtcgcca tatcgtagaa     780
attaaagtga ctgactatac ggactcttta gttttaaaaa tgtttactcg taaaaacaaa     840
gatgatttag aacattttaa agcgctaagt gttggtaaat gggttagggc tcaaggtcgt     900
attgaagaag atacatttat tagagattta gttatgatga tgtctgatat tgaagagatt     960
aaaaaagcga caaaaaaaga taaggctgaa gaaaagcgag tagaattcca cttgcatact    1020
gcaatgagcc aaatggatgg tatacccaat attggtgcgt atgttaaaca ggcagcagac    1080
tggggacatc cagccattgc ggttacagac cataatgtgg gcaagcatt tccagatgct    1140
cacgcagcag cggaaaaaca tggcattaaa atgatatacg gtatggaagg tatgttagtt    1200
gatgatggtg ttccgattgc atacaaacca caagatgtcg tattaaaaga tgctacttat    1260
gttgtgttcg acgttgagac aactggttta tcaaatcagt atgataaaat catcgagctt    1320
gcagctgtga agttcataa cggtgaaatc atcgataagt ttgaaaggtt tagtaatccg    1380
catgaacgat tatcggaaac gattatcaat ttgacgcata ttactgatga tatgttagta    1440
gatgcccctg agattgaaga agtacttaca gagtttaaag aatgggttgg cgatgcgata    1500
ttcgtagcgc ataatgcttc gtttgatatg ggcttcatcg atacgggata tgaacgtctt    1560
```

```
gggtttggac catcaacgaa tggtgttatc gatactttag aattatctcg tacgattaat   1620
actgaatatg gtaaacatgg tttgaatttc ttggctaaaa aatatggcgt agaattaacg   1680
caacatcacc gtgccattta tgatacagaa gcaacagctt acattttcat aaaaatggtt   1740
caacaaatga agaattaggg cgtattaaat cataacgaaa tcaacaaaaa actcagtaat   1800
gaagatgcat ataaacgtgc aagacctagt catgtcacat taattgtaca aaaccaacaa   1860
ggtcttaaaa atctatttaa aattgtaagt gcatcattgg tgaagtattt ctaccgtaca   1920
cctcgaattc cacgttcatt gttagatgaa tatcgtgagg gattattggt aggtacagcg   1980
tgtgatgaag gtgaattatt tacggcagtt atgcagaagg accagagtca agttgaaaaa   2040
attgccaaat attatgattt tattgaaatt caaccaccgg cactttatca agatttaatt   2100
gatagagagc ttattagaga tactgaaaca ttacatgaaa tttatcaacg tttaatacat   2160
gcaggtgaca cagcgggtat acctgttatt gcgacaggaa atgcacacta tttgtttgaa   2220
catgatggta tcgcacgtaa aattttaata gcatcacaac ccggcaatcc acttaatcgc   2280
tcaactttac cggaagcaca ttttagaact acagatgaaa tgttaaacga gtttcatttt   2340
ttaggtgaag aaaaagcgca tgaaattgtt gtgaaaaata caaacgaatt agcagatcga   2400
attgaacgtg ttgttcctat taaagatgaa ttatacacac cgcgtatgga aggtgctaac   2460
gaagaaatta gagaactaag ttatgcaaat gcgcgtaaac tgtatggtga agacctgcct   2520
caaatcgtaa ttgatcgatt agaaaaagaa ttaaaaagta ttatcggtaa tggatttgcg   2580
gtaatttact taatttcgca acgtttagtt aaaaaatcat tagatgatgg atacttagtt   2640
ggttcccgtg gttcagtagg ttctagtttt gtagcgacaa tgactgagat tactgaagta   2700
aacccgttac cgccacacta tatttgtccg aactgtaaaa cgagtgaatt tttcaatgat   2760
ggttcagtag gatcaggatt tgatttacct gataagacgt gtgaaacttg tggagcgcca   2820
cttattaaag aaggacaaga tattccgttt gaaaaatttt taggatttaa gggagataaa   2880
gttcctgata tcgacttaaa ctttagtggt gaatatcaac cgaatgccca taactacaca   2940
aaagtattat ttggtgagga taaagtattc cgtgcaggta caattggtac tgttgctgaa   3000
aagactgctt ttggttatgt taaaggttat ttgaatgatc aaggtatcca caaagaggt   3060
gctgaaatag atcgactcgt taaaggatgt acaggtgtac ctgattacat ggatattat   3120
gattttacgc cgatacaata tcctgccgat gatcaaaatt cagcatggat gacgacacat   3180
tttgatttcc attctattca tgataatgta ttaaaacttg atatacttgg acacgatgat   3240
ccaacaatga ttcgtatgct tcaagattta tcaggaattg atccaaaaac aatacctgta   3300
gatgataaag aagttatgca gatatttagt acacctgaaa gtttgggtgt tactgaagat   3360
gaaattttat gtaaaacagg tacatttggg gtaccgaatt cggacaggat tcgtcgtcaa   3420
atgttagaag atacaaagcc aacaacattt tctgaattag ttcaaatctc aggattatct   3480
catggtacag atgtgtggtt aggcaatgct caagaattaa ttaaaaccgg tatatgtgat   3540
ttatcaagtg taattggttg tcgtgatgat atcatggttt attttaatgta tgctggttta   3600
gaaccatcaa tggcttttaa aataatggag tcagtacgta aaggtaaagg tttaactgaa   3660
gaaatgattg aaacgatgaa agaaaatgaa gtgccagatt ggtatttaga ttcatgtctt   3720
aaaattaagt acatattccc taaagcccat gcagcagcat acgttttaat ggcagtacgt   3780
atcgcatatt tcaaagtaca tcatccactt tattactatg catcttactt tacaattcgt   3840
gcgtcagact ttgatttaat cacgatgatt aaagataaaa caagcattcg aaatactgta   3900
```

-continued

```
aaagacatgt attctcgcta tatggatcta ggtaaaaaag aaaaagacgt attaacagtc   3960
ttggaaatta tgaatgaaat ggcgcatcga ggttatcgaa tgcaaccgat tagtttagaa   4020
aagagtcagg cgttcgaatt tatcattgaa ggcgatacac ttattccgcc gttcatatca   4080
gtgcctgggc ttggcgaaaa cgttgcgaaa cgaattgttg aagctcgtga cgatggccca   4140
tttttatcaa agaagatttt aaacaaaaaa gctggattat atcagaaaat tattgagtat   4200
ttagatgagt taggctcatt accgaattta ccagataaag ctcaactttc gatatttgat   4260
atgtaa                                                              4266
```

<210> SEQ ID NO 8
<211> LENGTH: 1435
<212> TYPE: PRT
<213> ORGANISM: Staphylococcus aureus

<400> SEQUENCE: 8

```
Met Thr Glu Gln Gln Lys Phe Lys Val Leu Ala Asp Gln Ile Lys Ile
  1               5                  10                  15

Ser Asn Gln Leu Asp Ala Glu Ile Leu Asn Ser Gly Glu Leu Thr Arg
             20                  25                  30

Ile Asp Val Ser Asn Lys Asn Arg Thr Trp Glu Phe His Ile Thr Leu
         35                  40                  45

Pro Gln Phe Leu Ala His Glu Asp Tyr Leu Leu Phe Ile Asn Ala Ile
     50                  55                  60

Glu Gln Glu Phe Lys Asp Ile Ala Asn Val Thr Cys Arg Phe Thr Val
 65                  70                  75                  80

Thr Asn Gly Thr Asn Gln Asp Glu His Ala Ile Lys Tyr Phe Gly His
                 85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
        115                 120                 125

Asn Asp Ile Glu Arg Asn His Phe Asp Lys Ala Cys Asn Gly Ser Leu
    130                 135                 140

Ile Lys Ala Phe Arg Asn Cys Gly Phe Asp Ile Asp Lys Ile Ile Phe
145                 150                 155                 160

Glu Thr Asn Asp Asn Asp Gln Glu Gln Asn Leu Ala Ser Leu Glu Ala
                165                 170                 175

His Ile Gln Glu Glu Asp Glu Gln Ser Ala Arg Leu Ala Thr Glu Lys
            180                 185                 190

Leu Glu Lys Met Lys Ala Glu Lys Ala Lys Gln Gln Asp Asn Lys Gln
        195                 200                 205

Ser Ala Val Asp Lys Cys Gln Ile Gly Lys Pro Ile Gln Ile Glu Asn
    210                 215                 220

Ile Lys Pro Ile Glu Ser Ile Ile Glu Glu Phe Lys Val Ala Ile
225                 230                 235                 240

Glu Gly Val Ile Phe Asp Ile Asn Leu Lys Glu Leu Lys Ser Gly Arg
                245                 250                 255

His Ile Val Glu Ile Lys Val Thr Asp Tyr Thr Asp Ser Leu Val Leu
            260                 265                 270

Lys Met Phe Thr Arg Lys Asn Lys Asp Asp Leu Glu His Phe Lys Ala
        275                 280                 285

Leu Ser Val Gly Lys Trp Val Arg Ala Gln Gly Arg Ile Glu Glu Asp
    290                 295                 300
```

```
Thr Phe Ile Arg Asp Leu Val Met Met Met Ser Asp Ile Glu Glu Ile
305                 310                 315                 320

Lys Lys Ala Thr Lys Lys Asp Lys Ala Glu Glu Lys Arg Val Glu Phe
            325                 330                 335

His Leu His Thr Ala Met Ser Gln Met Asp Gly Ile Pro Asn Ile Gly
            340                 345                 350

Ala Tyr Val Lys Gln Ala Ala Asp Trp Gly His Pro Ala Ile Ala Val
        355                 360                 365

Thr Asp His Asn Val Val Gln Ala Phe Pro Asp Ala His Ala Ala Ala
    370                 375                 380

Glu Lys His Gly Ile Lys Met Ile Tyr Gly Met Gly Met Leu Val
385                 390                 395                 400

Asp Asp Gly Val Pro Ile Ala Tyr Lys Pro Gln Asp Val Val Leu Lys
                405                 410                 415

Asp Ala Thr Tyr Val Val Phe Asp Val Glu Thr Thr Gly Leu Ser Asn
            420                 425                 430

Gln Tyr Asp Lys Ile Ile Glu Leu Ala Ala Val Lys Val His Asn Gly
        435                 440                 445

Glu Ile Ile Asp Lys Phe Glu Arg Phe Ser Asn Pro His Glu Arg Leu
450                 455                 460

Ser Glu Thr Ile Ile Asn Leu Thr His Ile Thr Asp Asp Met Leu Val
465                 470                 475                 480

Asp Ala Pro Glu Ile Glu Glu Val Leu Thr Glu Phe Lys Glu Trp Val
                485                 490                 495

Gly Asp Ala Ile Phe Val Ala His Asn Ala Ser Phe Asp Met Gly Phe
            500                 505                 510

Ile Asp Thr Gly Tyr Glu Arg Leu Gly Phe Gly Pro Ser Thr Asn Gly
        515                 520                 525

Val Ile Asp Thr Leu Glu Leu Ser Arg Thr Ile Asn Thr Glu Tyr Gly
    530                 535                 540

Lys His Gly Leu Asn Phe Leu Ala Lys Lys Tyr Gly Val Glu Leu Thr
545                 550                 555                 560

Gln His His Arg Ala Ile Tyr Asp Thr Glu Ala Thr Ala Tyr Ile Phe
                565                 570                 575

Ile Lys Met Val Gln Gln Met Lys Glu Leu Gly Val Leu Asn His Asn
            580                 585                 590

Glu Ile Asn Lys Lys Leu Ser Asn Glu Asp Ala Tyr Lys Arg Ala Arg
        595                 600                 605

Pro Ser His Val Thr Leu Ile Val Gln Asn Gln Gln Gly Leu Lys Asn
    610                 615                 620

Leu Phe Lys Ile Val Ser Ala Ser Leu Val Lys Tyr Phe Tyr Arg Thr
625                 630                 635                 640

Pro Arg Ile Pro Arg Ser Leu Leu Asp Glu Tyr Arg Glu Gly Leu Leu
                645                 650                 655

Val Gly Thr Ala Cys Asp Glu Gly Glu Leu Phe Thr Ala Val Met Gln
            660                 665                 670

Lys Asp Gln Ser Gln Val Glu Lys Ile Ala Lys Tyr Tyr Asp Phe Ile
        675                 680                 685

Glu Ile Gln Pro Pro Ala Leu Tyr Gln Asp Leu Ile Asp Arg Glu Leu
    690                 695                 700

Ile Arg Asp Thr Glu Thr Leu His Glu Ile Tyr Gln Arg Leu Ile His
705                 710                 715                 720

Ala Gly Asp Thr Ala Gly Ile Pro Val Ile Ala Thr Gly Asn Ala His
```

-continued

```
            725                 730                 735
Tyr Leu Phe Glu His Asp Gly Ile Ala Arg Lys Ile Leu Ile Ala Ser
            740                 745                 750
Gln Pro Gly Asn Pro Leu Asn Arg Ser Thr Leu Pro Glu Ala His Phe
            755                 760                 765
Arg Thr Thr Asp Glu Met Leu Asn Glu Phe His Phe Leu Gly Glu Glu
            770                 775                 780
Lys Ala His Glu Ile Val Val Lys Asn Thr Asn Glu Leu Ala Asp Arg
785                 790                 795                 800
Ile Glu Arg Val Val Pro Ile Lys Asp Glu Leu Tyr Thr Pro Arg Met
                    805                 810                 815
Glu Gly Ala Asn Glu Glu Ile Arg Glu Leu Ser Tyr Ala Asn Ala Arg
                    820                 825                 830
Lys Leu Tyr Gly Glu Asp Leu Pro Gln Ile Val Ile Asp Arg Leu Glu
                    835                 840                 845
Lys Glu Leu Lys Ser Ile Ile Gly Asn Gly Phe Ala Val Ile Tyr Leu
                    850                 855                 860
Ile Ser Gln Arg Leu Val Lys Lys Ser Leu Asp Asp Gly Tyr Leu Val
865                 870                 875                 880
Gly Ser Arg Gly Ser Val Gly Ser Ser Phe Val Ala Thr Met Thr Glu
                    885                 890                 895
Ile Thr Glu Val Asn Pro Leu Pro Pro His Tyr Ile Cys Pro Asn Cys
                    900                 905                 910
Lys Thr Ser Glu Phe Phe Asn Asp Gly Ser Val Gly Ser Gly Phe Asp
                    915                 920                 925
Leu Pro Asp Lys Thr Cys Glu Thr Cys Gly Ala Pro Leu Ile Lys Glu
                    930                 935                 940
Gly Gln Asp Ile Pro Phe Glu Lys Phe Leu Gly Phe Lys Gly Asp Lys
945                 950                 955                 960
Val Pro Asp Ile Asp Leu Asn Phe Ser Gly Glu Tyr Gln Pro Asn Ala
                    965                 970                 975
His Asn Tyr Thr Lys Val Leu Phe Gly Glu Asp Lys Val Phe Arg Ala
                    980                 985                 990
Gly Thr Ile Gly Thr Val Ala Glu Lys Thr Ala Phe Gly Tyr Val Lys
                    995                 1000                1005
Gly Tyr Leu Asn Asp Gln Gly Ile His Lys Arg Gly Ala Glu Ile Asp
            1010                1015                1020
Arg Leu Val Lys Gly Cys Thr Gly Val Arg Ala Thr Thr Gly Gln His
1025                1030                1035                1040
Pro Gly Gly Ile Ile Val Val Pro Asp Tyr Met Asp Ile Tyr Asp Phe
                    1045                1050                1055
Thr Pro Ile Gln Tyr Pro Ala Asp Asp Gln Asn Ser Ala Trp Met Thr
            1060                1065                1070
Thr His Phe Asp Phe His Ser Ile His Asp Asn Val Leu Lys Leu Asp
            1075                1080                1085
Ile Leu Gly His Asp Asp Pro Thr Met Ile Arg Met Leu Gln Asp Leu
            1090                1095                1100
Ser Gly Ile Asp Pro Lys Thr Ile Pro Val Asp Asp Lys Glu Val Met
1105                1110                1115                1120
Gln Ile Phe Ser Thr Pro Glu Ser Leu Gly Val Thr Glu Asp Glu Ile
                    1125                1130                1135
Leu Cys Lys Thr Gly Thr Phe Gly Val Pro Asn Ser Asp Arg Ile Arg
                    1140                1145                1150
```

Arg Gln Met Leu Glu Asp Thr Lys Pro Thr Thr Phe Ser Glu Leu Val
    1155                1160                1165

Gln Ile Ser Gly Leu Ser His Gly Thr Asp Val Trp Leu Gly Asn Ala
    1170                1175                1180

Gln Glu Leu Ile Lys Thr Gly Ile Cys Asp Leu Ser Val Ile Gly
1185                1190                1195                1200

Cys Arg Asp Asp Ile Met Val Tyr Leu Met Tyr Ala Gly Leu Glu Pro
                1205                1210                1215

Ser Met Ala Phe Lys Ile Met Glu Ser Val Arg Lys Gly Lys Gly Leu
                1220                1225                1230

Thr Glu Glu Met Ile Glu Thr Met Lys Glu Asn Glu Val Pro Asp Trp
                1235                1240                1245

Tyr Leu Asp Ser Cys Leu Lys Ile Lys Tyr Ile Phe Pro Lys Ala His
    1250                1255                1260

Ala Ala Ala Tyr Val Leu Met Ala Val Arg Ile Ala Tyr Phe Lys Val
1265                1270                1275                1280

His His Pro Leu Tyr Tyr Tyr Ala Ser Tyr Phe Thr Ile Arg Ala Ser
                1285                1290                1295

Asp Phe Asp Leu Ile Thr Met Ile Lys Asp Lys Thr Ser Ile Arg Asn
                1300                1305                1310

Thr Val Lys Asp Met Tyr Ser Arg Tyr Met Asp Leu Gly Lys Lys Glu
                1315                1320                1325

Lys Asp Val Leu Thr Val Leu Glu Ile Met Asn Glu Met Ala His Arg
    1330                1335                1340

Gly Tyr Arg Met Gln Pro Ile Ser Leu Glu Lys Ser Gln Ala Phe Glu
1345                1350                1355                1360

Phe Ile Ile Glu Gly Asp Thr Leu Ile Pro Pro Phe Ile Ser Val Pro
                1365                1370                1375

Gly Leu Gly Glu Asn Val Ala Lys Arg Ile Val Glu Ala Arg Asp Asp
                1380                1385                1390

Gly Pro Phe Leu Ser Lys Glu Asp Leu Asn Lys Lys Ala Gly Leu Tyr
                1395                1400                1405

Gln Lys Ile Ile Glu Tyr Leu Asp Glu Leu Gly Ser Leu Pro Asn Leu
    1410                1415                1420

Pro Asp Lys Ala Gln Leu Ser Ile Phe Asp Met
1425                1430                1435

<210> SEQ ID NO 9
<211> LENGTH: 1134
<212> TYPE: DNA
<213> ORGANISM: Staphylococcus aureus

<400> SEQUENCE: 9
atgatggaat tcactattaa aagagattat tttattacac aattaaatga cacattaaaa      60
gctatttcac caagaacaac attacctata ttaactggta tcaaaatcga tgcgaaagaa     120
catgaagtta tattaactgg ttcagactct gaaatttcaa tagaaatcac tattcctaaa     180
actgtagatg gcgaagatat tgtcaatatt tcagaaacag gctcagtagt acttcctgga     240
cgattctttg ttgatattat aaaaaaatta cctggtaaag atgttaaatt atctacaaat     300
gaacaattcc agacattaat tacatcaggt cattctgaat taatttgag tggcttagat     360 ccagatcaat atcctttatt acctcaagtt tctagagatg acgcaattca attgtcggta     420
aaagtactta aaaacgtgat tgcacaaacg aattttgcag tgtccacctc agaaacacgc     480

-continued

```
ccagtactaa ctggtgtgaa ctggcttata caagaaaatg aattaatatg cacagcgact      540
gattcacacc gcttggctgt aagaaagttg cagttagaag atgtttctga aaacaaaaat      600
gtcatcattc caggtaaggc tttagctgaa ttaaataaaa ttatgtctga caatgaagaa      660
gacattgata tcttctttgc ttcaaaccaa gtttttattta agttggaaa tgtgaacttt      720 atttctcgat tattagaagg acattatcct gatacaacac gtttattccc tgaaaactat      780
gaaattaaat taagtataga caatggggag ttttatcatg cgattgatcg tgcctcttta      840
ttagcacgtg aaggtggtaa taacgttatt aaattaagta caggtgatga cgttgttgaa      900
ttatcttcta catcaccaga aattggtact gtaaaagaag aagttgatgc aaacgatgtt      960
gaaggtggta gcctgaaaat ttcattcaac tctaaatata tgatggatgc tttaaaagca     1020
atcgataatg atgaggttga agttgaattc ttcggtacaa tgaaaccatt tattctaaaa     1080
ccaaaaggtg acgactcggt aacgcaatta attttaccaa tcagaactta ctaa           1134
```

<210> SEQ ID NO 10
<211> LENGTH: 377
<212> TYPE: PRT
<213> ORGANISM: Staphylococcus aureus

<400> SEQUENCE: 10

```
Met Met Glu Phe Thr Ile Lys Arg Asp Tyr Phe Ile Thr Gln Leu Asn
  1               5                  10                  15

Asp Thr Leu Lys Ala Ile Ser Pro Arg Thr Thr Leu Pro Ile Leu Thr
             20                  25                  30

Gly Ile Lys Ile Asp Ala Lys Glu His Glu Val Ile Leu Thr Gly Ser
         35                  40                  45

Asp Ser Glu Ile Ser Ile Glu Ile Thr Ile Pro Lys Thr Val Asp Gly
     50                  55                  60

Glu Asp Ile Val Asn Ile Ser Glu Thr Gly Ser Val Val Leu Pro Gly
 65                  70                  75                  80

Arg Phe Phe Val Asp Ile Ile Lys Lys Leu Pro Gly Lys Asp Val Lys
                 85                  90                  95

Leu Ser Thr Asn Glu Gln Phe Gln Thr Leu Ile Thr Ser Gly His Ser
            100                 105                 110

Glu Phe Asn Leu Ser Gly Leu Asp Pro Asp Gln Tyr Pro Leu Leu Pro
        115                 120                 125

Gln Val Ser Arg Asp Asp Ala Ile Gln Leu Ser Val Lys Val Leu Lys
    130                 135                 140

Asn Val Ile Ala Gln Thr Asn Phe Ala Val Ser Thr Ser Glu Thr Arg
145                 150                 155                 160

Pro Val Leu Thr Gly Val Asn Trp Leu Ile Gln Glu Asn Glu Leu Ile
                165                 170                 175

Cys Thr Ala Thr Asp Ser His Arg Leu Ala Val Arg Lys Leu Gln Leu
            180                 185                 190

Glu Asp Val Ser Glu Asn Lys Asn Val Ile Ile Pro Gly Lys Ala Leu
        195                 200                 205

Ala Glu Leu Asn Lys Ile Met Ser Asp Asn Glu Asp Ile Asp Ile
    210                 215                 220

Phe Phe Ala Ser Asn Gln Val Leu Phe Lys Val Gly Asn Val Asn Phe
225                 230                 235                 240

Ile Ser Arg Leu Leu Glu Gly His Tyr Pro Asp Thr Thr Arg Leu Phe
                245                 250                 255

Pro Glu Asn Tyr Glu Ile Lys Leu Ser Ile Asp Asn Gly Glu Phe Tyr
```

```
                260               265               270
His Ala Ile Asp Arg Ala Ser Leu Leu Ala Arg Glu Gly Gly Asn Asn
                275               280               285

Val Ile Lys Leu Ser Thr Gly Asp Asp Val Val Glu Leu Ser Ser Thr
            290               295               300

Ser Pro Glu Ile Gly Thr Val Lys Glu Val Asp Ala Asn Asp Val
305               310               315               320

Glu Gly Gly Ser Leu Lys Ile Ser Phe Asn Ser Lys Tyr Met Met Asp
                325               330               335

Ala Leu Lys Ala Ile Asp Asn Asp Glu Val Glu Val Glu Phe Phe Gly
                340               345               350

Thr Met Lys Pro Phe Ile Leu Lys Pro Lys Gly Asp Asp Ser Val Thr
            355               360               365

Gln Leu Ile Leu Pro Ile Arg Thr Tyr
        370               375

<210> SEQ ID NO 11
<211> LENGTH: 1719
<212> TYPE: DNA
<213> ORGANISM: Staphylococcus aureus

<400> SEQUENCE: 11
atgataggtt tgtgtccttt tcatgatgaa agacacctt catttacagt ttctgaagat      60
aaacaaatct gtcattgttt tggttgtaaa aaaggtggca atgtttttca atttactcaa    120
gaaattaaag acatatcatt tgttgaagcg gttaaagaat taggtgatag agttaatgtt    180
gctgtagata ttgaggcaac acaatctaac tcaaatgttc aaattgcttc tgatgattta    240
caaatgattg aaatgcatga gttaatacaa gaattttatt attacgcttt aacaaagaca    300
gtcgaaggcg aacaagcatt aacatactta caagaacgtg gttttacaga tgcgcttatt    360
aaagagcgag gcattggctt tgcacccgat agctcacatt tttgtcatga ttttcttcaa    420
aaaaagggtt acgatattga attagcatat gaagccggat tattatcacg taacgaagaa    480
aatttcagtt attacgatag atttcgaaat cgtattatgt ttcctttgaa aaatgcgcaa    540
ggaagaattg ttggatattc aggtcgaaca tataccggtc aagaaccaaa atacctaaat    600
agtcctgaaa cgcctatctt tcaaaaaaga aagttgttat ataacttaga taagcacgt    660 aaatcaatta gaaaattaga tgaaattgta ttactagaag gttttatgga tgttataaaa    720
tctgatactg ctggcttgaa aaacgttgtt gcaacaatgg gtacacagtt gtcagatgaa    780
catattacct ttatacgaaa gttaacatca aatataacat taatgtttga tggggatttt    840
gcgggtagtg aagcaacact taaacaggt caacatttgt tacagcaagg gctaaatgta    900
tttgttatac aattgccatc tggcatggat ccggatgaat acattggtaa gtatggcaac    960
gacgcattta ctactttgt aaaaaatgac aaaaagtcat tgcacatta taaagtaagt    1020 atattaaaag atgaaattgc acataatgac ctttcatatg aacgttattt gaaagaactg    1080
agtcatgaca tttcacttat gaagtcatca attctgcaac aaaaggctat aaatgatgtt    1140
gcgccatttt tcaatgttag tcctgagcag ttagctaacg aaatacaatt caatcaagca    1200
ccagccaatt attatccaga agatgagtat ggcggttatg atgagtatgg cggttatatt    1260
gaacctgagc caattggtat ggcacaattt gacaatttga gccgtcgaga aaaagcggag    1320
cgagcatttt taaacatttt aatgagagat aaagatacat ttttaaatta ttatgaaagt    1380
gttgataagg ataacttcac aaatcagcat tttaaatatg tattcgaagt cttacatgat    1440
```

-continued

```
ttttatgcgg aaaatgatca atataatatc agtgatgctg tgcagtatgt taattcaaat    1500
gagttgagag aaacactaat tagcttagaa caatataatt tgaatggcga accatatgaa    1560
aatgaaattg atgattatgt caatgttatt aatgaaaaag gacaagaaac aattgagtca    1620
ttgaatcata aattaaggga agctacaagg attggcgatg tagaattaca aaatactat    1680 ttacagcaaa ttgttgctaa gaataaagaa cgcatgtag                          1719
```

<210> SEQ ID NO 12
<211> LENGTH: 572
<212> TYPE: PRT
<213> ORGANISM: Staphylococcus aureus

<400> SEQUENCE: 12

```
Met Ile Gly Leu Cys Pro Phe His Asp Glu Lys Thr Pro Ser Phe Thr
 1               5                  10                  15

Val Ser Glu Asp Lys Gln Ile Cys His Cys Phe Gly Cys Lys Lys Gly
            20                  25                  30

Gly Asn Val Phe Gln Phe Thr Gln Glu Ile Lys Asp Ile Ser Phe Val
        35                  40                  45

Glu Ala Val Lys Glu Leu Gly Asp Arg Val Asn Val Ala Val Asp Ile
    50                  55                  60

Glu Ala Thr Gln Ser Asn Ser Asn Val Gln Ile Ala Ser Asp Asp Leu
65                  70                  75                  80

Gln Met Ile Glu Met His Glu Leu Ile Gln Glu Phe Tyr Tyr Tyr Ala
                85                  90                  95

Leu Thr Lys Thr Val Glu Gly Glu Gln Ala Leu Thr Tyr Leu Gln Glu
            100                 105                 110

Arg Gly Phe Thr Asp Ala Leu Ile Lys Glu Arg Gly Ile Gly Phe Ala
        115                 120                 125

Pro Asp Ser Ser His Phe Cys His Asp Phe Leu Gln Lys Lys Gly Tyr
    130                 135                 140

Asp Ile Glu Leu Ala Tyr Glu Ala Gly Leu Leu Ser Arg Asn Glu Glu
145                 150                 155                 160

Asn Phe Ser Tyr Tyr Asp Arg Phe Arg Asn Arg Ile Met Phe Pro Leu
                165                 170                 175

Lys Asn Ala Gln Gly Arg Ile Val Gly Tyr Ser Gly Arg Thr Tyr Thr
            180                 185                 190

Gly Gln Glu Pro Lys Tyr Leu Asn Ser Pro Glu Thr Pro Ile Phe Gln
        195                 200                 205

Lys Arg Lys Leu Leu Tyr Asn Leu Asp Lys Ala Arg Lys Ser Ile Arg
    210                 215                 220

Lys Leu Asp Glu Ile Val Leu Leu Glu Gly Phe Met Asp Val Ile Lys
225                 230                 235                 240

Ser Asp Thr Ala Gly Leu Lys Asn Val Val Ala Thr Met Gly Thr Gln
                245                 250                 255

Leu Ser Asp Glu His Ile Thr Phe Ile Arg Lys Leu Thr Ser Asn Ile
            260                 265                 270

Thr Leu Met Phe Asp Gly Asp Phe Ala Gly Ser Glu Ala Thr Leu Lys
        275                 280                 285

Thr Gly Gln His Leu Leu Gln Gln Gly Leu Asn Val Phe Val Ile Gln
    290                 295                 300

Leu Pro Ser Gly Met Asp Pro Asp Glu Tyr Ile Gly Lys Tyr Gly Asn
305                 310                 315                 320

Asp Ala Phe Thr Thr Phe Val Lys Asn Asp Lys Lys Ser Phe Ala His
```

```
                  325                 330                 335
Tyr Lys Val Ser Ile Leu Lys Asp Glu Ile Ala His Asn Asp Leu Ser
                340                 345                 350

Tyr Glu Arg Tyr Leu Lys Glu Leu Ser His Asp Ile Ser Leu Met Lys
            355                 360                 365

Ser Ser Ile Leu Gln Gln Lys Ala Ile Asn Asp Val Ala Pro Phe Phe
        370                 375                 380

Asn Val Ser Pro Glu Gln Leu Ala Asn Glu Ile Gln Phe Asn Gln Ala
385                 390                 395                 400

Pro Ala Asn Tyr Tyr Pro Glu Asp Glu Tyr Gly Gly Tyr Asp Glu Tyr
                405                 410                 415

Gly Gly Tyr Ile Glu Pro Glu Pro Ile Gly Met Ala Gln Phe Asp Asn
                420                 425                 430

Leu Ser Arg Arg Glu Lys Ala Glu Arg Ala Phe Leu Lys His Leu Met
            435                 440                 445

Arg Asp Lys Asp Thr Phe Leu Asn Tyr Tyr Glu Ser Val Asp Lys Asp
        450                 455                 460

Asn Phe Thr Asn Gln His Phe Lys Tyr Val Phe Glu Val Leu His Asp
465                 470                 475                 480

Phe Tyr Ala Glu Asn Asp Gln Tyr Asn Ile Ser Asp Ala Val Gln Tyr
                485                 490                 495

Val Asn Ser Asn Glu Leu Arg Glu Thr Leu Ile Ser Leu Glu Gln Tyr
                500                 505                 510

Asn Leu Asn Gly Glu Pro Tyr Glu Asn Glu Ile Asp Asp Tyr Val Asn
            515                 520                 525

Val Ile Asn Glu Lys Gly Gln Glu Thr Ile Glu Ser Leu Asn His Lys
        530                 535                 540

Leu Arg Glu Ala Thr Arg Ile Gly Asp Val Glu Leu Gln Lys Tyr Tyr
545                 550                 555                 560

Leu Gln Gln Ile Val Ala Lys Asn Lys Glu Arg Met
                565                 570

<210> SEQ ID NO 13
<211> LENGTH: 29
<212> TYPE: DNA
<213> ORGANISM: Staphylococcus aureus

<400> SEQUENCE: 13
ggtggtaatt gtcttgcata tgacagagc                                     29

<210> SEQ ID NO 14
<211> LENGTH: 30
<212> TYPE: DNA
<213> ORGANISM: Staphylococcus aureus

<400> SEQUENCE: 14
agcgattaag tggattgccg ggttgtgatg                                    30

<210> SEQ ID NO 15
<211> LENGTH: 31
<212> TYPE: DNA
<213> ORGANISM: Staphylococcus aureus

<400> SEQUENCE: 15
agcatcacaa cccggcaatc cacttaatcg c                                  31

<210> SEQ ID NO 16
```

```
<211> LENGTH: 29
<212> TYPE: DNA
<213> ORGANISM: Staphylococcus aureus

<400> SEQUENCE: 16
gactacgcca tgggcattaa ataaatacc                                              29

<210> SEQ ID NO 17
<211> LENGTH: 31
<212> TYPE: DNA
<213> ORGANISM: Staphylococcus aureus

<400> SEQUENCE: 17
gaagatgcat ataaacgtgc aagacctagt c                                           31

<210> SEQ ID NO 18
<211> LENGTH: 34
<212> TYPE: DNA
<213> ORGANISM: Staphylococcus aureus

<400> SEQUENCE: 18
gtctgacgca cgaattgtaa agtaagatgc atag                                        34

<210> SEQ ID NO 19
<211> LENGTH: 36
<212> TYPE: DNA
<213> ORGANISM: Staphylococcus aureus

<400> SEQUENCE: 19
cgactggaag gagttttaac atatgatgga attcac                                      36

<210> SEQ ID NO 20
<211> LENGTH: 30
<212> TYPE: DNA
<213> ORGANISM: Staphylococcus aureus

<400> SEQUENCE: 20
ttatatggat ccttagtaag ttctgattgg                                             30

<210> SEQ ID NO 21
<211> LENGTH: 15
<212> TYPE: PRT
<213> ORGANISM: Staphylococcus aureus

<400> SEQUENCE: 21

Leu Leu Phe Glu Arg Phe Leu Asn Pro Glu Arg Val Ser Met Pro
 1               5                  10                  15

<210> SEQ ID NO 22
<211> LENGTH: 15
<212> TYPE: PRT
<213> ORGANISM: Staphylococcus aureus

<400> SEQUENCE: 22

Lys Phe Ala Gly Tyr Gly Phe Asn Lys Ser His Ser Ala Ala Tyr
 1               5                  10                  15

<210> SEQ ID NO 23
<211> LENGTH: 44
<212> TYPE: DNA
<213> ORGANISM: Staphylococcus aureus

<400> SEQUENCE: 23 cttcttttg aaagatttct aaataaagaa cgttattcaa tgcc                              44
```

<210> SEQ ID NO 24
<211> LENGTH: 45
<212> TYPE: DNA
<213> ORGANISM: Staphylococcus aureus

<400> SEQUENCE: 24
ataagctgca gcatgacttt tattaaaacc ataacctgca aattt					45

<210> SEQ ID NO 25
<211> LENGTH: 39
<212> TYPE: DNA
<213> ORGANISM: Staphylococcus aureus

<400> SEQUENCE: 25
agttaaaaat gccatatttt gacgtgtttt agttctaat					39

<210> SEQ ID NO 26
<211> LENGTH: 42
<212> TYPE: DNA
<213> ORGANISM: Staphylococcus aureus

<400> SEQUENCE: 26
cttgcaaaag cggttgctaa agatgttgga cgaattatgg gg					42

<210> SEQ ID NO 27
<211> LENGTH: 10
<212> TYPE: PRT
<213> ORGANISM: Staphylococcus aureus

<400> SEQUENCE: 27

His Ala Tyr Leu Phe Ser Gly Pro Arg Gly
 1               5                  10

<210> SEQ ID NO 28
<211> LENGTH: 11
<212> TYPE: PRT
<213> ORGANISM: Staphylococcus aureus

<400> SEQUENCE: 28

Ala Leu Leu Lys Thr Leu Glu Glu Pro Pro Glu
 1               5                  10

<210> SEQ ID NO 29
<211> LENGTH: 38
<212> TYPE: DNA
<213> ORGANISM: Staphylococcus aureus

<400> SEQUENCE: 29
cgcggatccc atgcatattt attttcaggt ccaagagg					38

<210> SEQ ID NO 30
<211> LENGTH: 10
<212> TYPE: PRT
<213> ORGANISM: Staphylococcus aureus

<400> SEQUENCE: 30

His Ala Tyr Leu Phe Ser Gly Pro Arg Gly
 1               5                  10

<210> SEQ ID NO 31
<211> LENGTH: 39
<212> TYPE: DNA
<213> ORGANISM: Staphylococcus aureus -continued

<400> SEQUENCE: 31
ccggaattct ggtggttctt ctaatgtttt taataatgc                                39

<210> SEQ ID NO 32
<211> LENGTH: 11
<212> TYPE: PRT
<213> ORGANISM: Staphylococcus aureus

<400> SEQUENCE: 32

Ala Leu Leu Lys Thr Leu Glu Glu Pro Pro Glu
 1               5                  10

<210> SEQ ID NO 33
<211> LENGTH: 38
<212> TYPE: DNA
<213> ORGANISM: Staphylococcus aureus

<400> SEQUENCE: 33
tttgtaaagg cattacgcag gggactaatt cagatgtg                                 38

<210> SEQ ID NO 34
<211> LENGTH: 33
<212> TYPE: DNA
<213> ORGANISM: Staphylococcus aureus

<400> SEQUENCE: 34
tatgacattc attacaaggt tctccatcag tgc                                      33

<210> SEQ ID NO 35
<211> LENGTH: 29
<212> TYPE: DNA
<213> ORGANISM: Staphylococcus aureus

<400> SEQUENCE: 35
gagcactgat gaacttagaa ttagatatg                                           29

<210> SEQ ID NO 36
<211> LENGTH: 32
<212> TYPE: DNA
<213> ORGANISM: Staphylococcus aureus

<400> SEQUENCE: 36
gatactcagt atctttctca gatgttttat tc                                       32

<210> SEQ ID NO 37
<211> LENGTH: 14
<212> TYPE: PRT
<213> ORGANISM: Staphylococcus aureus

<400> SEQUENCE: 37

Asp Leu Ile Ile Val Ala Ala Arg Pro Ser Met Gly Lys Thr
 1               5                  10

<210> SEQ ID NO 38
<211> LENGTH: 15
<212> TYPE: PRT
<213> ORGANISM: Staphylococcus aureus

<400> SEQUENCE: 38

Glu Ile Ile Ile Gly Lys Gln Arg Asn Gly Pro Ile Gly Thr Val
 1               5                  10                  15

```
<210> SEQ ID NO 39
<211> LENGTH: 41
<212> TYPE: DNA
<213> ORGANISM: Staphylococcus aureus

<400> SEQUENCE: 39
gaccttataa ttgtagctgc acgtccttct atgggaaaaa c                    41

<210> SEQ ID NO 40
<211> LENGTH: 48
<212> TYPE: DNA
<213> ORGANISM: Staphylococcus aureus

<400> SEQUENCE: 40
aacattatta agtcagcatc ttgttctatt gatccagatt caacgaag             48

<210> SEQ ID NO 41
<211> LENGTH: 45
<212> TYPE: DNA
<213> ORGANISM: Staphylococcus aureus

<400> SEQUENCE: 41
gatttgtagt tctggtaatg ttgactcaaa ccgcttaaga accgg                45

<210> SEQ ID NO 42
<211> LENGTH: 48
<212> TYPE: DNA
<213> ORGANISM: Staphylococcus aureus

<400> SEQUENCE: 42
atacgtgtgg ttaactgatc agcaacccat ctctagtgag aaaatacc             48

<210> SEQ ID NO 43
<211> LENGTH: 31
<212> TYPE: DNA
<213> ORGANISM: Staphylococcus aureus

<400> SEQUENCE: 43
cgttttaatg catgcttaga aacgatatca g                               31

<210> SEQ ID NO 44
<211> LENGTH: 31
<212> TYPE: DNA
<213> ORGANISM: Staphylococcus aureus

<400> SEQUENCE: 44
cattgctaag caacgttacg gtccaacagg c                               31
```

ISOLATED *STAPHYLOCOCCUS* DNAX SUBUNIT AND USE THEREOF

This application is a continuation of U.S. patent application Ser. No. 09/235,245 filed Jan. 22, 1999 now abandoned, which claims benefit of U.S. Provisional Patent Application Nos. 60/074,522 and 60/093,727, filed Jan. 27, 1998, and Jul. 22, 1998, respectively.

The present invention was made with funding from National Institutes of Health Grant No. GM38839. The United Stated Government may have certain rights in this invention.

FIELD OF THE INVENTION

This invention relates to genes and proteins that replicate the chromosome of Gram positive bacteria. These proteins can be used in drug discovery to screen large libraries of chemicals for identification of compounds with antibiotic activity.

BACKGROUND OF THE INVENTION

All forms of life must duplicate the genetic material to propagate the species. The process by which the DNA in a chromosome is duplicated is called replication. The replication process is performed by numerous proteins that coordinate their actions to smoothly duplicate the DNA. The main protein actors are as follows (reviewed in Kornberg, et al., *DNA Replication*, Second Edition, New York: W. H. Freeman and Company, pp. 165-194 (1992)). A helicase uses the energy of ATP hydrolysis to unwind the two DNA strands of the double helix. Two copies of the DNA polymerase use each "daughter" strand as a template to convert them into two new duplexes. The DNA polymerase acts by polymerizing the four monomer unit building blocks of DNA (the 4 dNTPs, or deoxynucleoside triphosphates are: dATP, dCTP, dGTP, dTTP). The polymerase rides along one strand of DNA using it as a template that dictates the sequence in which the monomer blocks are to be polymerized. Sometimes the DNA polymerase makes a mistake and includes an incorrect nucleotide (e.g., A instead of G). A proofreading exonuclease examines the polymer as it is made and excises building blocks that have been improperly inserted in the polymer.

Duplex DNA is composed of two strands that are oriented antiparallel to one another, one being oriented 3'-5' and the other 5' to 3'. As the helicase unwinds the duplex, the DNA polymerase moves continuously forward with the helicase on one strand (called the leading strand). However, due to the fact that DNA polymerases can only extend the DNA forward from a 3' terminus, the polymerase on the other strand extends DNA in the opposite direction of DNA unwinding (called the lagging strand). This necessitates a discontinuous ratcheting motion on the lagging strand in which the DNA is made as a series of Okazaki fragments. DNA polymerases cannot initiate DNA synthesis de novo, but require a primed site (i.e. a short duplex region). This job is fulfilled by primase, a specialized RNA polymerase, that synthesizes short RNA primers on the lagging strand. The primed sites are extended by DNA polymerase. A single stranded DNA binding protein (SSB) is also needed; it operates on the lagging strand. The function of SSB is to coat single stranded DNA (ssDNA), thereby melting short hairpin duplexes that would otherwise impede DNA synthesis by DNA polymerase.

The replication process is best understood for the Gram negative bacterium, *Escherichia coli*, and its bacteriophages T4 and T7 (reviewed in Kelman, et al., "DNA Polymerase III Holoenzyme: Structure and Function of Chromosomal Replicating Machine," *Annu. Rev. Biochem.*, 64:171-200 (1995); Marians, K. J., "Prokaryotic DNA Replication," *Annu. Rev. Biochem.*, 61:673-719 (1992); McHenry, C. S., "DNA Polymerase III Holoenzyme: Components, Structure, and Mechanism of a True Replicative Complex," *J. Bio. Chem.*, 266: 19127-19130 (1991); Young et. al., "Structure and Function of the Bacteriophage T4 DNA Polymerase Holoenzyme," *Am. Chem. Soc.*, 31:8675-8690 (1992)). The eukaryotic systems of yeast (*Saccharomyces cerevisae*) (Morrison et. al., "A Third Essential DNA Polymerase in *S. cerevisiae*," *Cell*, 62:1143-51 (1990) and humans (Bambara, et al., "Reconstitution of Mammalian DNA Replication," *Prog. Nuc. Acid Res.*," 51:93-123 (1995)) have also been characterized in some detail as has herpes virus (Boehmer, et al., "Herpes Simplex Virus DNA Replication," *Annu. Rev. Biochem.*, 66:347-384 (1997)) and vaccinia virus (McDonald, et. al., "Characterization of a Processive Form of the Vaccinia Virus DNA Polymerase," *Virology*, 234:168-175 (1997)). The helicase of *E. coli* is encoded by the dnaB gene and is called the DnaB-helicase. In phage T4, the helicase is the product of the gene 41, and, in T7, it is the product of gene 4. Generally, the helicase contacts the DNA polymerase, in *E. coli*. This contact is necessary for the helicase to achieve the catalytic efficiency needed to replicate a chromosome (Kim, et. al., "Coupling of a Replicative Polymerase and Helicase: A tau-DnaB Interaction Mediates Rapid Replication Fork Movement," *Cell*, 84:643-650 (1996)). The identity of the helicase that acts at the replication fork in a eukaryotic cellular system is still not firm.

The primase of *E. coli* (product of the dnaG gene), phage T4 (product of gene 61), and T7 (gene 4) require the presence of their cognate helicase for activity. The primase of eukaryotes, called DNA polymerase alpha, looks and behaves differently. DNA polymerase alpha is composed of 4 subunits. The primase activity is associated with the two smaller subunits, and the largest subunit is the DNA polymerase which extends the product of the priming subunits. DNA polymerase alpha does not need a helicase for priming activity.

The chromosomal replicating DNA polymerase of all these systems, prokaryotic and eukaryotic, share the feature that they are processive, meaning they remain continuously associated with the DNA template as they link monomer units (dNTPs) together. This catalytic efficiency can be manifest in vitro by their ability to extend a single primer around a circular single stranded DNA (ssDNA) of over 5,000 nucleotide units in length. Chromosomal DNA polymerases will be referred to here as replicases to distinguish them from DNA polymerases that function in other DNA metabolic processes and are far less processive.

There are three types of replicases known thus far that differ in how they achieve processivity, and how their subunits are organized. These will be referred to here as Types I-III. The Type I is exemplified by the phage T5 replicase, which is composed of only one subunit yet is highly processive (Das, et al., "Mechanism of Primer-template Dependent Conversion of dNTP-dNMP by T7 DNA Polymerase," *J. Biol. Chem.*, 255:7149-7154 (1980)). It is possible that the T5 enzyme achieves processivity by having a cavity within it for binding DNA, and that a domain of the protein acts as a lid that opens to accept the DNA, and closes to trap the DNA inside, thereby keeping the polymerase on DNA during polymerization of dNTPs. Type II is exemplified by the replicases of phage T7, herpes simplex virus, and vaccinia virus. In these systems, the replicase is composed of two subunits, the DNA polymerase and an "accessory protein" which is needed for the polymerase to become highly efficient. It is presumed that the DNA polymerase binds the DNA in a groove and that the accessory protein forms a cap over the groove trapping the DNA inside for processive action. Type III is exemplified by the replicases of *E. coli*, phage T4, yeast, and humans in which there are three separate components, a sliding clamp protein, a clamp loader protein complex, and the DNA polymerase. In these systems, the sliding clamp protein is an oligomer in the shape of a ring. The clamp loader is a multi-protein complex which uses ATP to assemble the clamp around DNA. The DNA polymerase then binds the clamp which tethers the polymerase to DNA for high processivity. The replicase of the *E. coli* system contains a fourth component called tau that acts as a glue to hold two polymerases and one clamp loader together into one structure called Pol III*. In this application, any replicase that uses a minimum of three components (i.e. clamp, clamp loader, and DNA polymerase) will be referred to as either a type III enzyme or as a DNA polymerase III-type replicase.

The *E. coli* replicase is also called DNA polymerase III holoenzyme. The holoenzyme is a single multiprotein particle that contains all the components and therefore is composed of 10 different proteins. This holoenzyme is suborganized into four functional components called: 1) Pol III core (DNA polymerase); 2) gamma complex (clamp loader); 3) beta subunit (sliding clamp); and 4) tau (glue protein). The DNA polymerase III "core" is a tightly associated complex containing one each of the following three subunits: 1) the alpha subunit is the actual DNA polymerase (129 kDa); 2) the epsilon subunit (28 kDa) contains the proofreading 3'-5' exonuclease activity; and 3) the theta subunit has an unknown function. The gamma complex is the clamp loader and contains the following subunits: gamma, delta, delta prime, chi and psi (U.S. Pat. No. 5,583,026 to O'Donnell). The beta subunit is a homodimer and forms the ring shaped sliding clamp. These components associate to form the holoenzyme and the entire holoenzyme can be assembled in vitro from 10 isolated pure subunits (U.S. Pat. No. 5,583,026 to O'Donnell; U.S. Pat. No. 5,668,004 to O'Donnell). The tau subunit, encoded by the same gene that encodes gamma (dnaX), acts as a glue to hold two cores together with one gamma complex. This subassembly is called DNA polymerase III star (Pol III*). One beta ring interacts with each core in Pol III* to form DNA polymerase III holoenzyme.

During replication, the two cores in the holoenzyme act coordinately to synthesize both strands of DNA in a duplex chromosome. At the replication fork, DNA polymerase III holoenzyme physically interacts with the DnaB helicase through the tau subunit to form a yet larger protein complex termed the "replisome" (Kim, et. al., "Coupling of a Replicative Polymerase and Helicase: A tau-DnaB Interaction Mediates Rapid Replication Fork Movement," *Cell*, 84:643-650 (1996); Yuzhakov, et. al., "Replisome Assembly Reveals the Basis for Asymmetric Function in Leading and Lagging Strand Replication," *Cell*, 86:877-886 (1996)). The primase repeatedly contacts the helicase during replication fork movement to synthesize RNA primers on the lagging strand (Marians, K. J., "Prokaryotic DNA Replication," *Annu. Rev. Biochem.*, 61:673-719 (1992)).

In the present invention, new genes from Gram positive bacteria (e.g., *S. aureus*) are identified. Although their homology with *E. coli* proteins is often weak, they will be assigned names based on their nearest homology to subunits in the *E. coli* system. The gene of *E. coli* replication proteins are as follows: alpha (dnaE); epsilon (dnaQ); theta (holE); tau (dnaX); gamma (dnaX); delta (holA); delta prime (holB); chi (holC); psi (holD); beta (dnaN); DnaB; helicase (dnaB); and primase (dnaG).

The dnaX gene encodes both tau and gamma. Tau is the product of the full gene. Gamma is the product of the first ⅔ of the gene; it is truncated by an efficient translational frameshift that results in incorporation of one unique residue followed by a stop codon.

Although there are many studies of replication mechanisms in eukaryotes, and the Gram negative bacterium, *E. coli* and its bacteriophages, there is very little information about how Gram positive organisms replicate. The evolutionary split between Gram positive bacteria and Gram negative bacteria occurred approximately 1.2 billion years ago. The Gram positive class of bacteria includes some of the worst human pathogens such as *Staphylococcus aureus*, *Streptococcus pneumoniae*, *Streptococcus pyogenes*, *Enterococcus faecalis*, and *Mycobacterium tuberculosis* (Youmans, et. al., *The Biological and Clinical Basis of Infectious Disease* (1985)).

Currently, the best characterized Gram positive organism for DNA synthesis is *Bacillus subtilis*. Fractionation of *B. subtitis* has identified three DNA polymerases. Gass, et al., "Further Genetic and Enzymological Characterization of the Three *Bacillus subtilis* Deoxyribonucleic Acid Polymerases," *J. Bio. Chem.*, 248:7688-7700 (1973); Ganesan, et. al.; "DNA Replication in a Polymerase I Deficient Mutant and the Identification of DNA Polymerases II and III in *Bacillus subtilis*," Biochem. And Biophy. Res. Commun., 50:155-163 (1973)). These polymerases are thought to be analogous to the three DNA polymerases of *E. coli* (DNA polymerases I, II and III). Studies in *B. subtilis* have identified a polymerase that appears to be involved in chromosome replication and is termed Pol III (Ott, et. al.; "Cloning and Characterization of the PolC Region of *Bacillus subtilis*," *J. Bacteriol.*, 165:951-957 (1986); Barnes, et. al., "Localization of the Exonuclease and Polymerase Domains of *Bacillus subtilis* DNA Polymerase III," *Gene*, 111:43-49 (1992); Barnes, et. al., "The 3'-5' Exonuclease Site of DNA Polymerase III From Gram-positive Bacteria: Definition of a Novel Motif Structure," *Gene*" 165:45-50 (1995) or Barnes, et al., "Purification of DNA Polymerase III of Gram-positive Bacteria," *Methods in Enzy.*, 262:35-42 (1995)). The *B. subtilis* Pol III (called PolC) is larger (about 165 kDa) than the *E. coli* alpha subunit (about 129 kDa) and exhibits 3'-5' exonuclease activity. The PolC gene encoding this Pol III shows weak homology to the genes encoding *E. coli* alpha and the *E. coli* epsilon subunit. Hence, this long form of the *B. subtilis* Pol III (herein referred to as Pol III-L) essentially comprises both the alpha and epsilon subunits of the *E. coli* core polymerase. The *S. aureus* Pol III-L has also been sequenced, expressed in *E. coli* and purified; it contains polymerase and 3'-5' exonuclease activity (Pacitti, et. al., "Characterization and Overexpression of the Gene Encoding *Staphylococcus aureus* DNA Polymerase III," *Gene*, 165:51-56 (1995)). Although this Pol III-L is essential to cell growth (Clements, et. al., "Inhibition of *Bacillus subtilis* Deoxyribonucleic Acid Polymerase III by Phenylhydrazinopyrimidines: Demonstration of a Drug-induced Deoxyribonucleic Acid-Enzyme Complex," *J. Biol. Chem.*, 250:522-526 (1975); Cozzarelli, et al., "Mutational Alteraction of *Bacillus subtilis* DNA Polymerase III to Hydroxyphenylazopyrimidine Resistance: Polymerase III is Necessary for DNA Replication," *Biochem. And Biophy. Res. Commun.*, 51:151-157 (1973); Low, et. al., "Mechanism of Inhibition of *Bacillus subtilis* DNA Polymerase III by the Arylhydrazinopyrimidine Antimicrobial Agents," *Proc. Natl. Acad. Sci. USA*, 71:2973-2977 (1974)), there could still be another DNA polymerase(s) that is essential to the cell, such as occurs in yeast (Morrison, et. al., "A Third Essential DNA Polymerase in *S. cerevisiae*," *Cell*, 62:1143-1151 (1990)).

Purification of Pol III-L from *B. subtilis* results in only this single protein without associated proteins Barnes, et. al., "Localization of the Exonuclease and Polymerase Domains of *Bacillus subtilis* DNA Polymerase III," *Gene*, 111:43-49 (1992); Barnes, et. al., "The 3'-5' Exonuclease Site of DNA Polymerase III From Gram-positive Bacteria: Definition of a Novel Motif Structure," *Gene* " 165:45-50 (1995) or Barnes, et al., "Purification of DNA Polymerase III of Gram-positive Bacteria," *Methods in Enzy.*, 262:35-42 (1995)). Hence, it is possible that Pol III-L is a member of the Type I replicase (like T5) in which it is processive on its own without accessory proteins. *B. subtilis* and *S. aureus* also have a gene encoding a protein that has approximately 30% homology to the beta subunit of *E. coli*; however the protein product has not been purified or characterized (Alonso, et al., "Nucleotide Sequence of the recF Gene Cluster From *Staphylococcus aureus* and Complementation Analysis in *Bacillus subtilis* recF Mutants," *Mol. Gen. Genet.*, 246:680-686 (1995); Alonso, et al., "Nucleotide Sequence of the recF Gene Cluster From *Staphylococcus aureus* and Complementation Analysis in *Bacillus subtilis* recF Mutants," *Mol. Gen. Genet.*, 248: 635-636 (1995)). Whether this beta subunit has a function in replication, a ring shape, or functions as a sliding clamp is not known. Even if this beta homolog is involved in replication, it is not known whether it is functional with Pol III-L or another polymerase.

There remains a need to understand the process of DNA replication in Gram positive cells at a molecular level. It is possible that a more detailed understanding of replication proteins will lead to discovery of new antibiotics. Therefore, a deeper understanding of replication proteins of Gram positive bacteria, particularly members of the Staphylococcus genus is especially important given the emergence of drug resistant strains of these organisms. For example, *Staphylococcus aureus* has successfully mutated to become resistant to all common antibiotics.

The "target" protein(s) of an antibiotic drug is generally involved in a critical cell function, such that blocking its action with a drug causes the pathogenic cell to die or no longer proliferate. Current antibiotics are directed to very few targets. These include membrane synthesis proteins (e.g. vancomycin, penicillin, and its derivatives such as ampicillin, amoxicillin, and cephalosporin), the ribosome machinery (tetracycline, chloramphenicol, azithromycin, and the aminoglycosides: kanamycin, neomycin, gentamicin, streptomycin), RNA polymerase (rifampimycin), and DNA topoisomerases (novobiocin, quinolones, and fluoroquinolones). The DNA replication apparatus is a crucial life process, and, thus, the proteins involved in this process are also good targets for antibiotics.

A powerful approach to discovery of a new drug is to obtain a target protein, characterize it, and develop in vitro assays of its cellular function. Large chemical libraries are then screened in the functional assays to identify compounds that inhibit the target protein. These candidate pharmaceuticals are then chemically modified to optimize their potency, breadth of antibiotic spectrum, performance in animal models, non toxicity, and, finally, clinical trials. The screening of large chemical libraries requires a plentiful source of the target protein. An abundant supply of protein generally requires overproduction techniques using the gene encoding the protein. This is especially true for replication proteins as they are present in low abundance in the cell.

Selective and robust assays are needed to screen reliably a large chemical library. The assay should be insensitive to most chemicals in the concentration range normally used in the drug discovery process. These assays should also be selective and not show inhibition by antibiotics known to target proteins in processes outside of replication. The present invention is directed to overcoming these deficiencies in the art.

SUMMARY OF THE INVENTION

The present invention relates to various isolated DNA molecules from Gram positive bacteria. These include dnaE, dnaX, dnaB, PolC, dnaN, beta, and dnaG DNA molecules for Gram positive bacteria. These DNA molecules can be inserted into an expression system or used to transform host cells. The isolated proteins encoded by these DNA molecules are also disclosed.

The present invention aims to understand the structure and mechanism of the chromosomal replicase of Gram positive bacteria and how it functions with a helicase and primase. This knowledge and the enzymes involved in the replication process can be used for the purpose of screening for potential antibiotic drugs. Further, information about chromosomal replicases may be useful in DNA sequencing, polymerase chain reaction, and other DNA polymerase related techniques.

The present invention identifies the type of replicase that Gram positive bacteria employ for chromosome replication. Rather than use a DNA polymerase that attains high efficiency on its own, or with one other subunit, the Gram positive bacteria replicase is the Pol III-type of replicase (class III) that uses a sliding clamp protein. The Gram positive bacteria replicase also uses a clamp loader component that assembles the sliding clamp onto DNA.

The present invention identifies two DNA polymerases (both of Pol III type) in Gram positive bacteria that utilize the sliding clamp and clamp loader. The invention also identifies a gene with homology to the alpha subunit of *E. coli* DNA polymerase III holoenzyme, the chromosomal replicase of *E. coli*. These DNA polymerases can extend a primer around a large circular natural template when the beta clamp has been assembled onto the primed ssDNA by the clamp loader or a primer on a linear DNA where the beta clamp may assemble by itself by sliding over an end.

The present invention shows that the clamp and clamp loader components of Gram negative cells can be exchanged for those of Gram positive cells in that the clamp, once assembled onto DNA, will function with Pol III obtained from either Gram positive and Gram negative sources. This result implies that important contacts between the polymerase and clamp have been conserved during evolution. Therefore, these "mixed systems" may provide assays for an inhibitor of this conserved interaction. Such an inhibitor may be expected to shut down replication, and since the interaction is apparently conserved across the evolutionary spectrum from Gram positive and Gram negative cells, the inhibitor may exhibit a broad spectrum of antibiotic activity. Further, these "mixed" systems are composed of all overexpressed and purified proteins (8 total; 1 from *S. aureus* and 7 from *E. coli*) making possible large quantities of protein needed for high throughput screening of hundreds of thousands of chemicals.

The present invention demonstrates that Gram positive bacteria contain a beta subunit that behaves as a sliding clamp that encircles DNA. A dnaX gene sequence encoding a protein homolog of the gamma/tau subunit of the clamp loader (gamma complex) *E. coli* DNA polymerase III holoenzyme is also identified. The presence of this gene confirms the presence of a clamp loading apparatus in Gram positive bacteria that will assemble beta clamps onto DNA for the DNA polymerases.

A new gene sequence encoding a DNA polymerase homologous to the alpha subunit of DNA polymerase III holoenzyme of *E. coli* (referred to herein as dnaE homolog) is also identified.

Also identified is a new gene sequence encoding a homolog of the replicative dnaB helicase of *E. coli*.

This application also outlines methods and assays for use of these replication proteins in drug screening processes.

BRIEF DESCRIPTION OF THE DRAWINGS

FIG. 2A compares *E. coli* cells that contain the pET11PolC expression vector that are either induced or uninduced for protein expression. The gel is stained with Coomassie Blue. The induced band corresponds to the expected molecular weight of the *S. aureus* Pol III-L, and is indicated to the right of the gel. FIG. 2B shows the results of the MonoQ chromatography of a lysate of *E. coli* (pET11PolC-L) induced for Pol III-L. The fractions were analyzed in a Coomassie Blue stained gel (top) and for DNA synthesis (bottom). Fractions containing Pol III-L are indicated. In FIG. 2C, fractions containing Pol III-L from the MonoQ column were pooled and chromatographed on a phosphocellulose column. This shows an analysis of the column fractions from the phosphocellulose column in a Coomassie Blue stained polyacrylamide gel. The position of Pol III-L is indicated to the right.

FIG. 4A compares *E. coli* cells that contain the pET16beta expression vector that are either induced or uninduced for protein expression. The gel is stained with Coomassie Blue. The induced band corresponds to the expected molecular weight of the *S. aureus* beta, and is indicated to the right of the gel. The migration position of size standards are indicated to the left. FIG. 4B shows the results of MonoQ chromatography of an *E. coli* (pET16beta) lysate induced for beta. The fractions were analyzed in a Coomassie Blue stained gel, and fractions containing beta are indicated. In FIG. 4C, fractions containing beta from the MonoQ column were pooled and chromatographed on a phosphocellulose column. This shows an analysis of the column fractions from the phosphocellulose column in a Coomassie Blue stained polyacrylamide gel. The position of beta is indicated to the right.

In FIG. 5A, the indicated proteins were added to replication reactions containing polydA-oligodT as described in the Examples supra. Amounts of proteins added, when present, were: lanes 1,2: *S. aureus* Pol III-L, 7.5 ng; *S. aureus* b, 6.2 ug; Lanes 3,4: *E. coli* Pol III core, 45 ng; *S. aureus* b, 9.3 ug; Lanes 5,6: *E. coli* Pol III core, 45 ng; *E. coli* b, 5 µg. Total DNA synthesis was: Lanes 1-6: 4.4, 30.3, 5.1, 35.5, 0.97, 28.1 pmol, respectively. In FIG. 5B, Lanes 1-3, the indicated proteins were added to replication reactions containing circular singly primed M13mp18 ssDNA as described in the Example supra. *S. aureus* b, 0.8 ug; *S. aureus* Pol III-L, 300 ng (purified through MonoQ); *E. coli* gamma complex, 1.7 µg. Results in the *E. coli* system are shown in Lanes 4-6. Total DNA synthesis was: Lanes 1-6: 0.6, 0.36, 0.99, 2.7, 3.5, 280 pmol, respectively.

FIG. 8A shows the product analysis in an agarose gel. FIG. 8B shows the extent of DNA synthesis in each assay.

FIG. 9 compares the homology between the polypeptide encoded by dnaE of *S. aureus* and other organisms. An alignment is shown for the amino acid sequence of the *S. aureus* dnaE product with the dnaE products (alpha subunits) of *E. coli* and *Salmonella typhimurium*.

FIG. 10 compares the homology between the N-terminal regions of the gamma/tau polypeptides of *S. aureus*, *B. subtilis*, and *E. coli*. The conserved ATP site and the cystines forming the zinc finger are indicated above the sequence. The organisms used in the alignment were: *E. coli* (GenBank); and *B. subtilis*.

FIG. 11 compares the homology between the DnaB polypeptide of *S. aureus* and other organisms. The organisms used in the alignment were: *E. coli* (GenBank); *B. subtilis*; Sal. Typ., (*Salmonella typhimurium*).

DETAILED DESCRIPTION OF THE INVENTION

Figure 1:
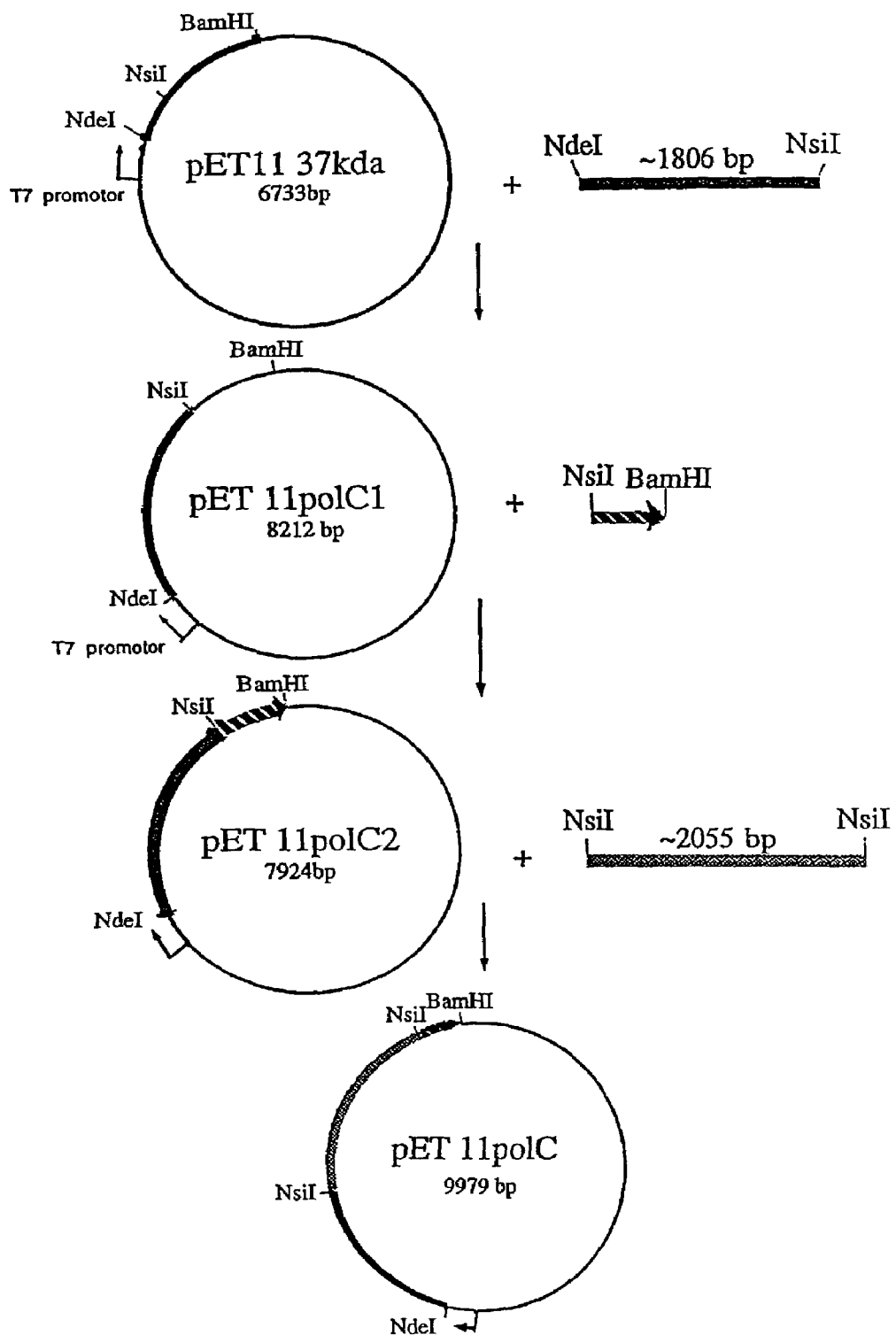
FIG. 1 shows the construction of the *S. aureus* Pol III-L expression vector. The gene encoding Pol III-L was cloned into a pET11 expression vector in a three step cloning scheme as illustrated.

The present invention relates to various isolated DNA molecules from Gram positive bacteria. These include dnaE, dnaX, dnaB, PolC, dnaN, and dnaG DNA molecules from Gram positive bacteria. These DNA molecules can be inserted into an expression system or used to transform host cells. The isolated proteins encoded by these DNA molecules are also disclosed.

These DNA molecules and proteins can be derived from any Gram positive bacteria, including Staphylococcus, Streptococcus, Enterococcus, and Mycobacterium. It is particularly directed to such DNA molecules and proteins derived from Staphylococcus bacteria, particularly *Staphylococcus aureus*.

One aspect of the present invention relates to a newly discovered Pol III gene of *S. aureus* cells (herein identified as dnaE) that is homologous to *E. coli* alpha (product of dnaE gene). The partial DNA sequence of the *S. aureus* dnaE gene is as follows (SEQ. ID. No. 1):

```
GATATAGATA TGGACTGGGA AGATACACGC CGAGAAAAGG TCATTCAGTA CGTCCAAGAA    60
AAATATGGCG AGCTACATGT ATCTGGAATT GTGACTTTCG GTCATCTGCT TGCAAAAGCG   120
GTTGCTAAAG ATGTTGGACG AATTATGGGG TTTGATGAAG TTACATTAAA TGAAATTTCA   180
AGTTTAATCC CACATAAATT AGGAATTACA CTTGATGAAG CATATCAAAT TGACGATTTT   240
AAAAAGTTTG TACATCGAAA CCATCGACAT CAACGCTGGT TCAGTATTTG TAAAAAGTTA   300
GAAGGTTTAC CAAGACATAC ATCTACACAT GCGGCAGGAA TTATTATTAA TGACCATCCA   360
TTATATGAAT ATGCCCCTTT AACGAAAGGG GATACAGGAT TATTAACGCA ATGGACAATG   420
ACTGAAGCCG AACGTATTGG TTTATTAAAA ATAGATTTTC TAGGGTTACG AAATTTATCA   480
ATTATCCATC AAATTTTGAC TCGAGTCGAA AAAGATTTAG GTTTTAATAT TGATATTGAA   540
AAAATTCCAT TTGATGATCA AAAGTGTTT GAATTGTTGT CGCAAGGAGA TACGACTGGC   600
ATATTTCAAT TAGAGTCTGA CGGTGTTAGA AGTGTATTAA AAAAATTAAA GCCGGAACAC   660
TTTGAGGATA TTGTTGCTGT AACTTCTTTG TATAGACCAG GTCCAATGGA AGAAATTCCA   720
ACTTACATTA CAAGAAGACA TGATCCAAGC AAAGTTCAAT ATTTACATCC CCATTTAGAA   780
CCTATATTAA AAAATACTTA CGGTGTTATT ATTTATCAAG AACAAATTAT GCAAATAGCG   840
AGCACTTTTG CAAACTTCAG TTATGGTGAA GCGGATATTT TAAGAAGAGC AATGAGTAAA   900
AAAAATAGAG CTGTTCTTGA AGAGACGCT CAACATTTTA TAGAAGGTAC AAAGCAAAAT   960
GGTTATCACG AAGACTTAGT AAGTAAGCAG ATATTTGATT TGATTCTGAA ATTTGCTGAT  1020
GATGGATTTC CTAGAGCACA TGCTGTCAGC TATTCTAAAA TTGCATACAT TATGAGCTTT  1080
TTAAAAGTCC ATTATCCAAA TTATTTTTAC GCAAATATTT TAAGTAATGT TATTGGAAGT  1140
GAGAAGAAAA CTGCTCAAAT GATAGAAGAA GCAAAAAAAC AAGGTATCAC TATATTGCCA  1200
CCGAACATTA ACGAAAGTCA TTGGTTTTAT AAACCTTCCC AAGAAGGCAT TTATTTATCA  1260
ATTGGTACAA TTAAAGGTGT AGGTTATCAA AGTGTGAAAG TGATTGTTGA AGAACGTTTT  1320
CAGAACGGCA AATTTAAAGA TTTCTTTGAT TCTGCTAGAC GTATACCGAA GAGAGTCAAA  1380
ACGAGAAAGT TACTTGAAGC ATTGATTTTA GTGGGAGCGT TTGATGCTTT TGGTAAAACA  1440
CGTTCAACGT TGTTGCAAGC TATTGATCAA GTGTTGGATG GTGATTTAAA CATTGAACAA  1500
GATGGTTTTT TATTTGATAT TTTAACGCCA AAACAGATGT ATGAAGATAA AGAAGAATTG  1560
CCTGATGCAC TTATTAGTCA GTATGAAAAA GAATATTTAG GATTTTATGT TTCGCAACAC  1620
CCAGTAGATA AGAAGTTTGT TGCCAAACAA TATTTAACGA TATTTTCTTG CGAAAACGTT  1680
GCTAAAGATG TTCGACGAAT TATGGGGTTT GATGAAGTTA AACAAA             1726
```

The *S. aureus* dnaE encoded protein has a partial amino acid sequence as follows (SEQ. ID. No. 2):

```
Asp Ile Asp Met Asp Trp Glu Asp Thr Arg Arg Glu Lys Val Ile Gln
1               5                   10                  15

Tyr Val Gln Glu Lys Tyr Gly Glu Leu His Val Ser Gly Ile Val Thr
            20                  25                  30

Phe Gly His Leu Leu Ala Lys Ala Val Ala Lys Asp Val Gly Arg Ile
        35                  40                  45

Met Gly Phe Asp Glu Val Thr Leu Asn Glu Ile Ser Ser Leu Ile Pro
    50                  55                  60

His Lys Leu Gly Ile Thr Leu Asp Glu Ala Tyr Gln Ile Asp Asp Phe
65                  70                  75                  80
```

-continued

```
Lys Lys Phe Val His Arg Asn His Arg His Gln Arg Trp Phe Ser Ile
             85                  90                  95
Cys Lys Lys Leu Glu Gly Leu Pro Arg His Thr Ser Thr His Ala Ala
            100                 105                 110
Gly Ile Ile Ile Asn Asp His Pro Leu Tyr Glu Tyr Ala Pro Leu Thr
            115                 120                 125
Lys Gly Asp Thr Gly Leu Leu Thr Gln Trp Thr Met Thr Glu Ala Glu
130             135                 140
Arg Ile Gly Leu Leu Lys Ile Asp Phe Leu Gly Leu Arg Asn Leu Ser
145                 150                 155                 160
Ile Ile His Gln Ile Leu Thr Arg Val Glu Lys Asp Leu Gly Phe Asn
                165                 170                 175
Ile Asp Ile Glu Lys Ile Pro Phe Asp Asp Gln Lys Val Phe Glu Leu
            180                 185                 190
Leu Ser Gln Gly Asp Thr Thr Gly Ile Phe Gln Leu Glu Ser Asp Gly
                195                 200                 205
Val Arg Ser Val Leu Lys Lys Leu Lys Pro Glu His Phe Glu Asp Ile
            210                 215                 220
Val Ala Val Thr Ser Leu Tyr Arg Pro Gly Pro Met Glu Glu Ile Pro
225                 230                 235                 240
Thr Tyr Ile Thr Arg Arg His Asp Pro Ser Lys Val Gln Tyr Leu His
                245                 250                 255
Pro His Leu Glu Pro Ile Leu Lys Asn Thr Tyr Gly Val Ile Ile Tyr
            260                 265                 270
Gln Glu Gln Ile Met Gln Ile Ala Ser Thr Phe Ala Asn Phe Ser Tyr
                275                 280                 285
Gly Glu Ala Asp Ile Leu Arg Arg Ala Met Ser Lys Lys Asn Arg Ala
            290                 295                 300
Val Leu Glu Arg Asp Ala Gln His Phe Ile Glu Gly Thr Lys Gln Asn
305                 310                 315                 320
Gly Tyr His Glu Asp Ile Ser Lys Gln Ile Phe Asp Leu Ile Leu Lys
                325                 330                 335
Phe Ala Asp Gly Phe Pro Arg Ala His Ala Val Ser Tyr Ser Lys Ile
            340                 345                 350
Ala Tyr Ile Met Ser Phe Leu Lys Val His Tyr Pro Asn Tyr Phe Tyr
                355                 360                 365
Ala Asn Ile Leu Ser Asn Val Ile Gly Ser Glu Lys Lys Thr Ala Gln
            370                 375                 380
Met Ile Glu Glu Ala Lys Lys Gln Gly Ile Thr Ile Leu Pro Pro Asn
385                 390                 395                 400
Ile Asn Glu Ser His Trp Phe Tyr Lys Pro Ser Gln Glu Gly Ile Tyr
                405                 410                 415
Leu Ser Ile Gly Thr Ile Lys Gly Val Gly Tyr Gln Ser Val Lys Val
            420                 425                 430
Ile Val Glu Glu Arg Phe Gln Asn Gly Lys Phe Lys Asp Phe Phe Asp
            435                 440                 445
Ser Ala Arg Arg Ile Pro Lys Arg Val Lys Thr Arg Lys Leu Leu Glu
450                 455                 460
Ala Leu Ile Leu Val Gly Ala Phe Asp Ala Phe Gly Lys Thr Arg Ser
465                 470                 475                 480
Thr Leu Leu Gln Ala Ile Asp Gln Val Leu Asp Gly Asp Leu Asn Ile
                485                 490                 495
Glu Gln Asp Gly Phe Leu Phe Asp Ile Leu Thr Pro Lys Gln Met Tyr
            500                 505                 510
```

-continued

```
Glu Asp Lys Glu Glu Leu Pro Asp Ala Leu Ile Ser Gln Tyr Glu Lys
        515                 520                 525

Glu Tyr Leu Gly Phe Tyr Val Ser Gln His Pro Val Asp Lys Lys Phe
    530                 535                 540

Val Ala Lys Gln Tyr Leu Thr Ile Phe Ser Cys Glu Asn Val Ala Lys
545                 550                 555                 560

Asp Val Arg Arg Ile Met Gly Phe Asp Glu Val Lys Gln
                565                 570
```

The present invention also relates to the *S. aureus* dnaX gene. This *S. aureus* dnaX gene has a partial nucleotide sequence as follows (SEQ. ID. No. 3):

```
TTGAATTATC AAGCCTTATA TCGTATGTAC AGACCCCAAA GTTTCGAGGA TGTCGTCGGA    60
CAAGAACATG TCACGAAGAC ATTGCGCAAT GCGATTTCGA AAGAAAAACA GTCGCATGCA   120
TATATTTTTA GTGGTCCGAG AGGTACGGGG AAAACGAGTA TTGCCAAAGT GTTTGCTAAA   180
GCAATCAACT GTTTAAATAG CACTGATGGA GAACCTTGTA ATGAATGTCA TATTTGTAAA   240
GGCATTACGC AGGGGACTAA TTCAGATGTG ATAGAAATTG ATGCTGCTAG TAATAATGGC   300
GTTGATGAAA TAAGAAATAT TAGAGACAAA GTTAAATATG CACCAAGTGA ATCGAAATAT   360
AAAGTTTATA TTATAGATGA GGTGCACATG CTAACAACAG GTGCTTTTAA TGCCCTTTTA   420
AAGACGTTAG AAGAACCTCC AGCACACGCT ATTTTTATAT TGGCAACGAC AGAACCACAT   480
AAAATCCCTC CAACAATCAT TTCTAGGGCA CAACGTTTTG ATTTTAAAGC AATTAGCCTA   540
GATCAAATTG TTGAACGTTT AAAATTTGTA GCAGATGCAC AACAAATTGA ATGTGAAGAT   600
GAAGCCTTGG CATTTATCGC TAAAGCGTCT GAAGGGGGTA TGCGTGATGC ATTAAGTATT   660
ATGGATCAGG CTATTGCTTT CGGCGATGGC ACATTGACAT TACAAGATGC CCTAAATGTT   720
ACGGGTAGCG TTCATGATGA AGCGTTGGAT CACTTGTTTG ATGATATTGT ACAAGGTGAC   780
GTACAAGCAT CTTTTAAAAA ATACCATCAG TTTATAACAG AAGGTAAAGA AGTGAATCGC   840
CTAATAAATG ATATGATTTA TTTTGTCAGA GATACGATTA TGAATAAAAC ATCTGAGAAA   900
GATACTGAGT ATCGAGCACT GATGAACTTA GAATTAGATA TGTTATATCA AATGATTGAT   960
CTTATTAATG ATACATTAGT GTCGATTCGT TTTAGTGTGA ATCAAAACGT TCATTTTGAA  1020
GTATTGTTAG TAAAATTAGC TGAGCAGATT AAGGGTCAAC CACAAGTGAT TGCGAATGTA  1080
GCTGAACCAG CACAAATTGC TTCATCGCCA AACACAGATG TATTGTTGCA ACGTATGGAA  1140
CAGTTAGAGC AAGAACTAAA AACACTAAAA GCACAAGGAG TGAGTGTTGC TCCTACTCAA  1200
AAATCTTCGA AAAAGCCTGC GAGAGGTATA CAAAAATCTA AAAATGCATT TTCAATGCAA  1260
CAAATTGCAA AAGTGCTAGA TAAAGCGAAT AAGGCAGATA TCAAATTGTT GAAAGATCAT  1320
TGGCAAGAAG TGATTGACCA TGCCCAAAAC AATGATAAAA AATCACTCGT TAGTTTATTG  1380
CAAAATTCGG AACCTGTGGC GGCAAGTGAA GATCACGTCC TTGTGAAATT TGAGGAAGAG  1440
ATCCATTGTG AAATCGTCAA TAAAGACGAC GAGAAACGTA GTAGTATAGA AAGTGTTGTA  1500
TGTAATATCG TTAATAAAAA CGTTAAAGTT GTTGGTGTAC CATCAGATCA ATGGCAAAGA  1560
GTTCGAACGG AGTATTTACA AAATCGTAAA AACGAAGGCG ATGATATGCC AAAGCAACAA  1620
GCACAACAAA CAGATATTGC TCAAAAAGCA AAAGATCTTT TCGGTGAAGA AACTGTACAT  1680
GTGATAGATG AAGAGTGA                                                1698
```

The *S. aureus* dnaX protein (i.e. the gamma subunit/tau subunit) has a partial amino acid sequence as follows (SEQ. ID. No. 4):

```
Leu Asn Tyr Gln Ala Leu Tyr Arg Met Tyr Arg Pro Gln Ser Phe Glu
1               5                   10                  15

Asp Val Val Gly Gln Glu His Val Thr Lys Thr Leu Arg Asn Ala Ile
                20                  25                  30

Ser Lys Glu Lys Gln Ser His Ala Tyr Ile Phe Ser Gly Pro Arg Gly
                35                  40                  45

Thr Gly Lys Thr Ser Ile Ala Lys Val Phe Ala Lys Ala Ile Asn Cys
                50                  55                  60

Leu Asn Ser Thr Asp Gly Glu Pro Cys Asn Glu Cys His Ile Cys Lys
65                  70                  75                  80

Gly Ile Thr Gln Gly Thr Asn Ser Asp Val Ile Glu Ile Asp Ala Ala
                85                  90                  95

Ser Asn Asn Gly Val Asp Glu Ile Arg Asn Ile Arg Asp Lys Val Lys
                100                 105                 110

Tyr Ala Pro Ser Glu Ser Lys Tyr Lys Val Tyr Ile Ile Asp Glu Val
                115                 120                 125

His Met Leu Thr Thr Gly Ala Phe Asn Ala Leu Leu Lys Thr Leu Glu
            130                 135                 140

Glu Pro Pro Ala His Ala Ile Phe Ile Leu Ala Thr Thr Glu Pro His
145                 150                 155                 160

Lys Ile Pro Pro Thr Ile Ile Ser Arg Ala Gln Arg Phe Asp Phe Lys
                165                 170                 175

Ala Ile Ser Leu Asp Gln Ile Val Glu Arg Leu Lys Phe Val Ala Asp
                180                 185                 190

Ala Gln Gln Ile Glu Cys Glu Asp Glu Ala Leu Ala Phe Ile Ala Lys
                195                 200                 205

Ala Ser Glu Gly Gly Met Arg Asp Ala Leu Ser Ile Met Asp Gln Ala
                210                 215                 220

Ile Ala Phe Gly Asp Gly Thr Leu Thr Leu Gln Asp Ala Leu Asn Val
225                 230                 235                 240

Thr Gly Ser Val His Asp Glu Ala Leu Asp His Leu Phe Asp Asp Ile
                245                 250                 255

Val Gln Gly Asp Val Gln Ala Ser Phe Lys Lys Tyr His Gln Phe Ile
                260                 265                 270

Thr Glu Gly Lys Glu Val Asn Arg Leu Ile Asn Asp Met Ile Tyr Phe
                275                 280                 285

Val Arg Asp Thr Ile Met Asn Lys Thr Ser Glu Lys Asp Thr Glu Tyr
                290                 295                 300

Arg Ala Leu Met Asn Leu Glu Leu Asp Met Leu Tyr Gln Met Ile Asp
305                 310                 315                 320

Leu Ile Asn Asp Thr Leu Val Ser Ile Arg Phe Ser Val Asn Gln Asn
                325                 330                 335

Val His Phe Glu Val Leu Leu Val Lys Leu Ala Glu Gln Ile Lys Gly
                340                 345                 350

Gln Pro Gln Val Ile Ala Asn Val Ala Glu Pro Ala Gln Ile Ala Ser
                355                 360                 365

Ser Pro Asn Thr Asp Val Leu Leu Gln Arg Met Glu Gln Leu Glu Gln
                370                 375                 380

Glu Leu Lys Thr Leu Lys Ala Gln Gly Val Ser Val Ala Pro Thr Gln
385                 390                 395                 400
```

-continued

```
Lys Ser Ser Lys Lys Pro Ala Arg Gly Ile Gln Lys Ser Lys Asn Ala
            405                 410                 415
Phe Ser Met Gln Gln Ile Ala Lys Val Leu Asp Lys Ala Asn Lys Ala
        420                 425                 430
Asp Ile Lys Leu Leu Lys Asp His Trp Gln Glu Val Ile Asp His Ala
            435                 440                 445
Gln Asn Asn Asp Lys Lys Ser Leu Val Ser Leu Leu Gln Asn Ser Glu
        450                 455                 460
Pro Val Ala Ala Ser Glu Asp His Val Leu Val Lys Phe Glu Glu Glu
465                 470                 475                 480
Ile His Cys Glu Ile Val Asn Lys Asp Asp Glu Lys Arg Ser Ser Ile
            485                 490                 495
Glu Ser Val Val Cys Asn Ile Val Asn Lys Asn Val Lys Val Val Gly
                500                 505                 510
Val Pro Ser Asp Gln Trp Gln Arg Val Arg Thr Glu Tyr Leu Gln Asn
            515                 520                 525
Arg Lys Asn Glu Gly Asp Asp Met Pro Lys Gln Gln Ala Gln Gln Thr
        530                 535                 540
Asp Ile Ala Gln Lys Ala Lys Asp Leu Phe Gly Glu Glu Thr Val His
545                 550                 555                 560
Val Ile Asp Glu Glu Glx
                565
```

This invention also relates to the partial nucleotide sequence of the *S. aureus* dnaB gene as follows (SEQ. ID. No. 5):

```
ATGGATAGAA TGTATGAGCA AAATCAAATG CCGCATAACA ATGAAGCTGA ACAGTCTGTC    60
TTAGGTTCAA TTATTATAGA TCCAGAATTG ATTAATACTA CTCAGGAAGT TTTGCTTCCT   120
GAGTCGTTTT ATAGGGGTGC CCATCAACAT ATTTTCCGTG CAATGATGCA CTTAAATGAA   180
GATAATAAAG AAATTGATGT TGTAACATTG ATGGATCAAT TATCGACGGA AGGTACGTTG   240
AATGAAGCGG GTGGCCCGCA ATATCTTGCA GAGTTATCTA CAAATGTACC AACGACGCGA   300
AATGTTCAGT ATTATACTGA TATCGTTTCT AAGCATGCAT TAAAACGTAG ATTGATTCAA   360
ACTGCAGATA GTATTGCCAA TGATGGATAT AATGATGAAC TTGAACTAGA TGCGATTTTA   420
AGTGATGCAG AACGTCGAAT TTTAGAGCTA TCATCTTCTC GTGAAAGCGA TGGCTTTAAA   480
GACATTCGAG ACGTCTTAGG ACAAGTGTAT GAAACAGCTG AAGAGCTTGA TCAAAATAGT   540
GGTCAAACAC CAGGTATACC TACAGGATAT CGAGATTTAG ACCAAATGAC AGCAGGGTTC   600
AACCGAAATG ATTTAATTAT CCTTGCAGCG CGTCCATCTG TAGGTAAGAC TGCGTTCGCA   660
CTTAATATTG CACAAAAAGT TGCAACGCAT GAAGATATGT ATACAGTTAA AGCAACAGG   720
AAGTTTCTGA AATCTCTCGT ACATTAAAAG CATTAGCCCG TGAATTAAAA TGTCCAGTTA   780
TCGCATTAAG TCAGTTATCT CGTGGTGTTG AACAACGACA AGATAAACGT CCAATGATGA   840
GTGATATTCG TGAATCTGGT TCGATTGAGC AAGATGCCGA TATCGTTGCA TTCTTATACC   900
GTGATGATTA CTATAACCGT GGCGGCGATG AAGATGATGA CGATGATGGT GGTTTCGAGC   960
CACAAACGAA TGATGAAAAC GGTGAAATTG AAATTATCAT TGTTAAGCAA CGTAACGGTC  1020
CAACAGGCAC AGTTAAGTTA CATTTTATGA ACAATATAA TAAATTTTAG AGCTATCATC  1080
TTTTCGTGAA AGCGATGGCT TTAAAGACAT TCGAGACGTC TTAGGACAAG TGTATGAAAC  1140
AGCTGAAGAG CTTGATCAAA ATAGTGGTGA ACACCAGGT ATACCTACAG GATATCGAGA  1200
```

-continued

```
TTTAGACCAA ATGACAGGAG GGTTCAACCG AAATGATTTA ATTATCCTTG CAGCGCGTCC  1260

ATCTGTAGGT AAGACTGCGT TCGCACTTAA TATTGCACAA AAAGTTGCAA CGCATCCGCA  1320

CTTAATATTG CCAATAAGTT GGAACGCATG AAGATATATC TAGCAGTTGG TATTTTCTCA  1380

CTAGAGATGG GTGCTGATCA GTTAACCACA CGTATGATTT GTAGTTCTGG TAATGTTGAC  1440

TCAAACCGCT TAAGAACCGG TACTATGACT GAGGAAGATT GGAGTCGTTT TACTATAGCG  1500

GTTGGTAAAT TATCACGTAC GAAGATTTTT ATTGATGATA CACCGGGTAT TCGAATTAAT  1560

GATTTACGTT CTAAATGTCG TCGATTAAAG CAAGAACATG GCTTAGACAT GATTGTGATT  1620

GACTACTTAC AGTTGATTCA AGGTAGTGGT TCACGTGCGT CCGATAACAG ACAACAGGAA  1680

GTTTCTGAAA TCTCTCGTAC ATTAAAAGCA TTAGCCCGTG AATTAAAATG TCCAGTTATC  1740

GCATTAAGTC AGTTATCTCG TGGTGTTGAA CAACGACAAG ATAAACGTCC AATGATGAGT  1800

GATATTCGTG AATCTGGTTC GATTGAGCAA GATGCCGATA TCGTTGCATT CTTATACCGT  1860

GATGATTACT ATAACCGTGG CGGCGATGAA GATGATGACG ATGATGGTGG TTTCGAGCCC  1920

CAAACGAATG ATGAAAACGG TGAAATTGAA ATTATCATTG CTAAGCAACG TTACGGTCCA  1980

ACAGGCACAG TTAAGTTACT TTTTATGAAA CAATATGGTA AATTTACCGA TATC        2034
```

The amino acid sequence of *S. aureus* DnaB encoded by the dnaB gene is as follows (SEQ. ID. No. 6):

```
Met Asp Arg Met Tyr Glu Gln Asn Gln Met Pro His Asn Asn Glu Ala
1               5                   10                  15

Glu Gln Ser Val Leu Gly Ser Ile Ile Ile Asp Pro Glu Leu Ile Asn
            20                  25                  30

Thr Thr Gln Glu Val Leu Leu Pro Glu Ser Phe Tyr Arg Gly Ala His
            35                  40                  45

Gln His Ile Phe Arg Ala Met Met His Leu Asn Glu Asp Asn Lys Glu
        50                  55                  60

Ile Asp Val Val Thr Leu Met Asp Gln Leu Ser Thr Glu Gly Thr Leu
65                  70                  75                  80

Asn Glu Ala Gly Gly Pro Gln Tyr Leu Ala Glu Leu Ser Thr Asn Val
                85                  90                  95

Pro Thr Thr Arg Asn Val Gln Tyr Tyr Thr Asp Ile Val Ser Lys His
            100                 105                 110

Ala Leu Lys Arg Arg Leu Ile Gln Thr Ala Asp Ser Ile Ala Asn Asp
            115                 120                 125

Gly Tyr Asn Asp Glu Leu Glu Leu Asp Ala Ile Leu Ser Asp Ala Glu
        130                 135                 140

Arg Arg Ile Leu Glu Leu Ser Ser Ser Arg Glu Ser Asp Gly Phe Lys
145                 150                 155                 160

Asp Ile Arg Asp Val Leu Gly Gln Val Tyr Glu Thr Ala Glu Glu Leu
                165                 170                 175

Asp Gln Asn Ser Gly Gln Thr Pro Gly Ile Pro Thr Gly Tyr Arg Asp
            180                 185                 190

Leu Asp Gln Met Thr Ala Gly Phe Asn Arg Asn Asp Leu Ile Ile Leu
        195                 200                 205

Ala Ala Arg Pro Ser Val Gly Lys Thr Ala Phe Ala Leu Asn Ile Ala
        210                 215                 220

Gln Lys Leu Glu Arg Met Lys Ile Tyr Leu Ala Val Gly Ile Phe Ser
225                 230                 235                 240
```

```
Leu Glu Met Gly Ala Asp Gln Leu Thr Thr Arg Met Ile Cys Ser Ser
            245                 250                 255
Gly Asn Val Asp Ser Asn Arg Leu Arg Thr Gly Thr Met Thr Glu Glu
            260                 265                 270
Asp Trp Ser Arg Phe Thr Ile Ala Val Gly Lys Leu Ser Arg Thr Lys
            275                 280                 285
Ile Phe Ile Asp Asp Thr Pro Gly Ile Arg Ile Asn Asp Leu Arg Ser
            290                 295                 300
Lys Cys Arg Arg Leu Lys Gln Glu His Gly Leu Asp Met Ile Val Ile
305                 310                 315                 320
Asp Tyr Leu Gln Leu Ile Gln Gly Ser Gly Ser Arg Ala Ser Asp Asn
                    325                 330                 335
Arg Gln Gln Glu Val Ser Glu Ile Ser Arg Thr Leu Lys Ala Leu Ala
                340                 345                 350
Arg Glu Leu Lys Cys Pro Val Ile Ala Leu Ser Gln Leu Ser Arg Gly
            355                 360                 365
Val Glu Gln Arg Gln Asp Lys Arg Pro Met Met Ser Asp Ile Arg Glu
            370                 375                 380
Ser Gly Ser Ile Glu Gln Asp Ala Asp Ile Val Ala Phe Leu Tyr Arg
385                 390                 395                 400
Asp Asp Tyr Tyr Asn Arg Gly Gly Asp Glu Asp Asp Asp Asp Asp Gly
                    405                 410                 415
Gly Phe Glu Pro Gln Thr Asn Asp Glu Asn Gly Glu Ile Glu Ile Ile
                420                 425                 430
Ile Ala Lys Gln Arg Tyr Gly Pro Gly Thr Val Lys Leu Leu Phe Met
            435                 440                 445
Lys Gln Tyr Gly Lys Phe Thr Asp Ile
    450                 455
```

The present invention also uses the gene sequence of *S. aureus* PolC (encoding Pol III-L). The nucleotide sequence is as follows (SEQ. ID. No. 7):

```
ATGACAGAGC AACAAAAATT TAAAGTGCTT GCTGATCAAA TTAAAATTTC AAATCAATTA    60
GATGCTGAAA TTTTAAATTC ACGTGAACTG ACACGTATAG ATGTTTCTAA CAAAAACAGA   120
ACATGGCAAT TCATATTAC ATTACCACAA TTCTTAGCTC ATGAAGATTA TTTATTATTT    180
ATAAATGCAA TAGAGCAAGA GTTTAAAGAT ATCGCCAACG TTACATGTCG TTTTACGGTA   240
ACAAATGGCA CGAATCAAGA TGAACATGCA ATTAAATACT TGGGCACTG  TATTGACCAA   300
ACAGCTTTAT CTCCAAAAGT TAAAGGTCAA TTGAAACAGA AAAGCTTAT  TATGTCTGGA   360
AAAGTATTAA AGTAATGGT ATCAAATGAC ATTGAACGTA ATCATTTGA  TAAGGCATGT   420
AATGGAAGTC TTATCAAAGC GTTAGAAAT  TGTGGTTTTG ATATCGATAA AATCATATTC   480
GAAACAAATG ATAATGATCA AGAACAAAAC TTAGCTTCTT TAGAAGCACA TATTCAAGAA   540
GAAGACGAAC AAAGTGCACG ATTGGCAACA GAGAAACTTG AAAAAATGAA AGCTGAAAAA   600
GCGAAACAAC AAGATAACAA GCAAAGTGCT GTCGATAAGT GTCAAATTGG TAAGCCGATT   660
CAAATTGAAA ATATTAAACC AATTGAATCT ATTATTGAGG AAGAGTTTAA AGTTGCAATA   720
GAGGGTGTCA TTTTTGATAT AAACTTAAAA GAACTTAAAA GTGGTCGCCA TATCGTAGAA   780
ATTAAAGTGA CTGACTATAC GGACTCTTTA GTTTTAAAAA TGTTTACTCG TAAAAACAAA   840
GATGATTTAG AACATTTTAA AGCGCTAAGT GTTGGTAAAT GGGTTAGGGC TCAAGGTCGT   900
```

-continued

```
ATTGAAGAAG ATACATTTAT TAGAGATTTA GTTATGATGA TGTCTGATAT TGAAGAGATT    960
AAAAAAGCGA CAAAAAAGA TAAGGCTGAA GAAAAGCGAG TAGAATTCCA CTTGCATACT    1020
GCAATGAGCC AAATGGATGG TATACCCAAT ATTGGTGCGT ATGTTAAACA GGCAGCAGAC   1080
TGGGGACATC CAGCCATTGC GGTTACAGAC CATAATGTGG TGCAAGCATT TCCAGATGCT   1140
CACGCAGCAG CGGAAAAACA TGGCATTAAA ATGATATACG GTATGGAAGG TATGTTAGTT   1200
GATGATGGTG TTCCGATTGC ATACAAACCA CAAGATGTCG TATTAAAAGA TGCTACTTAT   1260
GTTGTGTTCG ACGTTGAGAC AACTGGTTTA TCAAATCAGT ATGATAAAAT CATCGAGCTT   1320
GCAGCTGTGA AGTTCATAA CGGTGAAATC ATCGATAAGT TTGAAAGGTT TAGTAATCCG    1380
CATGAACGAT TATCGGAAAC GATTATCAAT TTGACGCATA TTACTGATGA TATGTTAGTA   1440
GATGCCCCTG AGATTGAAGA AGTACTTACA GAGTTTAAAG AATGGGTTGG CGATGCGATA   1500
TTCGTAGCGC ATAATGCTTC GTTTGATATG GGCTTCATCG ATACGGGATA TGAACGTCTT   1560
GGGTTTGGAC CATCAACGAA TGGTGTTATC GATACTTTAG AATTATCTCG TACGATTAAT   1620
ACTGAATATG GTAAACATGG TTTGAATTTC TTGGCTAAAA AATATGGCGT AGAATTAACG   1680
CAACATCACC GTGCCATTTA TGATACAGAA GCAACAGCTT ACATTTTCAT AAAAATGGTT   1740
CAACAAATGA AGAATTAGG CGTATTAAAT CATAACGAAA TCAACAAAAA ACTCAGTAAT    1800
GAAGATGCAT ATAAACGTGC AAGACCTAGT CATGTCACAT TAATTGTACA AAACCAACAA   1860
GGTCTTAAAA ATCTATTTAA AATTGTAAGT GCATCATTGG TGAAGTATTT CTACCGTACA   1920
CCTCGAATTC CACGTTCATT GTTAGATGAA TATCGTGAGG GATTATTGGT AGGTACAGCG   1980
TGTGATGAAG GTGAATTATT TACGGCAGTT ATGCAGAAGG ACCAGAGTCA AGTTGAAAAA   2040
ATTGCCAAAT ATTATGATTT TATTGAAATT CAACCACCGG CACTTTATCA AGATTTAATT   2100
GATAGAGAGC TTATTAGAGA TACTGAAACA TTACATGAAA TTTATCAACG TTTAATACAT   2160
GCAGGTGACA CAGCGGGTAT ACCTGTTATT GCGACAGGAA ATGCACACTA TTTGTTTGAA   2220
CATGATGGTA TCGCACGTAA AATTTTAATA GCATCACAAC CCGGCAATCC ACTTAATCGC   2280
TCAACTTTAC CGGAAGCACA TTTTAGAACT ACAGATGAAA TGTTAAACGA GTTTCATTTT   2340
TTAGGTGAAG AAAAAGCGCA TGAAATTGTT GTGAAAAATA CAAACGAATT AGCAGATCGA   2400
ATTGAACGTG TTGTTCCTAT TAAAGATGAA TTATACACAC CGCGTATGGA AGGTGCTAAC   2460
GAAGAAATTA GAGAACTAAG TTATGCAAAT GCGCGTAAAC TGTATGGTGA AGACCTGCCT   2520
CAAATCGTAA TTGATCGATT AGAAAAAGAA TTAAAAAGTA TTATCGGTAA TGGATTTGCG   2580
GTAATTTACT TAATTTCGCA ACGTTTAGTT AAAAAATCAT TAGATGATGG ATACTTAGTT   2640
GGTTCCCGTG GTTCAGTAGG TTCTAGTTTT GTAGCGACAA TGACTGAGAT TACTGAAGTA   2700
AACCCGTTAC CGCCACACTA TATTTGTCCG AACTGTAAAA CGAGTGAATT TTTCAATGAT   2760
GGTTCAGTAG GATCAGGATT TGATTTACCT GATAAGACGT GTGAAACTTG TGGAGCGCCA   2820
CTTATTAAAG AAGGACAAGA TATTCCGTTT GAAAAATTTT TAGGATTTAA GGGAGATAAA   2880
GTTCCTGATA TCGACTTAAA CTTTAGTGGT GAATATCAAC CGAATGCCCA TAACTACACA   2940
AAAGTATTAT TTGGTGAGGA TAAAGTATTC CGTGCAGGTA CAATTGGTAC TGTTGCTGAA   3000
AAGACTGCTT TTGGTTATGT TAAAGGTTAT TTGAATGATC AAGGTATCCA CAAAAGAGGT   3060
GCTGAAATAG ATCGACTCGT TAAAGGATGT ACAGGTGTAC CTGATTACAT GGATATTTAT   3120
GATTTTACGC CGATACAATA TCCTGCCGAT GATCAAAATT CAGCATGGAT GACGACACAT   3180
TTTGATTTCC ATTCTATTCA TGATAATGTA TTAAAACTTG ATATACTTGG ACACGATGAT   3240
CCAACAATGA TTCGTATGCT TCAAGATTTA TCAGCAATTG ATCCAAAAAC AATACCTGTA   3300
```

-continued

```
GATGATAAAG AAGTTATGCA GATATTTAGT ACACCTGAAA GTTTGGGTCT TACTGAAGAT  3360
GAAATTTTAT GTAAAACAGG TACATTTGGG GTACCGAATT CGGACAGGAT TCGTCGTCAA  3420
ATGTTAGAAG ATACAAAGCC AACAACATTT TCTGAATTAG TTCAAATCTC AGGATTATCT  3480
CATGGTACAG ATGTGTGGTT AGGCAATGCT CAAGAATTAA TTAAAACCGG TATATGTGAT  3540
TTATCAAGTG TAATTGGTTG TCGTGATGAT ATCATGGTTT ATTTAATGTA TGCTGGTTTA  3600
GAACCATCAA TGGCTTTTAA AATAATGGAG TCAGTACGTA AAGGTAAAGG TTTAACTGAA  3660
GAAATGATTG AAACGATGAA AGAAAATGAA GTGCCAGATT GGTATTTAGA TTCATGTCTT  3720
AAAATTAAGT ACATATTCCC TAAAGCCCAT GCAGCAGCAT ACGTTTTAAT GGCAGTACGT  3780
ATCGCATATT TCAAAGTACA TCATCCACTT TATTACTATG CATCTTACTT TACAATTCGT  3840
GCGTCAGACT TTGATTTAAT CACGATGATT AAAGATAAAA CAAGCATTCG AAATACTGTA  3900
AAAGACATGT ATTCTCGCTA TATGGATCTA GGTAAAAAAG AAAAAGACGT ATTAACAGTC  3960
TTGGAAATTA TGAATGAAAT GGCGCATCGA GGTTATCGAA TGCAACCGAT TAGTTTAGAA  4020
AAGAGTCAGG CGTTCGAATT TATCATTGAA GGCGATACAC TTATTCCGCC GTTCATATCA  4080
GTGCCTGGGC TTGGCGAAAA CGTTGCGAAA CGAATTGTTG AAGCTCGTGA CGATGGCCCA  4140
TTTTTATCAA AGAAGATTT  AAACAAAAAA GCTGGATTAT ATCAGAAAAT TATTGAGTAT  4200
TTAGATGAGT TAGGCTCATT ACCGAATTTA CCAGATAAAG CTCAACTTTC GATATTTGAT  4260
ATGTAA                                                             4266
```

The amino acid sequence of the *S. aureus* PolC gene product, Pol III-L is as follows (SEQ. ID. No. 8):

```
Met Thr Glu Gln Gln Lys Phe Lys Val Leu Ala Asp Gln Ile Lys Ile
1               5                   10                  15

Ser Asn Gln Leu Asp Ala Glu Ile Leu Asn Ser Gly Glu Leu Thr Arg
                20                  25                  30

Ile Asp Val Ser Asn Lys Asn Arg Thr Trp Glu Phe His Ile Thr Leu
            35                  40                  45

Pro Gln Phe Leu Ala His Glu Asp Tyr Leu Leu Phe Ile Asn Ala Ile
        50                  55                  60

Glu Gln Glu Phe Lys Asp Ile Ala Asn Val Thr Cys Arg Phe Thr Val
65                  70                  75                  80

Thr Asn Gly Thr Asn Gln Asp Glu His Ala Ile Lys Tyr Phe Gly His
                85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
        115                 120                 125

Asn Asp Ile Glu Arg Asn His Phe Asp Lys Ala Cys Asn Gly Ser Leu
130                 135                 140

Ile Lys Ala Phe Arg Asn Cys Gly Phe Asp Ile Asp Lys Ile Ile Phe
145                 150                 155                 160

Glu Thr Asn Asp Asn Asp Gln Glu Gln Asn Leu Ala Ser Leu Glu Ala
                165                 170                 175

His Ile Gln Glu Glu Asp Glu Gln Ser Ala Arg Leu Ala Thr Glu Lys
            180                 185                 190

Leu Glu Lys Met Lys Ala Glu Lys Ala Lys Gln Gln Asp Asn Lys Gln
        195                 200                 205
```

-continued

```
Ser Ala Val Asp Lys Cys Gln Ile Gly Lys Pro Ile Gln Ile Glu Asn
210                 215                 220
Ile Lys Pro Ile Glu Ser Ile Ile Glu Glu Phe Lys Val Ala Ile
225                 230                 235                 240
Glu Gly Val Ile Phe Asp Ile Asn Leu Lys Leu Lys Ser Gly Arg
                245                 250                 255
His Ile Val Glu Ile Lys Val Thr Asp Tyr Thr Asp Ser Leu Val Leu
                260                 265                 270
Lys Met Phe Thr Arg Lys Asn Lys Asp Asp Leu Glu His Phe Lys Ala
                275                 280                 285
Leu Ser Val Gly Lys Trp Val Arg Ala Gln Gly Arg Ile Glu Glu Asp
                290                 295                 300
Thr Phe Ile Arg Asp Leu Val Met Met Met Ser Asp Ile Glu Glu Ile
305                 310                 315                 320
Lys Lys Ala Thr Lys Lys Asp Lys Ala Glu Glu Lys Arg Val Glu Phe
                325                 330                 335
His Leu His Thr Ala Met Ser Gln Met Asp Gly Ile Pro Asn Ile Gly
                340                 345                 350
Ala Tyr Val Lys Gln Ala Ala Asp Trp Gly His Pro Ala Ile Ala Val
                355                 360                 365
Thr Asp His Asn Val Val Gln Ala Phe Pro Asp Ala His Ala Ala Ala
370                 375                 380
Glu Lys His Gly Ile Lys Met Ile Tyr Gly Met Glu Gly Met Leu Val
385                 390                 395                 400
Asp Asp Gly Val Pro Ile Ala Tyr Lys Pro Gln Asp Val Val Leu Lys
                405                 410                 415
Asp Ala Thr Tyr Val Val Phe Asp Val Glu Thr Thr Gly Leu Ser Asn
                420                 425                 430
Gln Tyr Asp Lys Ile Ile Glu Leu Ala Ala Val Lys Val His Asn Gly
                435                 440                 445
Glu Ile Ile Asp Lys Phe Glu Arg Phe Ser Asn Pro His Glu Arg Leu
                450                 455                 460
Ser Glu Thr Ile Ile Asn Leu Thr His Ile Thr Asp Asp Met Leu Val
465                 470                 475                 480
Asp Ala Pro Glu Ile Glu Glu Val Leu Thr Glu Phe Lys Glu Trp Val
                485                 490                 495
Gly Asp Ala Ile Phe Val Ala His Asn Ala Ser Phe Asp Met Gly Phe
                500                 505                 510
Ile Asp Thr Gly Tyr Glu Arg Leu Gly Phe Gly Pro Ser Thr Asn Gly
                515                 520                 525
Val Ile Asp Thr Leu Glu Leu Ser Arg Thr Ile Asn Thr Glu Tyr Gly
                530                 535                 540
Lys His Gly Leu Asn Phe Leu Ala Lys Lys Tyr Gly Val Glu Leu Thr
545                 550                 555                 560
Gln His His Arg Ala Ile Tyr Asp Thr Glu Ala Thr Ala Tyr Ile Phe
                565                 570                 575
Ile Lys Met Val Gln Gln Met Lys Glu Leu Gly Val Leu Asn His Asn
                580                 585                 590
Glu Ile Asn Lys Lys Leu Ser Asn Glu Asp Ala Tyr Lys Arg Ala Arg
                595                 600                 605
Pro Ser His Val Thr Leu Ile Val Gln Asn Gln Gln Gly Leu Lys Asn
                610                 615                 620
Leu Phe Lys Ile Val Ser Ala Ser Leu Val Lys Tyr Phe Tyr Arg Thr
```

-continued

```
        625                 630                 635                 640
Pro Arg Ile Pro Arg Ser Leu Leu Asp Glu Tyr Arg Glu Gly Leu Leu
                645                 650                 655
Val Gly Thr Ala Cys Asp Glu Gly Leu Phe Thr Ala Val Met Gln
                660                 665                 670
Lys Asp Gln Ser Gln Val Glu Lys Ile Ala Lys Tyr Asp Phe Ile
                675                 680                 685
Glu Ile Gln Pro Pro Ala Leu Tyr Gln Asp Leu Ile Asp Arg Glu Leu
                690                 695                 700
Ile Arg Asp Thr Glu Thr Leu His Glu Ile Tyr Gln Arg Leu Ile His
705                 710                 715                 720
Ala Gly Asp Thr Ala Gly Ile Pro Val Ile Ala Thr Gly Asn Ala His
                725                 730                 735
Tyr Leu Phe Glu His Asp Gly Ile Ala Arg Lys Ile Leu Ile Ala Ser
                740                 745                 750
Gln Pro Gly Asn Pro Leu Asn Arg Ser Thr Leu Pro Glu Ala His Phe
                755                 760                 765
Arg Thr Thr Asp Glu Met Leu Asn Glu Phe His Phe Leu Gly Glu Glu
            770                 775                 780
Lys Ala His Glu Ile Val Val Lys Asn Thr Asn Glu Leu Ala Asp Arg
785                 790                 795                 800
Ile Glu Arg Val Val Pro Ile Lys Asp Glu Leu Tyr Thr Pro Arg Met
                805                 810                 815
Glu Gly Ala Asn Glu Glu Ile Arg Glu Leu Ser Tyr Ala Asn Ala Arg
                820                 825                 830
Lys Leu Tyr Gly Glu Asp Leu Pro Gln Ile Val Ile Asp Arg Leu Glu
                835                 840                 845
Lys Glu Leu Lys Ser Ile Ile Gly Asn Gly Phe Ala Val Ile Tyr Leu
                850                 855                 860
Ile Ser Gln Arg Leu Val Lys Lys Ser Leu Asp Asp Gly Tyr Leu Val
865                 870                 875                 880
Gly Ser Arg Gly Ser Val Gly Ser Ser Phe Val Ala Thr Met Thr Glu
                885                 890                 895
Ile Thr Glu Val Asn Pro Leu Pro Pro His Tyr Ile Cys Pro Asn Cys
                900                 905                 910
Lys Thr Ser Glu Phe Phe Asn Asp Gly Ser Val Gly Ser Gly Phe Asp
                915                 920                 925
Leu Pro Asp Lys Thr Cys Glu Thr Cys Gly Ala Pro Leu Ile Lys Glu
                930                 935                 940
Gly Gln Asp Ile Pro Phe Glu Lys Phe Leu Gly Phe Lys Gly Asp Lys
945                 950                 955                 960
Val Pro Asp Ile Asp Leu Asn Phe Ser Gly Glu Tyr Gln Pro Asn Ala
                965                 970                 975
His Asn Tyr Thr Lys Val Leu Phe Gly Glu Asp Lys Val Phe Arg Ala
                980                 985                 990
Gly Thr Ile Gly Thr Val Ala Glu Lys Thr Ala Phe Gly Tyr Val Lys
                995                 1000                1005
Gly Tyr Leu Asn Asp Gln Gly Ile His Lys Arg Gly Ala Glu Ile Asp
            1010                1015                1020
Arg Leu Val Lys Gly Cys Thr Gly Val Arg Ala Thr Thr Gly Gln His
1025                1030                1035                1040
Pro Gly Gly Ile Ile Val Val Pro Asp Tyr Met Asp Ile Tyr Asp Phe
                1045                1050                1055
```

-continued

```
Thr Pro Ile Gln Tyr Pro Ala Asp Asp Gln Asn Ser Ala Trp Met Thr
            1060                1065                1070

Thr His Phe Asp Phe His Ser Ile His Asp Asn Val Leu Lys Leu Asp
        1075                1080                1085

Ile Leu Gly His Asp Asp Pro Thr Met Ile Arg Met Leu Gln Asp Leu
    1090                1095                1100

Ser Gly Ile Asp Pro Lys Thr Ile Pro Val Asp Lys Glu Val Met
1105                1110                1115                1120

Gln Ile Phe Ser Thr Pro Glu Ser Leu Gly Val Thr Glu Asp Glu Ile
                1125                1130                1135

Leu Cys Lys Thr Gly Thr Phe Gly Val Pro Asn Ser Asp Arg Ile Arg
            1140                1145                1150

Arg Gln Met Leu Glu Asp Thr Lys Pro Thr Thr Phe Ser Glu Leu Val
            1155                1160                1165

Gln Ile Ser Gly Leu Ser His Gly Thr Asp Val Trp Leu Gly Asn Ala
        1170                1175                1180

Gln Glu Leu Ile Lys Thr Gly Ile Cys Asp Leu Ser Ser Val Ile Gly
1185                1190                1195                1200

Cys Arg Asp Asp Ile Met Val Tyr Leu Met Tyr Ala Gly Leu Glu Pro
                1205                1210                1215

Ser Met Ala Phe Lys Ile Met Gln Ser Val Arg Lys Gly Lys Gly Leu
            1220                1225                1230

Thr Glu Glu Met Ile Glu Thr Met Lys Glu Asn Glu Val Pro Asp Trp
            1235                1240                1245

Tyr Leu Asp Ser Cys Leu Lys Ile Lys Tyr Ile Phe Pro Lys Ala His
        1250                1255                1260

Ala Ala Ala Tyr Val Leu Met Ala Val Arg Ile Ala Tyr Phe Lys Val
1265                1270                1275                1280

His His Pro Leu Tyr Tyr Tyr Ala Ser Tyr Phe Thr Ile Arg Ala Ser
                1285                1290                1295

Asp Phe Asp Leu Ile Thr Met Ile Lys Asp Lys Thr Ser Ile Arg Asn
            1300                1305                1310

Thr Val Lys Asp Met Tyr Ser Arg Tyr Met Asp Leu Gly Lys Lys Glu
            1315                1320                1325

Lys Asp Val Leu Thr Val Leu Glu Ile Met Asn Glu Met Ala His Arg
1330                1335                1340

Gly Tyr Arg Met Gln Pro Ile Ser Leu Glu Lys Ser Gln Ala Phe Glu
1345                1350                1355                1360

Phe Ile Ile Glu Gly Asp Thr Leu Ile Pro Pro Phe Ile Ser Val Pro
            1365                1370                1375

Gly Leu Gly Glu Asn Val Ala Lys Arg Ile Val Glu Ala Arg Asp Asp
            1380                1385                1390

Gly Pro Phe Leu Ser Lys Glu Asp Leu Asn Lys Lys Ala Gly Leu Tyr
        1395                1400                1405

Gln Lys Ile Ile Glu Tyr Leu Asp Glu Leu Gly Ser Leu Pro Asn Leu
    1410                1415                1420

Pro Asp Lys Ala Gln Leu Ser Ile Phe Asp Met
1425                1430                1435
```

This invention also relates to the sequence of the *S. aureus* dnaN gene encoding the beta subunit. The nucleotide sequence is as follows (SEQ. ID. No.9):

```
ATGATGGAAT TCACTATTAA AAGAGATTAT TTTATTACAC AATTAAATGA CACATTAAAA    60
GCTATTTCAC CAAGAACAAC ATTACCTATA TTAACTGGTA TCAAAATCGA TGCGAAAGAA   120
CATGAAGTTA TATTAACTGG TTCAGACTCT GAAATTTCAA TAGAAATCAC TATTCCTAAA   180
ACTGTAGATG GCGAAGATAT TGTCAATATT TCAGAAACAG GCTCAGTAGT ACTTCCTGGA   240
CGATTCTTTG TTGATATTAT AAAAAAATTA CCTGGTAAAG ATGTTAAATT ATCTACAAAT   300
GAACAATTCC AGACATTAAT TACATCAGGT CATTCTGAAT TTAATTTGAG TGGCTTAGAT   360
CCAGATCAAT ATCCTTTATT ACCTCAAGTT TCTAGAGATG ACGCAATTCA ATTGTCGGTA   420
AAAGTACTTA AAAACGTGAT TGCACAAACG AATTTTGCAG TGTCCACCTC AGAAACACGC   480
CCAGTACTAA CTGGTGTGAA CTGGCTTATA CAAGAAAATG AATTAATATG CACAGCGACT   540
GATTCACACC GCTTGGCTGT AAGAAAGTTG CAGTTAGAAG ATGTTTCTGA AACAAAAAT   600
GTCATCATTC CAGGTAAGGC TTTAGCTGAA TTAAATAAAA TTATGTCTGA CAATGAAGAA   660
GACATTGATA TCTTCTTTGC TTCAAACCAA GTTTTATTTA AAGTTGGAAA TGTGAACTTT   720
ATTTCTCGAT TATTAGAAGG ACATTATCCT GATACAACAC GTTTATTCCC TGAAAACTAT   780
GAAATTAAAT TAAGTATAGA CAATCGGGAG TTTTATCATG CGATTGATCG TGCCTCTTTA   840
TTAGCACGTG AAGGTGGTAA TAACGTTATT AAATTAAGTA CAGGTGATGA CGTTGTTGAA   900
TTATCTTCTA CATCACCAGA AATTGGTACT GTAAAAGAAG AAGTTGATGC AAACGATGTT   960
GAAGGTGGTA GCCTGAAAAT TCATTCAAC TCTAAATATA TGATGGATGC TTTAAAAGCA  1020
ATCGATAATG ATGAGGTTGA AGTTGAATTC TTCGGTACAA TGAAACCATT TATTCTAAAA  1080
CCAAAAGGTG ACGACTCGGT AACGCAATTA ATTTTACCAA TCAGAACTTA CTAA        1134
```

This amino acid sequence of *S. aureus* beta subunit is as follows (SEQ. ID. No. 10):

```
Met Met Glu Phe Thr Ile Lys Arg Asp Tyr Phe Ile Thr Gln Leu Asn
1               5                   10                  15

Asp Thr Leu Lys Ala Ile Ser Pro Arg Thr Thr Leu Pro Ile Leu Thr
            20                  25                  30

Gly Ile Lys Ile Asp Ala Lys Glu His Glu Val Ile Leu Thr Gly Ser
            35                  40                  45

Asp Ser Glu Ile Ser Ile Glu Ile Thr Ile Pro Lys Thr Val Asp Gly
    50                  55                  60

Glu Asp Ile Val Asn Ile Ser Glu Thr Gly Ser Val Val Leu Pro Gly
65                  70                  75                  80

Arg Phe Phe Val Asp Ile Ile Lys Lys Leu Pro Gly Lys Asp Val Lys
                85                  90                  95

Leu Ser Thr Asn Glu Gln Phe Gln Thr Leu Ile Thr Ser Gly His Ser
            100                 105                 110

Glu Phe Asn Leu Ser Gly Leu Asp Pro Asp Gln Tyr Pro Leu Leu Pro
            115                 120                 125

Gln Val Ser Arg Asp Asp Ala Ile Gln Leu Ser Val Lys Val Leu Lys
        130                 135                 140

Asn Val Ile Ala Gln Thr Asn Phe Ala Val Ser Thr Ser Glu Thr Arg
145                 150                 155                 160

Pro Val Leu Thr Gly Val Asn Trp Leu Ile Gln Glu Asn Glu Leu Ile
```

-continued

```
              165                 170                 175
Cys Thr Ala Thr Asp Ser His Arg Leu Ala Val Arg Lys Leu Gln Leu
            180                 185                 190
Glu Asp Val Ser Glu Asn Lys Asn Val Ile Ile Pro Gly Lys Ala Leu
            195                 200                 205
Ala Glu Leu Asn Lys Ile Met Ser Asp Asn Glu Glu Asp Ile Asp Ile
            210                 215                 220
Phe Phe Ala Ser Asn Gln Val Leu Phe Lys Val Gly Asn Val Asn Phe
225                 230                 235                 240
Ile Ser Arg Leu Leu Glu Gly His Tyr Pro Asp Thr Thr Arg Leu Phe
            245                 250                 255
Pro Glu Asn Tyr Glu Ile Lys Leu Ser Ile Asp Asn Gly Glu Phe Tyr
            260                 265                 270
His Ala Ile Asp Arg Ala Ser Leu Leu Ala Arg Glu Gly Gly Asn Asn
            275                 280                 285
Val Ile Lys Leu Ser Thr Gly Asp Asp Val Val Glu Leu Ser Ser Thr
            290                 295                 300
Ser Pro Glu Ile Gly Thr Val Lys Glu Glu Val Asp Ala Asn Asp Val
305                 310                 315                 320
Glu Gly Gly Ser Leu Lys Ile Ser Phe Asn Ser Lys Tyr Met Met Asp
                325                 330                 335
Ala Leu Lys Ala Ile Asp Asn Asp Glu Val Glu Val Gln Phe Phe Gly
            340                 345                 350
Thr Met Lys Pro Phe Ile Leu Lys Pro Lys Gly Asp Asp Ser Val Thr
            355                 360                 365
Gln Leu Ile Leu Pro Ile Arg Thr Tyr
    370                 375
                                                              35
```

This invention also relates to the sequence of the *S. aureus* dnaG gene encoding a primase. The nucleotide sequence is as follows (SEQ. ID. No. 11):

```
ATGATAGGTT TGTGTCCTTT TCATGATGAA AAGACACCTT CATTTACAGT TTCTGAAGAT    60

AAACAAATCT GTCATTGTTT TGGTTGTAAA AAAGGTGGCA ATGTTTTTCA ATTTACTCAA   120

GAAATTAAAG ACATATCATT TGTTGAAGCG GTTAAAGAAT TAGGTGATAG ACTTAATGTT   180

GCTGTAGATA TTGAGGCAAC ACAATCTAAC TCAAATGTTC AAATTGCTTC TGATGATTTA   240

CAAATGATTG AAATGCATGA GTTAATACAA GAATTTTATT ATTACGCTTT AACAAAGACA   300

GTCGAAGGCG AACAAGCATT AACATACTTA CAAGAACGTG GTTTTACAGA TGCGCTTATT   360

AAAGAGCGAG GCATTGGCTT TGCACCCGAT AGCTCACATT TTTGTCATGA TTTTCTTCAA   420

AAAAAGGGTT ACGATATTGA ATTAGCATAT GAAGCCGGAT TATTATCACG TAACGAAGAA   480

AATTTCAGTT ATTACGATAG ATTTCGAAAT CGTATTATGT TTCCTTTGAA AAATGCGCAA   540

GGAAGAATTG TTGGATATTC AGGTCGAACA TATACCGGTC AAGAACCAAA ATACCTAAAT   600

AGTCCTGAAA CGCCTATCTT TCAAAAAAGA AAGTTGTTAT ATAACTTAGA TAAAGCACGT   660

AAATCAATTA GAAATTAGA TGAAATTGTA TTACTAGAAG GTTTTATGGA TGTTATAAAA   720

TCTGATACTG CTGGCTTGAA AAACGTTGTT GCAACAATGG GTACACAGTT GTCAGATGAA   780

CATATTACCT TTATACGAAA GTTAACATCA AATATAACAT TAATGTTTGA TGGGGATTTT   840

GCGGGTAGTG AAGCAACACT TAAAACAGGT CAACATTTGT TACAGCAAGG GCTAAATGTA   900

TTTGTTATAC AATTGCCATC TGGCATGGAT CCGGATGAAT ACATTGGTAA GTATGGCAAC   960
```

-continued

```
GACGCATTTA CTACTTTTGT AAAAAATGAC AAAAAGTCAT TTGCACATTA TAAAGTAAGT 1020

ATATTAAAAG ATGAAATTGC ACATAATGAC CTTTCATATG AACGTTATTT GAAAGAACTG 1080

AGTCATGACA TTTCACTTAT GAAGTCATCA ATTCTGCAAC AAAAGGCTAT AAATGATGTT 1140

GCGCCATTTT TCAATGTTAG TCCTGAGCAG TTAGCTAACG AAATACAATT CAATCAAGCA 1200

CCAGCCAATT ATTATCCAGA AGATGAGTAT GGCGGTTATG ATGAGTATGG CGGTTATATT 1260

GAACCTGAGC CAATTGGTAT GGCACAATTT GACAATTTGA GCCGTCGAGA AAAAGCGGAG 1320

CGAGCATTTT TAAAACATTT AATGAGAGAT AAAGATACAT TTTTAAATTA TTATGAAAGT 1380

GTTGATAAGG ATAACTTCAC AAATCAGCAT TTTAAATATG TATTCGAAGT CTTACATGAT 1440

TTTTATGCGG AAAATGATCA ATATAATATC AGTGATGCTG TGCAGTATGT TAATTCAAAT 1500

GAGTTGAGAG AAACACTAAT TAGCTTAGAA CAATATAATT TGAATGGCGA ACCATATGAA 1560

AATGAAATTG ATGATTATGT CAATGTTATT AATGAAAAG GACAAGAAAC AATTGAGTCA 1620

TTGAATCATA AATTAAGGGA AGCTACAAGG ATTGGCGATG TAGAATTACA AAAATACTAT 1680

TTACAGCAAA TTGTTGCTAA GAATAAAGAA CGCATGTAG                        1719
```

The amino acid sequence of primase encoded by *S. aureus* dnaG is as follows (SEQ. ID. No. 12):

```
Met Ile Gly Leu Cys Pro Phe His Asp Glu Lys Thr Pro Ser Phe Thr
1               5                   10                  15

Val Ser Glu Asp Lys Gln Ile Cys His Cys Phe Gly Cys Lys Lys Gly
            20                  25                  30

Gly Asn Val Phe Gln Phe Thr Gln Glu Ile Lys Asp Ile Ser Phe Val
        35                  40                  45

Glu Ala Val Lys Glu Leu Gly Asp Arg Val Asn Val Ala Val Asp Ile
    50                  55                  60

Glu Ala Thr Gln Ser Asn Ser Asn Val Gln Ile Ala Ser Asp Asp Leu
65                  70                  75                  80

Gln Met Ile Glu Met His Glu Leu Ile Gln Glu Phe Tyr Tyr Tyr Ala
            85                  90                  95

Leu Thr Lys Thr Val Glu Gly Glu Gln Ala Leu Thr Tyr Leu Gln Glu
            100                 105                 110

Arg Gly Phe Thr Asp Ala Leu Ile Lys Glu Arg Gly Ile Gly Phe Ala
        115                 120                 125

Pro Asp Ser Ser His Phe Cys His Asp Phe Leu Gln Lys Lys Gly Tyr
    130                 135                 140

Asp Ile Glu Len Ala Tyr Glu Ala Gly Leu Leu Ser Arg Asn Glu Glu
145                 150                 155                 160

Asn Phe Ser Tyr Tyr Asp Arg Phe Arg Asn Arg Ile Met Phe Pro Leu
            165                 170                 175

Lys Asn Ala Gln Gly Arg Ile Val Gly Tyr Ser Gly Arg Thr Tyr Thr
            180                 185                 190

Gly Gln Glu Pro Lys Tyr Leu Asn Ser Pro Glu Thr Pro Ile Phe Gln
        195                 200                 205

Lys Arg Lys Leu Leu Tyr Asn Leu Asp Lys Ala Arg Lys Ser Ile Arg
    210                 215                 220

Lys Leu Asp Glu Ile Val Leu Leu Glu Gly Phe Met Asp Val Ile Lys
225                 230                 235                 240

Ser Asp Thr Ala Gly Leu Lys Asn Val Val Ala Thr Met Gly Thr Gln
```

-continued

```
            245                 250                 255
Leu Ser Asp Gln His Ile Thr Phe Ile Arg Lys Leu Thr Ser Asn Ile
            260                 265                 270

Thr Leu Met Phe Asp Gly Asp Phe Ala Gly Ser Glu Ala Thr Leu Lys
            275                 280                 285

Thr Gly Gln His Leu Leu Gln Gln Gly Leu Asn Val Phe Val Ile Gln
            290                 295                 300

Leu Pro Ser Gly Met Asp Pro Asp Glu Tyr Ile Gly Lys Tyr Gly Asn
305                 310                 315                 320

Asp Ala Phe Thr Thr Phe Val Lys Asn Asp Lys Lys Ser Phe Ala His
                325                 330                 335

Tyr Lys Val Ser Ile Leu Lys Asp Glu Ile Ala His Asn Asp Leu Ser
                340                 345                 350

Tyr Glu Arg Tyr Leu Lys Glu Leu Ser His Asp Ile Ser Leu Met Lys
                355                 360                 365

Ser Ser Ile Leu Gln Gln Lys Ala Ile Asn Asp Val Ala Pro Phe Phe
        370                 375                 380

Asn Val Ser Pro Glu Gln Leu Ala Asn Glu Ile Gln Phe Asn Gln Ala
385                 390                 395                 400

Pro Ala Asn Tyr Tyr Pro Glu Asp Glu Tyr Gly Gly Tyr Asp Glu Tyr
                405                 410                 415

Gly Gly Tyr Ile Glu Pro Glu Pro Ile Gly Met Ala Gln Phe Asp Asn
                420                 425                 430

Leu Ser Arg Arg Glu Lys Ala Glu Arg Ala Phe Leu Lys His Leu Met
                435                 440                 445

Arg Asp Lys Asp Thr Phe Leu Asn Tyr Tyr Glu Ser Val Asp Lys Asp
        450                 455                 460

Asn Phe Thr Asn Gln His Phe Lys Tyr Val Phe Glu Val Leu His Asp
465                 470                 475                 480

Phe Tyr Ala Glu Asn Asp Gln Tyr Asn Ile Ser Asp Ala Val Gln Tyr
                485                 490                 495

Val Asn Ser Asn Glu Leu Arg Glu Thr Leu Ile Ser Leu Glu Gln Tyr
                500                 505                 510

Asn Leu Asn Gly Glu Pro Tyr Glu Asn Glu Ile Asp Asp Tyr Val Asn
                515                 520                 525

Val Ile Asn Glu Lys Gly Gln Glu Thr Ile Glu Ser Leu Asn His Lys
            530                 535                 540

Leu Arg Glu Ala Thr Arg Ile Gly Asp Val Glu Leu Gln Lys Tyr Tyr
545                 550                 555                 560

Leu Gln Gln Ile Val Ala Lys Asn Lys Glu Arg Met
                565                 570
```

Fragments of the above polypeptides or proteins are also encompassed by the present invention.

Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for activity according to the procedures described below.

As an alternative, fragments of replication proteins can be produced by digestion of a full-length replication protein with proteolytic enzymes like chymotrypsin or Staphylococcus proteinase A, or trypsin. Different proteolytic enzymes are likely to cleave replication proteins at different sites based on the amino acid sequence of the protein. Some of the fragments that result from proteolysis may be active.

In another approach, based on knowledge of the primary structure of the protein, fragments of a replication protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences of replication proteins being produced. Alternatively, subjecting a full length replication protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which cotranslationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of 50 continuous bases of SEQ. ID. Nos. 1, 3, 5, 7, 9, or 11 under stringent conditions such as those characterized by a hybridization buffer comprising 0.9M sodium citrate ("SSC") buffer at a temperature of 37° C. and remaining bound when subject to washing the SSC buffer at a temperature of 37° C.; and preferably in a hybridization buffer comprising 20% formamide in 0.9M SSC buffer at a temperature of 42° C. and remaining bound when subject to washing at 42° C. with 0.2×SSC buffer at 42° C.

The proteins or polypeptides of the present invention are preferably produced in purified form (preferably at least 80%, more preferably 90%, pure) by conventional techniques. Typically, the proteins or polypeptides of the present invention is secreted into the growth medium of recombinant host cells. Alternatively, the proteins or polypeptides of the present invention are produced but not secreted into growth medium. In such cases, to isolate the protein, the host cell (e.g., E. coli) carrying a recombinant plasmid is propagated, lysed by sonication, heat, or chemical treatment, and the homogenate is centrifuged to remove bacterial debris. The supernatant is then subjected to purification procedures such as ammonium sulfate precipitation, gel filtration, ion exchange chromatography, FPLC, and HPLC.

The DNA molecule encoding replication polypeptides or proteins derived from Gram positive bacteria can be incorporated in cells using conventional recombinant DNA technology. Generally, this involved inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook, et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further procaryotic promoters are not recognized and do not function in eucaryotic cells.

Similarly, translation of mRNA in procaryotes depends upon the presence of the proper procaryotic signals which differ from those of eukaryotes. Efficient translation of mRNA in procaryotes requires a ribosome binding site called the Shine-Dalgarno ("SD") sequence on the mRNA. This sequence is a short nucleotide sequence of mRNA that is located before the same codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promoter, recA promotor, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls. Additionally, the cell may carry the gene for a heterologous RNA polymerase such as from phage T7. Thus, a promoter specific for T7 RNA polymerase is used. The T7 RNA polymerase may be under inducible control.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, an SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding a replication polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, viruses, yeast, mammalian cells, insects, plants, and the like.

The invention provides efficient methods of identifying pharmacological agents or lead compounds for agents active at the level of a replication protein function, particularly DNA replication. Generally, these screening methods involve assaying for compounds which interfere with the replication activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of a replication activity or the formation of a complex comprising a replication protein and one or more natural intracellular binding targets. Target indications may include arresting cell growth or causing cell death resulting in recovery from the bacterial infection in animal studies.

A wide variety of assays for activity and binding agents are provided, including DNA synthesis, ATPase, clamp loading onto DNA, protein-protein binding assays, immunoassays, cell based assays, etc. The replication protein compositions, used to identify pharmacological agents, are in isolated, partially pure or pure form and are typically recombinantly produced. The replication protein may be part of a fusion product with another peptide or polypeptide (e.g., a polypeptide that is capable of providing or enhancing protein-protein binding, stability under assay conditions (e.g., a tag for detection or anchoring), etc.). The assay mixtures comprise a natural intracellular replication protein binding target such as DNA, another protein, NTP, or dNTP. For binding assays, while native binding targets may be used, it is frequently preferred to use portions (e.g., peptides, nucleic acid fragments) thereof so long as the portion provides binding affinity and avidity to the subject replication protein conveniently measurable in the assay. The assay mixture also comprises a candidate pharmacological agent. Generally, a plurality of assay mixtures are run in parallel with different agent concentrations to obtain a differential response to the various concentrations. Typically, one of these concentrations serves as a negative control (i.e. at zero concentration or below the limits of assay detection). Additional controls are often present such as a positive control, a dose response curve, use of known inhibitors, use of control heterologous proteins, etc. Candidate agents encompass numerous chemical classes, though typically they are organic compounds; preferably they are small organic compounds and are obtained from a wide variety of sources, including libraries of synthetic or natural compounds. A variety of other reagents may also be included in the mixture. These include reagents like salts, buffers, neutral proteins (e.g., albumin, detergents, etc.), which may be used to facilitate optimal binding and/or reduce nonspecific or background interactions, etc. Also reagents that otherwise improve the efficiency of the assay (e.g., protease inhibitors, nuclease inhibitors, antimicrobial agents, etc.) may be used.

The invention provides replication protein specific assays and the binding agents including natural intracellular binding targets such as other replication proteins, etc., and methods of identifying and making such agents, and their use in a variety of diagnostic and therapeutic applications, especially where disease is associated with excessive cell growth. Novel replication protein-specific binding agents include replication protein-specific antibodies and other natural intracellular binding agents identified with assays such as one- and two-hybrid screens, non-natural intracellular binding agents identified in screens of chemical libraries, etc.

Generally, replication protein-specificity of the binding agent is shown by binding equilibrium constants. Such agents are capable of selectively binding a replication protein (i.e., with an equilibrium constant at least about $10^7$ M$^{-1}$, preferably, at least about $10^8$ M$^{-1}$, more preferably, at least about $10^9$ M$^{-1}$). A wide variety of cell-based and cell-free assays may be used to demonstrate replication protein-specific activity, binding, gel shift assays, immunoassays, etc.

The resultant mixture is incubated under conditions whereby, but for the presence of the candidate pharmacological agent, the replication protein specifically binds the cellular binding target, portion, or analog. The mixture of components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of activity or specific binding between the replication protein and one or more binding targets is detected by any convenient way. For cell-free activity and binding type assays, a separation step may be used to separate the activity product or the bound from unbound components. Separation may be effected by precipitation (e.g., immunoprecipitation), immobilization (e.g., on a solid substrate such as a microtiter plate), etc., followed by washing. Many assays that do not require separation are also possible such as use of europium conjugation in proximity assays or a detection system that is dependent on a product or loss of substrate.

Detection may be effected in any convenient way. For cell-free activity and binding assays, one of the components usually comprises or is coupled to a label. A wide variety of labels may be employed—essentially any label that provides for detection of DNA product, loss of DNA substrate, conversion of a nucleotide substrate, or bound protein is useful. The label may provide for direct detection such as radioactivity, fluorescence, luminescence, optical, or electron density, etc. or indirect detection such as an epitope tag, an enzyme, etc. The label may be appended to the protein (e.g., a phosphate group comprising a radioactive isotope of phosphorous), or incorporated into the DNA substrate or the protein structure (e.g., a methionine residue comprising a radioactive isotope of sulfur.) A variety of methods may be used to detect the label depending on the nature of the label and other assay components. For example, the label may be detected bound to the solid substrate, or a portion of the bound complex containing the label may be separated from the solid substrate, and thereafter the label detected. Labels may be directly detected through optical or electron density, radioactive emissions, nonradiative energy transfer, fluorescence emission, etc. or indirectly detected with antibody conjugates, etc. For example, in the case of radioactive labels, emissions may be detected directly (e.g., with particle counters) or indirectly (e.g., with scintillation cocktails and counters).

The present invention identifies the type of replication system that Gram positive bacteria utilize. Specifically, the replicase is comprised of a DNA polymerase III-type enzyme and it is made functional by other components that are needed for processive function. These components include a sliding clamp and a clamp loader. Hence, Gram negative bacteria do not utilize the replication strategies exemplified by one and two component processive replicases.

The present invention also identifies, partially purifies, and characterizes a second Pol III-type replicase. The polymerase of the second Pol III-type enzyme, termed Pol III-2, behaves like Pol III-L in that it also functions with the clamp and clamp loader components.

This invention also expresses and purifies a protein from a Gram positive bacteria that is homologous to the *E. coli* beta subunit. The invention demonstrates that it behaves like a circular protein. Further, this invention shows that the beta subunit from a Gram positive bacteria is functional with both Pol III-L from a Gram positive bacteria and with DNA polymerase III from a Gram negative bacteria. This result can be explained by an interaction between the clamp and the polymerase that has been conserved during the evolutionary divergence of Gram positive and Gram negative cells. A chemical inhibitor that would disrupt this interaction would be predicted to have a broad spectrum of antibiotic activity, shutting down replication in gram negative and gram positive cells alike. This assay, and others based on this interaction, can be devised to screen chemicals for such inhibition. Further, since all the proteins in this assay are highly overexpressed through recombinant techniques, sufficient quantities of the protein reagents can be obtained for screening hundreds of thousands of compounds.

The present invention provides methods by which replication proteins from a Gram positive bacteria are used to discover new pharmaceutical agents. The function of replication proteins is quantified in the presence of different chemical compounds. A chemical compound that inhibits the function is a candidate antibiotic. Some replication proteins from a Gram positive bacteria and from a Gram negative bacteria can be interchanged for one another. Hence, they can function as mixtures. Reactions that assay for the function of enzyme mixtures consisting of proteins from Gram positive bacteria and from Gram negative bacteria can also be used to discover drugs. Suitable *E. coli* replication proteins are the subunits of its Pol III holoenzyme which are described in U.S. Pat. Nos. 5,583,026 and 5,668,004, which are hereby incorporated by reference.

The methods described here to obtain genes, and the assays demonstrating activity behavior of *S. aureus* are likely to generalize to all members of the Staphylococcus genus and to all Gram positive bacteria.

The present invention describes a method to identify chemicals that inhibit the activity of the Pol III-2 and/or Pol III-L. This method involves contacting primed DNA with the DNA polymerase in the presence of the candidate pharmaceutical, and dNTPs (or modified dNTPs) to form a reaction mixture. The reaction mixture is subjected to conditions effective to achieve nucleic acid polymerization in the absence of the candidate pharmaceutical and the presence or absence of the extension product in the reaction mixture is analyzed. The candidate pharmaceutical is detected by the absence of product.

The present invention describes a method to identify chemicals that inhibit the ability of a beta subunit to stimulate Pol III-2 and/or Pol III-L. This method involves contacting a linear primed DNA with a beta subunit and a DNA polymerase in the presence of the candidate compound, and dNTPs (or modified dNTPs) to form a reaction mixture. The reaction mixture is subjected to conditions which, in the absence of the candidate compound, would affect nucleic acid polymerization and the presence or absence of the extension product in the reaction mixture is analyzed. The candidate pharmaceutical is detected by the absence of product. The beta subunit and/or the DNA polymerase are derived from a Gram positive bacterium.

The present invention also describes a method to identify candidate pharmaceuticals that inhibit the activity of a gamma complex (or a subunit or subassembly of the gamma complex) and a beta subunit in stimulating either Pol III-2 or Pol III-L. The method includes contacting a primed DNA (which may be coated with SSB) with a DNA polymerase, a beta subunit, and a gamma complex (or subunit or subassembly of the gamma complex) in the presence of the candidate pharmaceutical, and dNTPs (or modified dNTPs) to form a reaction mixture. The reaction mixture is subjected to conditions which in the absence of the candidate pharmaceutical would effect nucleic acid polymerization and the presence or absence of the extension product in the reaction mixture is analyzed. The candidate pharmaceutical is detected by the absence of product. The DNA polymerase, the beta subunit, and/or the gamma complex or subunit(s) thereof are derived from a Gram positive bacterium.

The present invention describes a method to identify chemicals that inhibit the ability of a beta subunit and a DNA polymerase to interact physically. This method involves contacting the beta subunit with the DNA polymerase in the presence of the candidate pharmaceutical to form a reaction mixture. The reaction mixture is subjected to conditions under which the DNA polymerase and the beta subunit would interact in the absence of the candidate pharmaceutical. The reaction mixture is then analyzed for interaction between the beta unit and the DNA polymerase. The candidate pharmaceutical is detected by the absence of interaction between the beta subunit and the DNA polymerase. The DNA polymerase and/or the beta subunit are derived from a Gram positive bacterium.

The present invention describes a method to identify chemicals that inhibit the ability of a beta subunit and a gamma complex (or a subunit or subassembly of the gamma complex) to interact. This method includes contacting the beta subunit with the gamma complex (or subunit or subassembly of the gamma complex) in the presence of the candidate pharmaceutical to form a reaction mixture. The reaction mixture is subjected to conditions under which the gamma complex (or the subunit or subassembly of the gamma complex) and the beta subunit would interact in the absence of the candidate pharmaceutical. The reaction mixture is then analyzed for interaction between the beta subunit and the gamma complex (or the subunit or subassembly of the gamma complex). The candidate pharmaceutical is detected by the absence of interaction between the beta subunit and the gamma complex (or the subunit or subassembly of the gamma complex). The beta subunit and/or the gamma complex or subunit thereof is derived from a Gram positive bacterium.

The present invention describes a method to identify chemicals that inhibit the ability of a gamma complex (or a subassembly of the gamma complex) to assemble a beta subunit onto a DNA molecule. This method involves contacting a circular primed DNA molecule (which may be coated with SSB) with the gamma complex (or the subassembly thereof) and the beta subunit in the presence of the candidate pharmaceutical, and ATP or dATP to form a reaction mixture. The reaction mixture is subjected to conditions under which the gamma complex (or subassembly) assembles the beta subunit on the DNA molecule absent the candidate pharmaceutical. The presence or absence of the beta subunit on the DNA molecule in the reaction mixture is analyzed. The candidate pharmaceutical is detected by the absence of the beta subunit on the DNA molecule. The beta subunit and/or the gamma complex are derived from a Gram positive bacterium.

The present invention describes a method to identify chemicals that inhibit the ability of a gamma complex (or a subunit(s) of the gamma complex) to disassemble a beta subunit from a DNA molecule. This method comprises contacting a DNA molecule onto which the beta subunit has been assembled in the presence of the candidate pharmaceutical, to form a reaction mixture. The reaction mixture is subjected to conditions under which the gamma complex (or a subunit(s) or subassembly of the gamma complex) disassembles the beta subunit from the DNA molecule absent the candidate pharmaceutical. The presence or absence of the beta subunit on the DNA molecule in the reaction mixture is analyzed. The candidate pharmaceutical is detected by the presence of the beta subunit on the DNA molecule. The beta subunit and/or the gamma complex are derived from a Gram positive bacterium.

The present invention describes a method to identify chemicals that dissassemble a beta subunit from a DNA molecule. This method involves contacting a circular primed DNA molecule (which may be coated with SSB) upon which the beta subunit has been assembled (e.g., by action of the gamma complex) with the candidate pharmaceutical. The presence or absence of the beta subunit on the DNA molecule in the reaction mixture is analyzed. The candidate pharmaceutical is detected by the absence of the beta subunit on the DNA molecule. The beta subunit is derived from a Gram positive bacterium.

The present invention describes a method to identify chemicals that inhibit the dATP/ATP binding activity of a gamma complex or a gamma complex subunit (e.g., gamma subunit). This method includes contacting the gamma complex (or the gamma complex subunit) with dATP/ATP either in the presence or absence of a DNA molecule and/or the beta subunit in the presence of the candidate pharmaceutical to form a reaction. The reaction mixture is subjected to conditions in which the gamma complex (or the subunit of gamma complex) interacts with dATP/ATP in the absence of the candidate pharmaceutical. The reaction is analyzed to determine if dATP/ATP is bound to the gamma complex (or the subunit of gamma complex) in the presence of the candidate pharmaceutical. The candidate pharmaceutical is detected by the absence of hydrolysis. The gamma complex and/or the beta subunit is derived from a Gram positive bacterium.

The present invention describes a method to identify chemicals that inhibit the dATP/ATPase activity of a gamma complex or a gamma complex subunit (e.g., the gamma subunit). This method involves contacting the gamma complex (or the gamma complex subunit) with dATP/ATP either in the presence or absence of a DNA molecule and/or a beta subunit in the presence of the candidate pharmaceutical to form a reaction mixture. The reaction mixture is subjected to conditions in which the gamma subunit (or complex) hydrolyzes dATP/ATP in the absence of the candidate pharmaceutical. The reaction is analyzed to determine if dATP/ATP was hydrolyzed. Suitable candidate pharmaceuticals are identified by the absence of hydrolysis. The gamma complex and/or the beta subunit is derived from a Gram positive bacterium.

The present invention describes methods to identify chemicals that inhibit the activity of a DNA polymerase encoded by either the dnaE gene or PolC gene. These methods are as follows.

1) Contacting a primed DNA molecule with the encoded product of the dnaE gene or PolC gene in the presence of the candidate pharmaceutical, and dNTPs (or modified dNTPs) to form a reaction mixture. The reaction mixture is subjected to conditions, which in the absence of the candidate pharmaceutical, affect nucleic acid polymerization and the presence or absence of the extension product in the reaction mixture is analyzed. The candidate pharmaceutical is detected by the absence of extension product. The protein encoded by the dnaE gene and PolC gene is derived from a Gram positive bacterium.

2) Contacting a linear primed DNA molecule with a beta subunit and the encoded product of dnaE or PolC in the presence of the candidate pharmaceutical, and dNTPs (or modified dNTPs) to form a reaction mixture. The reaction mixture is subjected to conditions, which in the absence of the candidate pharmaceutical, affect nucleic acid polymerization, and the presence or absence of the extension product in the reaction mixture is analyzed. The candidate pharmaceutical is detected by the absence of extension product. The protein encoded by the dnaE gene and PolC gene is derived from a Gram positive bacterium.

3) Contacting a circular primed DNA molecule (may be coated with SSB) with a gamma complex, a beta subunit and the encoded product of a dnaE gene or PolC gene in the presence of the candidate pharmaceutical, and dNTPs (or modified dNTPs) to form a reaction mixture. The reaction mixture is subjected to conditions, which in the absence of the candidate pharmaceutical, affect nucleic acid polymerization, and the presence or absence of the extension product in the reaction mixture is analyzed. The candidate pharmaceutical is detected by the absence of product. The protein encoded by the dnaE gene and PolC gene, the beta subunit, and/or the gamma complex are derived from a Gram positive bacterium.

4) Contacting a beta subunit with the product encoded by a dnaE gene or PolC gene in the presence of the candidate pharmaceutical to form a reaction mixture. The reaction mixture is then analyzed for interaction between the beta subunit and the product encoded by the dnaE gene or PolC gene. The candidate pharmaceutical is detected by the absence of interaction between the beta subunit and the product encoded by the dnaE gene or PolC gene. The beta subunit and/or the protein encoded by the dnaE gene and PolC gene is derived from a Gram positive bacterium.

The present invention discloses a method to identify chemicals that inhibit a DnaB helicase. The method includes contacting the DnaB helicase with a DNA molecule substrate that has a duplex region in the presence of a nucleoside or deoxynucleoside triphosphate energy source and a candidate pharmaceutical to form a reaction mixture. The reaction mixture is subjected to conditions that support helicase activity in the absence of the candidate pharmaceutical. The DNA duplex molecule in the reaction mixture is analyzed for whether it is converted to ssDNA. The candidate pharmaceutical is detected by the absence of conversion of the duplex DNA molecule to the ssDNA molecule. The DnaB helicase is derived from a Gram positive bacterium.

The present invention describes a method to identify chemicals that inhibit the nucleoside or deoxynucleoside triphosphatase activity of a DnaB helicase. The method includes contacting the DnaB helicase with a DNA molecule substrate that has a duplex region in the presence of a nucleoside or deoxynucleoside triphosphate energy source and the candidate pharmaceutical to form a reaction mixture. The reaction mixture is subjected to conditions that support nucleoside or deoxynucleoside triphosphatase activity of the DnaB helicase in the absence of the candidate pharmaceutical. The candidate pharmaceutical is detected by the absence of conversion of nucleoside or deoxynucleoside triphosphate to nucleoside or deoxynucleoside diphosphate. The DnaB helicase is derived from a Gram positive bacterium.

The present invention describes a method to identify chemicals that inhibit a primase. The method includes contacting primase with a ssDNA molecule in the presence of a candidate pharmaceutical to form a reaction mixture. The reaction mixture is subjected to conditions that support primase activity (e.g., the presence of nucleoside or deoxynucleoside triphosphates, appropriate buffer, presence or absence of DnaB protein) in the absence of the candidate pharmaceutical. Suitable candidate pharmaceuticals are identified by the absence of primer formation detected either directly or indirectly. The primase is derived from a Gram positive bacterium.

The present invention describes a method to identify chemicals that inhibit the ability of a primase and the protein encoded by a DnaB gene to interact. This method includes contacting the primase with the protein encoded by the DnaB gene in the presence of the candidate pharmaceutical to form a reaction mixture. The reaction mixture is subjected to conditions under which the primase and the protein encoded by the DnaB gene interact in the absence of the candidate pharmaceutical. The reaction mixture is then analyzed for interaction between the primase and the protein encoded by the DnaB gene. The candidate pharmaceutical is detected by the absence of interaction between the primase and the protein encoded by the DnaB gene. The primase and/or the DnaB gene are derived from a Gram positive bacterium.

The present invention describes a method to identify chemicals that inhibit the ability of a protein encoded by a DnaB gene to interact with a DNA molecule. This method includes contacting the protein encoded by the DnaB gene with the DNA molecule in the presence of the candidate pharmaceutical to form a reaction mixture. The reaction mixture is subjected to conditions under which the DNA molecule and the protein encoded by the DnaB gene interact in the absence of the candidate pharmaceutical. The reaction mixture is then analyzed for interaction between the protein encoded by the DnaB gene and the DNA molecule. The candidate pharmaceutical is detected by the absence of interaction between the DNA molecule and the protein encoded by the DnaB gene. The DnaB gene is derived from a Gram positive bacterium.

EXAMPLES

Example 1

Materials

Labeled deoxy- and ribonucleoside triphosphates were from Dupont—New England Nuclear; unlabelled deoxy- and ribonucleoside triphosphates were from Pharmacia-LKB; *E. coli* replication proteins were purified as described, alpha, epsilon, gamma, and tau (Studwell, et al., "Processive Replication is Contingent on the Exonuclease Subunit of DNA Polymerase III Holoenzyme," *J. Biol. Chem.* 265:1171-1178 (1990), which is hereby incorporated by reference), beta (Kong, et. al, "Three Dimensional Structure of the Beta Subunit of *Escherichia coli* DNA Polymerase III Holoenzyme: A Sliding DNA Clamp," *Cell*, 69:425-437 (1992), which is hereby incorporated by reference), delta and delta prime (Dong, et. al., "DNA Polymerase III Accessory Proteins. I. HolA and holB Encoding $\delta$ and $\delta'$," *J. Biol. Chem.*, 268: 11758-11765 (1993), which is hereby incorporated by reference), chi and psi (Xiao, et. al., "DNA Polymerase III Accessory Proteins. III. HolC and holD Encoding chi and psi," *J. Biol. Chem.*, 268:11773-11778 (1993), which is hereby incorporated by reference), theta (Studwell-Vaughan, et al., "DNA Polymerase III Accessory Proteins. V. Theta Encoded by holE," *J. Biol. Chem.*, 268:11785-11791 (1993), which is hereby incorporated by reference), and SSB (Weiner, et. al., "The Deoxyribonucleic Acid Unwinding Protein of *Escherichia coli*," *J. Biol. Chem.*, 250:1972-1980 (1975), which is hereby incorporated by reference). *E. coli* Pol III core, and gamma complex (composed of subunits: gamma, delta, delta prime, chi, and psi) were reconstituted as described in Onrust, et. al., "Assembly of a Chromosomal Replication Machine: Two DNA Polymerases, a Clamp Loader and Sliding Clamps in One Holoenzyme Particle. I. Organization of the Clamp Loader," *J. Biol. Chem.*, 270:13348-13357 (1995), which is hereby incorporated by reference. Pol III* was reconstituted and purified as described in Onrust, et. al., "Assembly of a Chromosomal Replication Machine: Two DNA Polymerases, a Clamp Loader and Sliding Clamps in One Holoenzyme Particle. III. Interface Between Two Polymerases and the Clamp Loader," *J. Biol. Chem.*, 270:13366-13377 (1995), which is hereby incorporated by reference. Protein concentrations were quantitated by the Protein Assay (Bio-Rad) method using bovine serum albumin (BSA) as a standard. DNA oligonucleotides were synthesized by Oligos etc. Calf thymus DNA was from Sigma. Buffer A is 20 mM Tris-HCl (pH=7.5), 0.5 mM EDTA, 2 mM DTT, and 20% glycerol. Replication buffer is 20 mM Tris-Cl (pH 7.5), 8 mM $MgCl_2$, 5 mM DTT, 0.5 mM EDTA, 40 µg/ml BSA, 4% glycerol, 0.5 mM ATP, 3 mM each dCTP, dGTP, dATP, and 20 µM [$\alpha$-$^{32}$P] dTTP. P-cell buffer was 50 mM potassium phosphate (pH 7.6), 5 mM DTT, 0.3 mM EDTA, 20% glycerol. T.E. buffer is 10 mM Tris-HCl (pH 7.5), 1 mM EDTA. Cell lysis buffer was 50 mM Tris-HCl (pH 8.0) 10% sucrose, 1 M NaCl, 0.3 mM spermidine.

Example 2

Calf Thymus DNA Replication Assays

These assays were used in the purification of DNA polymerases from *S. aureus* cell extracts. Assays contained 2.5 µg activated calf thymus DNA in a final volume of 25 µl replication buffer. An aliquot of the fraction to be assayed was added to the assay mixture on ice followed by incubation at 37° C. for 5 min. DNA synthesis was quantitated using DE81 paper as described in Rowen, et al., "Primase, the DnaG Protein of *Escherichia coli*. An Enzyme Which Starts DNA Chains," *J. Biol. Chem.*, 253:758-764 (1979), which is hereby incorporated by reference.

Example 3

PolydA-oligodT Replication Assays

PolydA-oligodT was prepared as follows. PolydA of average length 4500 nucleotides was purchased from SuperTecs. OligodT35 was synthesized by Oligos etc. 145 ul of 5.2 mM (as nucleotide) polydA and 22 µl of 1.75 mM (as nucleotide) oligodT were mixed in a final volume of 2100 µl T.E. buffer (ratio as nucleotide was 21:1 polydA to oligodT). The mixture was heated to boiling in a 1 ml eppindorf tube, then removed and allowed to cool to room temperature. Assays were performed in a final volume of 25 µl 20 mM Tris-Cl (pH 7.5), 8 mM $MgCl_2$, 5 mM DTT, 0.5 mM EDTA, 40 µg/ml BSA, 4% glycerol, containing 20 µM [$\alpha$-$^{32}$P]dTTP and 0.36 µg polydA-oligodT. Proteins were added to the reaction on ice, then shifted to 37° C. for 5 min. DNA synthesis was quantitated using DE81 paper as described in Rowen, et al., "Primase, the DnaG Protein of *Escherichia coli*. An Enzyme Which Starts DNA Chains," *J. Biol. Chem.*, 253:758-764 (1979), which is hereby incorporated by reference.

Example 4

Singly Primed M13mp18 ssDNA Replication Assays

M13mp18 was phenol extracted from phage and purified by two successive bandings (one downward and one upward) in cesium chloride gradients. M13mp18 ssDNA was singly primed with a DNA 30mer (map position 6817-6846) as described in Studwell, et al. "Processive Replication is Contingent on the Exonuclease Subunit of DNA Polymerase III Holoenzyme," *J. Biol. Chem.*, 265:1171-1178 (1990), which is hereby incorporated by reference. Replication assays contained 72 ng of singly primed M13mp18 ssDNA in a final volume of 25 µl of replication buffer. Other proteins added to the assay, and their amounts, are indicated in the Brief Description of the Drawings. Reactions were incubated for 5 min. at 37° C. and then were quenched upon adding an equal volume of 1% SDS and 40 mM EDTA. DNA synthesis was quantitated using DE81 paper as described in Rowen, et al., "Primase, the DnaG Protein of *Escherichia coli*. An Enzyme Which Starts DNA Chains," *J. Biol. Chem.*, 253:758-764 (1979), which is hereby incorporated by reference, and product analysis was performed in a 0.8% native agarose gel followed by autoradiography.

Example 5

Genomic *Staphylococcus aureus* DNA

Two strains of *S. aureus* were used. For PCR of the first fragment of the dnaX gene sequence, the strain was ATCC 25923. For all other work the strain was strain 4220 (a gift of Dr. Pat Schlievert, University of Minnesota). This strain lacks a gene needed for producing toxic shock (Kreiswirth, et al., "The Toxic Shock Syndrome Exotoxin Structural Gene is Not Detectably Transmitted by a Prophage," Nature, 305:709-712 (1996) and Balan, et al., "Autocrine Regulation of Toxin Synthesis by *Staphylococcus aureus*," Proc. Natl. Acad. Sci. USA, 92:1619-1623 (1995), which are hereby incorporated by reference). *S. aureus* cells were grown overnight at 37° C. in LB containing 0.5% glucose. Cells were collected by centrifugation (24 g wet weight). Cells were resuspended in 80 ml solution 1 (50 mM glucose, 10 mM EDTA, 25 mM Tris-HCL (pH 8.0)). Then, SDS and NaOH were added to 1% and 0.2 N, respectively, followed by incubation at 65° C. for 30 min. to lyse the cells. 68.5 ml of 3 M sodium acetate (pH 5.0) was added followed by centrifugation at 12,000 rpm for 30 min. The supernatant was discarded and the pellet was washed twice with 50 ml of 6M urea, 10 mM Tris-HCL (pH 7.5), 1 mM EDTA) using a dounce homogenizer. After each wash, the resuspended pellet was collected by centrifugation (12,000 rpm for 20 min.). After the second wash, the pellet was resuspended in 50 ml 10 mM T.E. buffer using a dounce homogenizer and then incubated for 30 min. at 65° C. The solution was centrifuged at 12,000 rpm for 20 min., and the viscous supernatant was collected. 43.46 g $CsCl_2$ was added to the 50 ml of supernatant (density between 1.395-1.398) and poured into two 35 ml quick seal ultracentrifuge tubes (tubes were completely filled using the same density of $CsCl_2$ in T.E.). To each tube was added 0.5 ml of a 10 mg/ml stock of ethidium bromide. Tubes were spun at 55,000 rpm for 18 h at 18° C. in a Sorvall TV860 rotor. The band of genomic DNA was extracted using a syringe and needle. Ethidium bromide was removed using two butanol extractions and then dialyzed against 4l of T.E. at pH 8.0 overnight. The DNA was recovered by ethanol precipitation and then resuspended in T.E. buffer (1.7 mg total) and stored at −20° C.

Example 6

Cloning and Purification of *S. aureus* Pol III-L Holoenzyme

To further characterize the mechanism of DNA replication in *S. aureus*, large amounts of its replication proteins were produced through use of the genes. The PolC gene encoding *S. aureus* Pol III-L holoenzyme has been sequenced and expressed in *E. coli* (Pacitti, et. al., "Characterization and Overexpression of the Gene Encoding *Staphylococcus aureus* DNA Polymerase III," Gene, 165:51-56 (1995), which is hereby incorporated by reference). The previous work utilized a pBS[KS] vector for expression in which the *E. coli* RNA polymerase is used for gene transcription. In the earlier study, the *S. aureus* Pol III gene was precisely cloned at the 5' end encoding the N-terminus, but the amount of the gene that remained past the 3' end was not disclosed and the procedure for subcloning the gene into the expression vector was only briefly summarized. Furthermore, the previous study does not show the level of expression of the *S. aureus* Pol III, nor the amount of *S. aureus* Pol III-L that is obtained from the induced cells. Since the previously published procedure could not be repeated and the efficiency of the expression vector could not be assessed, another strategy outlined below had to be developed.

The isolated Pol III gene was cloned into a vector that utilizes T7 RNA polymerase for transcription as this process generally expresses a large amount of protein. Hence, the *S. aureus* PolC gene was cloned precisely into the start codon at the NdeI site downstream of the T7 promotor in a pET vector. As the PolC gene contains an internal NdeI site, the entire gene could not be amplified and placed it into the NdeI site of a pET vector. Hence, a three step cloning strategy that yielded the desired clone was devised (See FIG. 1). These attempts were quite frustrating initially as no products of cloning in standard *E. coli* strains such as DH5alpha, a typical laboratory strain for preparation of DNA, could be obtained. Finally, a cell that was mutated in several genes affecting DNA stability was useful in obtaining the desired products of cloning.

In brief, the cloning strategy required use of another expression vector (called pET1137 kDa) in which the 37 kDa subunit of human RFC, the clamp loader of the human replication system, had been cloned into the pET11 vector. The gene encoding the 37 kDa subunit contains an internal NsiI site, which was needed for the precise cloning of the isolated PolC gene. This three step strategy is shown in FIG. 1. In the first step, an approximately 2.3 kb section of the 5' section of the gene (encoding the N-terminus of Pol III-L) was amplified using the polymerase chain reaction (PCR). Primers were: upstream 5'-GGTGGTAATTGTCTTG CATATGACAGAGC-3' (SEQ. ID. No. 13); downstream 5'-AGCGATTAAGTGGATTGCCGGGTTGTGATG C-3' (SEQ. ID. No. 14). Amplification was performed using 500 ng genomic DNA, 0.5 mM EDTA, 1 µM of each primer, 1 mM MgSO$_4$, 2 units vent DNA polymerase (New England Biolabs) in 100 µl of vent buffer (New England Biolabs). Forty cycles were performed using the following cycling scheme: 94° C., 1 min; 60° C., 1 min.; 72° C., 2.5 min. The product was digested with NdeI (underlined in the upstream primer) and NsiI (an internal site in the product) and the approximately 1.8 kb fragment was gel purified. A pET11 vector containing as an insert the 37 kDa subunit of human replication factor C (pET1137 kDa) was digested with NdeI and NsiI and gel purified. The PCR fragment was ligated into the digested pET1137 kDa vector and the ligation reaction was transformed into Epicurean coli supercompetent SURE 2 cells (Stratagene) and colonies were screened for the correct chimera (pET11PolC1) by examining minipreps for proper length and correct digestion products using NdeI and NsiI. In the second step, an approximately 2076 bp fragment containing the DNA encoding the C-terminus of Pol III-L holoenzyme was amplified using as primers: upstream 5'-AGCAT-CACAACCCGGCAATCCACTTAATCG C-3' (SEQ. ID. No. 15); downstream, 5'-GACTACG CCATGGGCATTAAATAAATACC-3' (SEQ. ID. No. 16). The amplification cycling scheme was as described above except the elongation step at 72° C. was for 2 min. The product was digested with BamHI (underlined in the downstream primer) and NsiI (internal to the product) and the approximately 480 bp product was gel purified and ligated into the pET11PolC1 that had been digested with NsiI/BamHI and gel purified (ligated product is pET11PolC2). To complete the expression vector, an approximately 2080 bp PCR product was amplified over the two NsiI sites internal to the gene using the following primers: upstream 5'-GAAG ATGCATATAAACGTGCA AGACCTAGT C-3' (SEQ. ID. No. 17), downstream 5'-GTCTGACGCACGAATTG-TAAAGTAAGATGCATA G-3' (SEQ. ID. No. 18). The amplification cycling scheme was as described above except the 72° C. elongation step was 2 min. The PCR product, and the pET11PolC2 vector, were digested with NsiI and gel purified. The ligation mixture was transformed as described above and colonies were screened for the correct chimera (pET11PolC).

Figure 2:
FIGS. 2A-C describe the expression and purification of *S. aureus* Pol III-L.
Figure 2:
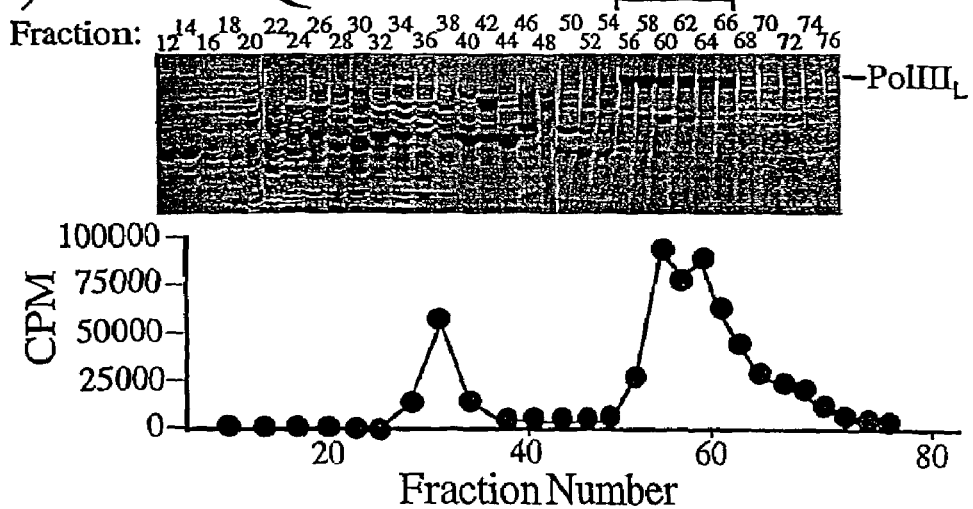
Figure 2:
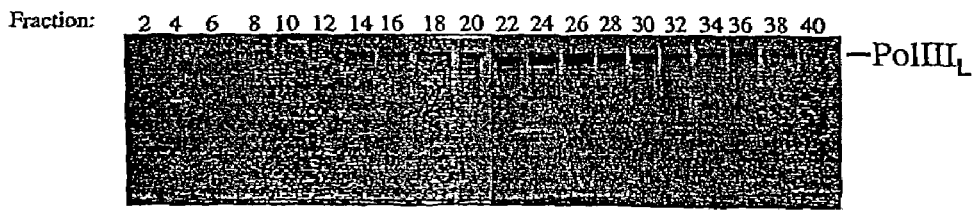

To express Pol III-L holoenzyme, the pET11PolC plasmid was transformed into *E. coli* strain BL21 (DE3). 24 L of *E. coli* BL21 (DE3)pET11PolC were grown in LB media containing 50 µg/ml ampicillin at 37° C. to an OD of 0.7 and then the temperature was lowered to 15° C. Cells were then induced for Pol III-L expression upon addition of 1 mM IPTG to produce the T7 RNA polymerase needed to transcribe PolC holoenzyme. This step was followed by further incubation at 15° C. for 18 h. Expression of *S. aureus* Pol III-L holoenzyme was so high that it could easily be visualized by Coomassie staining of a SDS polyacrylamide gel of whole cells (FIG. 2A). The expressed protein migrated in the SDS polyacrylamide gel in a position expected for a 165 kDa polypeptide. In this procedure, it is important that cells are induced at 15° C., as induction at 37° C. produces a truncated version of Pol III-L holoenzyme, of approximately 130 kDa.

Cells were collected by centrifugation at 5° C. Cells (12 g wet weight) were stored at −70° C. The following steps were performed at 4° C. Cells were thawed and lysed in cell lysis buffer as described (final volume=50 ml) and were passed through a French Press (Amico) at a minimum of 20,000 psi. PMSF (2 mM) was added to the lysate as the lysate was collected from the French Press. DNA was removed and the lysate was clarified by centrifugation. The supernatent was dialyzed for 1 h against Buffer A containing 50 mM NaCl. The final conductivity was equivalent to 190 mM NaCl. Supernatent (24 ml, 208 mg) was diluted to 50 ml using Buffer A to bring the conductivity to 96 MM MgCl$_2$, and then was loaded onto an 8 ml MonoQ column equilibrated in Buffer A containing 50 mM NaCl. The column was eluted with a 160 ml linear gradient of Buffer A from 50 mM NaCl to 500 mM NaCl. Seventy five fractions (1.3 ml each) were collected (see FIG. 2B). Aliquots were analyzed for their ability to synthesize DNA, and 20 µl of each fraction was analyzed by Coomassie staining of an SDS polyacrylamide gel. Based on the DNA synthetic capability, and the correct size band in the gel, fractions 56-65 containing Pol III-L holoenzyme were pooled (22 ml, 31 mg). The pooled fractions were dialyzed overnight at 4° C. against 50 mM phosphate (pH 7.6), 5 mM DTT, 0.1 mM EDTA, 2 mM PMSF, and 20% glycerol (P-cell buffer). The dialyzed pool was loaded onto a 4.5 ml phosphocellulose column equilibrated in P-cell buffer, and then eluted with a 25 ml linear gradient of P-cell buffer from 0 M NaCl to 0.5 M NaCl. Fractions of 1 ml were collected and analyzed in a SDS polyacrylamide gel stained with Coomassie Blue (see FIG. 2C). Fractions 20-36 contained the majority of the Pol III-large at a purity of greater than 90% (5 mg).

Example 7

*S. aureus* Pol III-L is Not Processive on its Own

The Pol III-L holoenzyme purifies from *B. subtilis* as a single subunit without accessory factors (Barnes, et al., "Purification of DNA Polymerase III of Gram-positive Bacteria," *Methods in Enzy.*, 262:35-42 (1995), which is hereby incorporated by reference). Hence, it seemed possible that it may be a Type I replicase (e.g., like T5 polymerase) and, thus, be capable of extending a single primer full length around a long singly primed template. To perform this experiment, a template M13mp18 ssDNA primed with a single DNA oligonucleotide either in the presence or absence of SSB was used. DNA products were analyzed in a neutral agarose gel which resolved products by size. The results showed that Pol III-L holoenzyme was incapable of extending the primer around the DNA (to form a completed duplex circle referred to as replicative form II (RFII)) whether SSB was present or not. This experiment has been repeated using more enzyme and longer times, but no full length RFII products are produced. Hence, Pol III-L would appear not to follow the paradigm of the T5 system (Type I replicase) in which the polymerase is efficient in synthesis in the absence of any other protein(s).

Example 8

Cloning and Purification of *S. aureus* Beta Subunit

The sequence of an *S. aureus* homolog of the *E. coli* dnaN gene (encoding the beta subunit) was obtained in a study in which the large recF region of DNA was sequenced (Alonso, et al., "Nucleotide Sequence of the recF Gene Cluster From *Staphylococcus aureus* and Complementation Analysis in *Bacillus subtilis* recF Mutants," *Mol. Gen. Genet.*, 246:680-686 (1995), Alonso, et al., "Nucleotide Sequence of the recF Gene Cluster From *Staphylococcus aureus* and Complementation Analysis in *Bacillus subtilis* recF Mutants," *Mol. Gen. Genet.*, 248:635-636 (1995), which are hereby incorporated by reference). Sequence alignment of the *S. aureus* beta and *E. coli* beta show approximately 30% identity. Overall this level of homology is low and makes it uncertain that *S. aureus* beta will have the same shape and function as the *E. coli* beta subunit.

Figure 3:
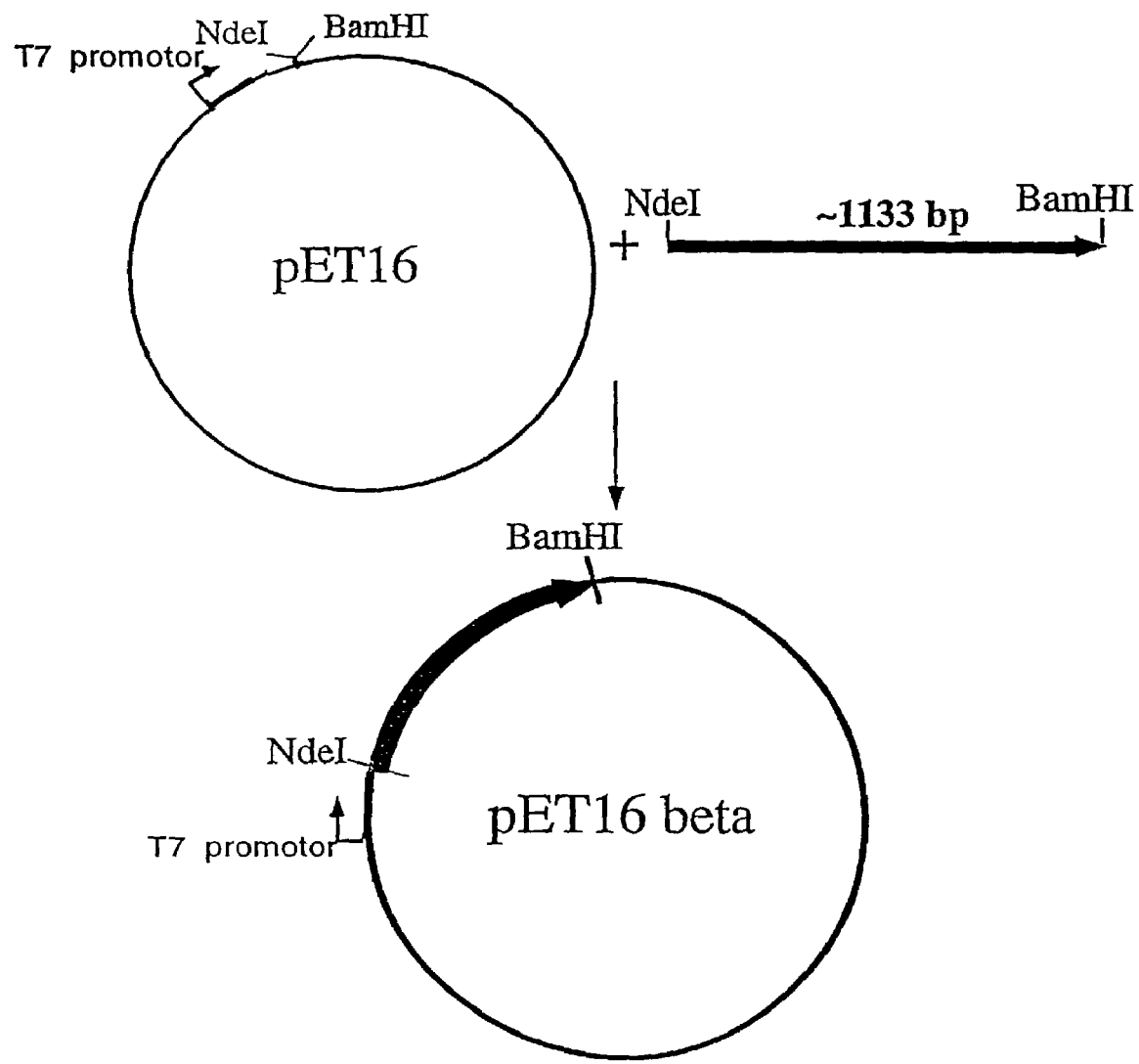
FIG. 3 shows the *S. aureus* beta expression vector. The dnaN gene was amplified from *S. aureus* genomic DNA and cloned into the pET16 expression vector.

To obtain *S. aureus* beta protein, the dnaN gene was isolated and precisely cloned into a pET vector for expression in *E. coli. S. aureus* genomic DNA was used as template to amplify the homolog of the dnaN gene (encoding the putative beta). The upstream and downstream primers were designed to isolate the dnaN gene by PCR amplification from genomic DNA. Primers were: upstream 5'-CGACTGGAAG-GAGTTTTAACATATGATGGAATTCAC-3' (SEQ. ID. No. 19); the NdeI site used for cloning into pET16b is underlined. The downstream primer was 5'-TTATAT GGATCCTTAGTAAGTTCTGATTGG-3' (SEQ. ID. No. 20); where the BamHI site used for cloning into pET16b (Novagen) is underlined. The NdeI and BamHI sites were used for directional cloning into pET16 (FIG. 3). Amplification was performed using 500 ng genomic DNA, 0.5 mM dNTPs, 1 µM of each primer, 1 mM MgSO$_4$, 2 units vent DNA polymerase in 100 ul of vent buffer. Forty cycles were performed using the following cycling scheme: 94° C., 1 min; 60° C., 1 min.; 72° C., 1 min. 10 s. The 1167 bp product was digested with NdeI and BamHI and purified in a 0.7% agarose gel. The pure digested fragment was ligated into the pET16b vector which had been digested with NdeI and BamHI and gel purified in a 0.7% agarose gel. Ligated products were transformed into *E. coli* competent SURE II cells (Stratagene) and colonies were screened for the correct chimera by examining minipreps for proper length and correct digestion products using NdeI and BamHI.

Figure 4:
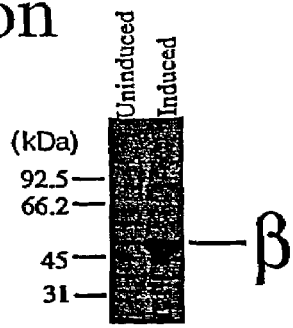
FIGS. 4A-C describe the expression and purification of *S. aureus* beta.
Figure 4:
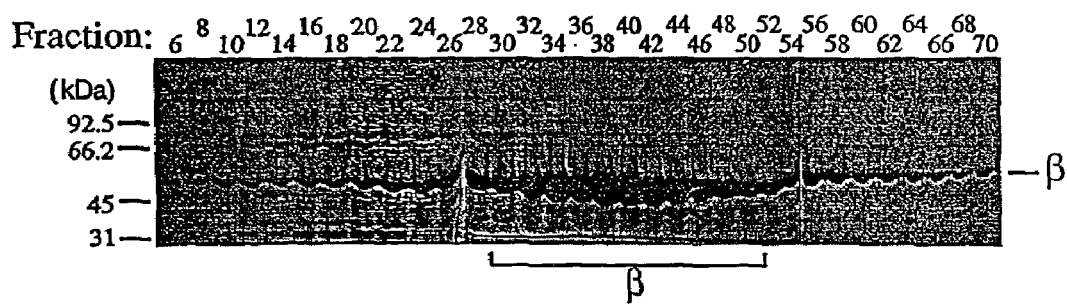
Figure 4:
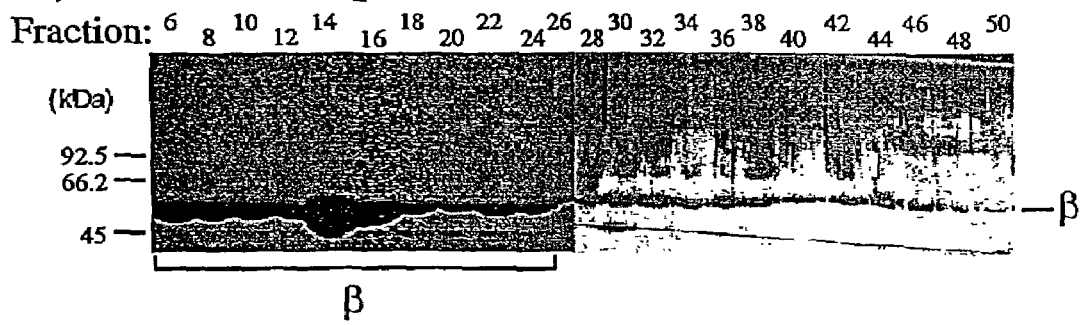

24 L of of BL21 (DE3)pETheta cells were grown in LB containing 50 µg/ml ampicillin at 37° C. to an O.D. of 0.7, and, then, the temperature was lowered to 15° C. IPTG was added to a concentration of 2 mM and after a further 18 h at 15° C. to induce expression of *S. aureus* beta (FIG. 4A). It is interesting to note that the beta subunit, when induced at 37° C., was completely insoluble. However, induction of cells at 15° C. provided strong expression of beta and, upon cell lysis, over 50% of the beta was present in the soluble fraction.

Cells were harvested by centrifugation (44 g wet weight) and stored at −70° C. The following steps were performed at 4° C. Cells (44 g wet weight) were thawed and resuspended in 45 ml 1×binding buffer (5 mM imidizole, 0.5 M NaCl, 20 mM Tris HCl (final pH 7.5)) using a dounce homogenizer. Cells were lysed using a French Pressure cell (Aminco) at 20,000 psi, and then 4.5 ml of 10% polyamine P (Sigma) was added. Cell debris and DNA was removed by centrifugation at 13,000 rpm for 30 min. at 4° C. The pET16beta vector places a 20 residue leader containing 10 histidine residues at the N-terminus of beta. Hence, upon lysing the cells, the *S. aureus* beta was greatly purified by chromatography on a nickel chelate resin (FIG. 4B). The supernatant (890 mg protein) was applied to a 10 ml HiTrap Chelating Separose column (Pharmacia-LKB) equilibrated in binding buffer. The column was washed with binding buffer, then eluted with a 100 ml linear gradient of 60 mM imidazole to 1 M imidazole in binding buffer. Fractions of 1.35 ml were collected. Fractions were analyzed for the presence of beta in an SDS polyacrylamide gel stained with Coomassie Blue. Fractions 28-52, containing most of the beta subunit, were pooled (35 ml, 82 mg). Remaining contaminating protein was removed by chromatography on MonoQ. The *S. aureus* beta becomes insoluble as the ionic strength is lowered, and, thus, the pool of beta was dialyzed overnight against Buffer A containing 400 mM NaCl. The dialyzed pool became slightly turbid indicating it was at its solubility limit at these concentrations of protein and NaCl. The insoluble material was removed by centrifugation (64 mg remaining) and, then, diluted 2-fold with Buffer A to bring the conductivity to 256. The protein was then applied to an 8 ml MonoQ column equilibrated in Buffer A plus 250 mM NaCl and then eluted with a 100 ml linear gradient of Buffer A from 0.25M NaCl to 0.75 M NaCl; fractions of 1.25 ml were collected (FIG. 4C). Under these conditions, approximately 27 mg of the beta flowed through the column and the remainder eluted in fractions 1-18 (24 mg).

Example 9

Figure 5:
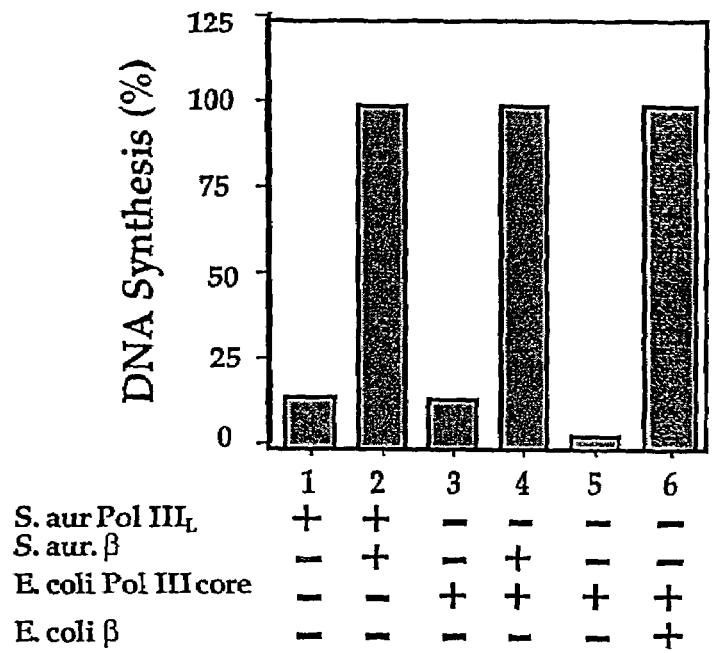
FIGS. 5A-B demonstrate that the *S. aureus* beta stimulates *S. aureus* Pol III-L and *E. coli* Pol III core on linear DNA, but not circular DNA.
Figure 5:
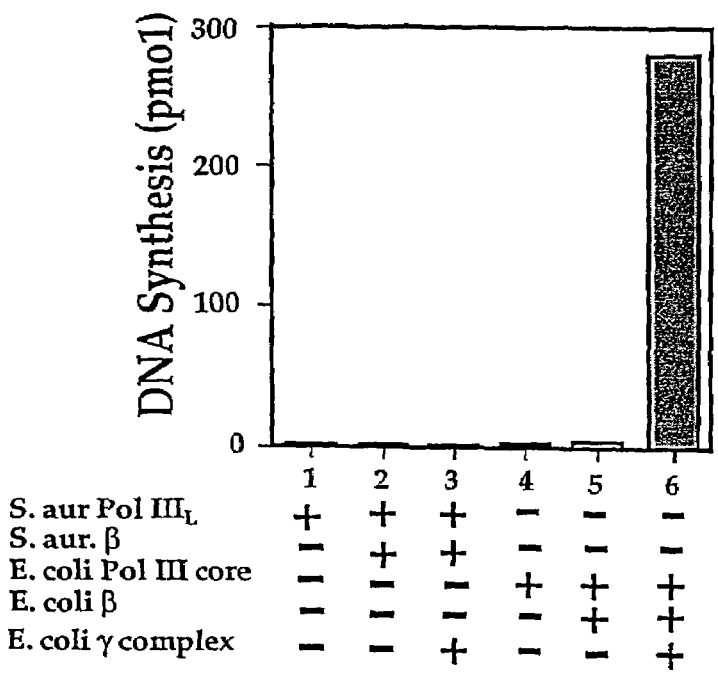

The *S. aureus* Beta Subunit Protein Stimulates *S. aureus* Pol III-L and *E. coli* Core The experiment of FIG. 5A, tests the ability of *S. aureus* beta to stimulate *S. aureus* Pol III-L on a linear polydA-oligodT template. Reactions are also performed with *E. coli* beta and Pol III core. The linear template was polydA of average length of 4500 nucleotides primed with a 30mer oligonucleotide of T residues. The first two lanes show the activity of Pol III-L either without (lane 1) or with *S. aureus* beta (lane 2). The result shows that the *S. aureus* beta stimulates Pol III-L approximately 5-6 fold. Lanes 5 and 6 show the corresponding experiment using *E. coli* core with (lane 6) or without (lane 5) *E. coli* beta. The core is stimulated over 10-fold by the beta subunit under the conditions used.

Although gram positive and gram negative cells diverged from one another long ago and components of one polymerase machinery would not be expected to be interchangable, it was decided to test the activity of the *S. aureus* beta with *E. coli* Pol III core. Lanes 3 and 4 shows that the *S. aureus* beta also stimulates *E. coli* core about 5-fold. This result can be explained by an interaction between the clamp and the polymerase that has been conserved during the evolutionary divergence of gram positive and gram negative cells. A chemical inhibitor that would disrupt this interaction would be predicted to have a broad spectrum of antibiotic activity, shutting down replication in gram negative and gram positive cells alike. This assay, and others based on this interaction, can be devised to screen chemicals for such inhibition. Further, since all the proteins in this assay are highly overexpressed through recombinant techniques, sufficient quantities of the protein reagents can be obtained for screening hundreds of thousands of compounds.

In summary, the results show that *S. aureus* beta, produced in *E. coli*, is indeed an active protein (i.e. it stimulates polymerase activity). Furthermore, the results shows that Pol III-L functions with a second protein (i.e. *S. aureus* beta). Before this experiment, there was no assurance that Pol III-L, which is significantly different in structure from *E. coli* alpha, would function with another protein. For example, unlike *E. coli* alpha, which copurifies with several accessory proteins, Pol III-L purified from *B. subtilis* purifies as a single protein with no other subunits attached (Barnes, et al., "Purification of DNA Polymerase III of Gram-positive Bacteria," *Methods in Enzy.* 262:35-42 (1995), which is hereby incorporated by reference). Finally, if one were to assume that *S. aureus* beta would function with a polymerase, the logical candidate would have been the product of the dnaE gene instead of PolC (Pol III-L) since the dnaE product is more homologous to *E. coli* alpha subunit than Pol III-L.

Example 10

The *S. aureus* Beta Subunit Behaves as a Circular Sliding Clamp

The ability of *S. aureus* beta to stimulate Pol III-L could be explained by formation of a 2-protein complex between Pol III-L and beta to form a processive replicase similar to the Type II class (e.g. T7 type). Alternatively, the *S. aureus* replicase is organized as the Type III replicase which operates with a circular sliding clamp and a clamp loader. In this case, the *S. aureus* beta would be a circular protein and would require a clamp loading apparatus to load it onto DNA. The ability of the beta subunit to stimulate Pol III-L in FIG. 5A could be explained by the fact that the polydA-oligodT template is a linear DNA and a circular protein could thread itself onto the DNA over an end. Such "end threading" has been observed with PCNA and explains its ability to stimulate DNA polymerase delta in the absence of the RFC clamp loader (Burgers, et al., "ATP-Independent Loading of the Proliferating Cell Nuclear Antigen Requires DNA Ends," *J. Biol. Chem.*, 268:19923-19926 (1993), which is hereby incorporated by reference).

To distinguish between these possibilities, *S. aureus* beta was examined for ability to stimulate Pol III-L on a circular primed template. In FIG. 5B, assays were performed using circular M13mp18 ssDNA coated with *E. coli* SSB and primed with a single oligonucleotide to test the activity of beta on circular DNA. Lane 1 shows the extent of DNA synthesis using Pol III-L alone. In lane 2, Pol III-L was supplemented with *S. aureus* beta. The *S. aureus* beta did not stimulate the activity of Pol III-L on this circular DNA (nor in the absence of SSB). Inability of *S. aureus* beta to stimulate Pol III-L is supported by the results of FIG. 6, lane 1 that analyzes the product of Pol III-L action on the circular DNA in an agarose gel in the presence of *S. aureus* beta. In summary, these results show that *S. aureus* beta only stimulates Pol III-L on linear DNA, not circular DNA. Hence, the *S. aureus* beta subunit behaves as a circular protein.

Lane 3 shows the result of adding both *S. aureus* beta and *E. coli* gamma complex to Pol III-L. Again, no stimulation was observed (compare with lane 1). This result indicates that the functional contacts between the clamp and clamp loader were not conserved during evolution of gram positive and gram negative cells.

Controls for these reactions on circular DNA are shown for the *E. coli* system in Lanes 4-6. Addition of only beta to *E. coli* Pol III core did not result in stimulating the polymerase (compare lanes 4 and 5). However, when gamma complex was included with beta and core, a large stimulation of synthesis was observed (lane 6). In summary, stimulation of synthesis is only observed when both beta and gamma complex were present, consistent with inability of the circular beta ring to assemble onto circular DNA by itself.

Example 11

Figure 6:
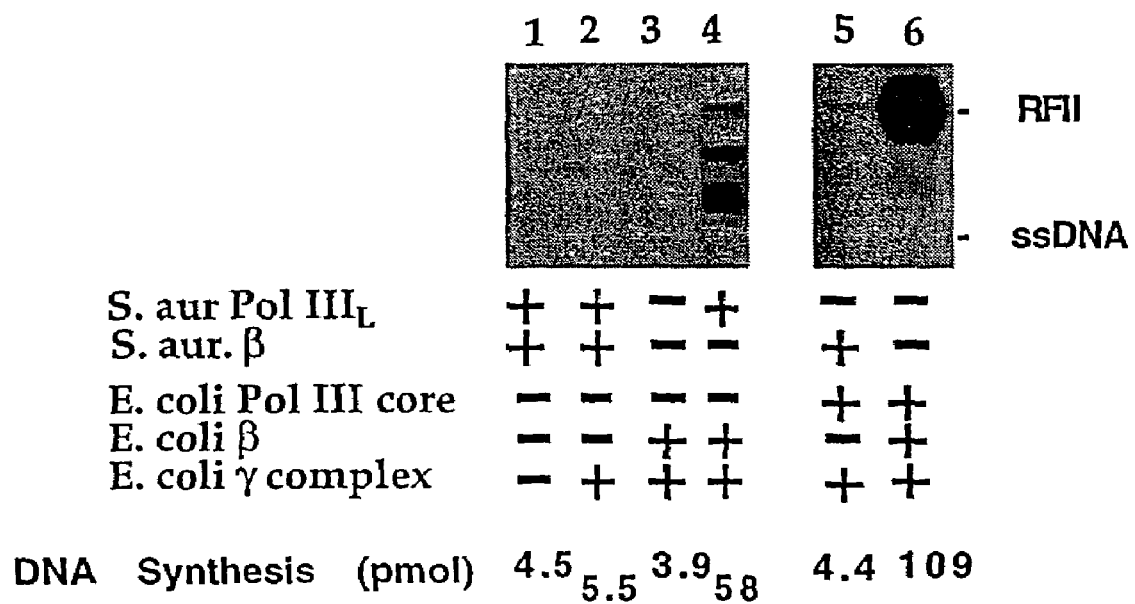
FIG. 6 shows that *S. aureus* Pol III-L functions with *E. coli* beta and gamma complex on circular primed DNA. It also shows that *S. aureus* beta does not convert Pol III-L with sufficient processivity to extend the primer all the way around a circular DNA. Replication reactions were performed on the circular singly primed M13mp18 ssDNA. Proteins added to the assay were as indicated in this figure. The amount of each protein, when present, was: *S. aureus* beta, 800 ng; *S. aureus* Pol III-L, 1500 ng (MonoQ fraction 64); *E. coli* Pol III core, 450 ng; *E. coli* beta, 100 ng; *E. coli* gamma complex, 1720 ng. Total DNA synthesis in each assay is indicated at the bottom of the figure.

Pol III-L Functions as a Pol III-Type Replicase with Beta and Gamma Complex to Become Processive Next, it was determined whether *S. aureus* Pol III-L requires two components (beta and gamma complex) to extend a primer full length around a circular primed template. In FIG. 6, a template circular M13mp18 ssDNA primed with a single DNA oligonucleotide was used. DNA products were analyzed in a neutral agarose gel which resolves starting materials (labeled ssDNA in FIG. 6) from completed duplex circles (labelled RFII for replicative form II). The first two lanes show, as demonstrated in other examples, that Pol III-L is incapable of extending the primer around the circular DNA in the presence of only *S. aureus* beta. In lane 4 of FIG. 6, *E. coli* gamma complex and beta subunit were mixed with *S. aureus* Pol III-L in the assay containing singly primed M13mp18 ssDNA coated with SSB. If the beta clamp, assembled on DNA by gamma complex, provides processivity to *S. aureus* Pol III-L, the ssDNA circle should be converted into a fully duplex circle (RFII) which would be visible in an agarose gel analysis. The results of the experiment showed that the *E. coli* beta and gamma complex did indeed provide Pol III-L with ability to fully extend the primer around the circular DNA to form the RFII (lane 4). The negative control using only *E. coli* gamma complex and beta is shown in lane 3. For comparison, lane 6 shows the result of mixing the three components of the *E. coli* system (Pol III core, beta and gamma complex). This reaction gives almost exclusively full length RFII product. The qualitatively different product profile that Pol III-L gives in the agarose gel analysis compared to *E. coli* Pol III core with beta and gamma complex shows that the products observed using Pol III-L is not due to a contaminant of *E. coli* Pol III core in the *S. aureus* Pol III-L preparation (compare lanes 4 and 6).

It is generally thought that the polymerase of one system is specific for its SSB. However, these reactions are performed on ssDNA coated with the *E. coli* SSB protein. Hence, the *S. aureus* Pol III-L appears capable of utilizing *E. coli* SSB and the *E. coli* beta. It would appear that the only component that is not interchangeable between the gram positive and gram negative systems is the gamma complex.

Thus, the *S. aureus* Pol III-L functions as a Pol III type replicase with the *E. coli* beta clamp assembled onto DNA by gamma complex.

Example 12

Purification of Two DNA Polymerase III-Type Enzymes From *S. aureus* Cells

The MonoQ resin by Pharmacia has very high resolution which would resolve the three DNA polymerases of *S. aureus*. Hence, *S. aureus* cells were lysed, DNA was removed from the lysate, and the clarified lysate was applied onto a MonoQ column. The details of this procedure are: 300 L of *S. aureus* (strain 4220 (a gift of Dr. Pat Schlievert, University of Minnisota)) was grown in 2×LB media at 37° C. to an OD of approximately 1.5 and then were collected by centrifugation. Approximately 2 kg of wet cell paste was obtained and stored at −70° C. 122 g of cell paste was thawed and resuspended in 192 ml of cell lysis buffer followed by passage through a French Press cell (Aminco) at 40,000 psi. The resultant lysate was clarified by high speed centrifugation (1.3 g protein in 120 ml). A 20 ml aliquot of the supernatant was dialyzed 2 h against 2 L of buffer A containing 50 mM NaCl. The dialyzed material (148 mg, conductivity=101 mM NaCl) was diluted 2-fold with Buffer A containing 50 mM NaCl and then loaded onto an 8 ml MonoQ column equilibrated in Buffer A containing 50 mM NaCl. The column was washed with Buffer A containing 50 mM NaCl, and then eluted with a 160 ml linear gradient of 0.05 M NaCl to 0.5 M NaCl in Buffer A. Fractions of 2.5 ml (64 total) were collected, followed by analysis in an SDS polyacrylamide gel and for their replication activity in assays using calf thymus DNA.

Figure 7:
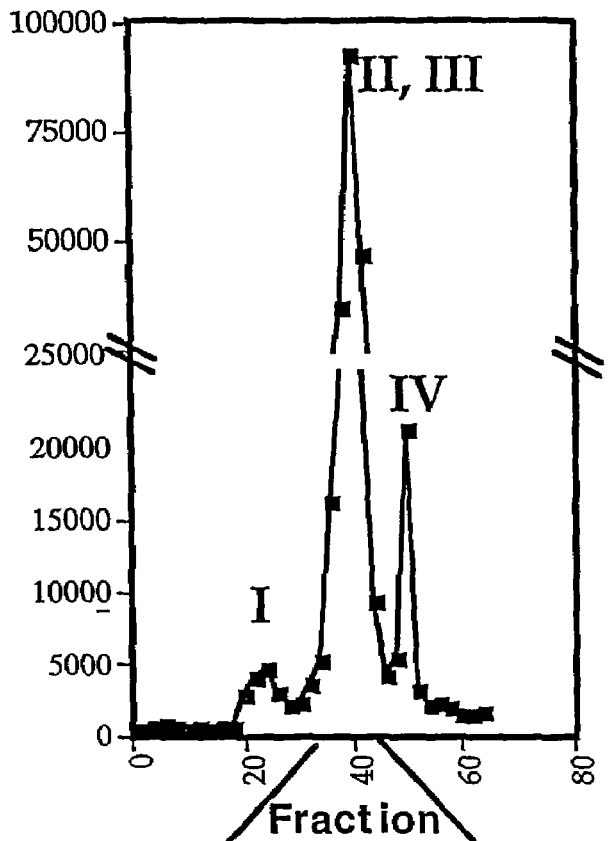
FIGS. 7A-B show that *S. aureus* contains four distinct DNA polymerases. Four different DNA polymerases were partially purified from *S. aureus* cells. *S. aureus* cell lysate was separated from DNA and, then, chromatographed on a MonoQ column. Fractions were analyzed for DNA polymerase activity. Three peaks of activity were observed. The second peak was the largest and was expected to be a mixture of two DNA polymerases based on early studies in *B. subtilis*. Chromatography of the second peak on phosphocellulose (FIG. 7B) resolved two DNA polymerases from one another.
Figure 7:
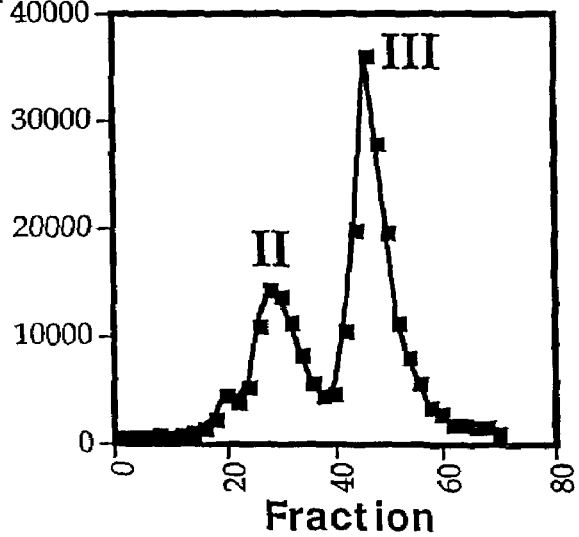

Three peaks of DNA polymerase activity were identified (FIG. 7). Previous studies of cell extracts prepared from the gram positive organism, *Bacillus subtilis*, identified only two peaks of activity off a DEAE column (similar charged resin to MonoQ). The first peak was Pol II, and the second peak was a combination of DNA polymerases I and III. The DNA polymerases I and III were then separated on a subsequent phosphocellulose column. The middle peak in FIG. 7 is much larger than the other two peaks, and, thus, it was decided to chromatograph this peak on a phosphocellulose column. The second peak of DNA synthetic activity was pooled (fractions 37-43; 28 mg in 14 ml) and dialyzed against 1.5 L P-cell buffer for 2.5 h. Then, the sample (ionic strength equal to 99 mM NaCl) was applied to a 5 ml phosphocellulose column equilibrated in P-cell buffer. After washing the column in 10 ml P-cell buffer, the column was eluted with a 60 ml gradient of 0-0.5 M NaCl in P-cell buffer. 70 fractions were collected. Fractions were analyzed for DNA synthesis using calf thymus DNA as template.

This column resolved the polymerase activity into two distinct peaks (FIG. 7B). Hence, there appear to be four DNA polymerases in *Staphylococcus aureus*, which was designated here as peaks 1 (first peak off MonoQ), peak 2 (first peak off phosphocellulose), peak 3 (second peak of phosphocellulose), and peak 4 (last peak off Mono Q) (see FIG. 7). Peak 4 was presumably Pol III-L, as it elutes from MonoQ in a similar position as the Pol III-L expressed in *E. coli* (compare FIG. 7A with FIG. 2).

Figure 8:
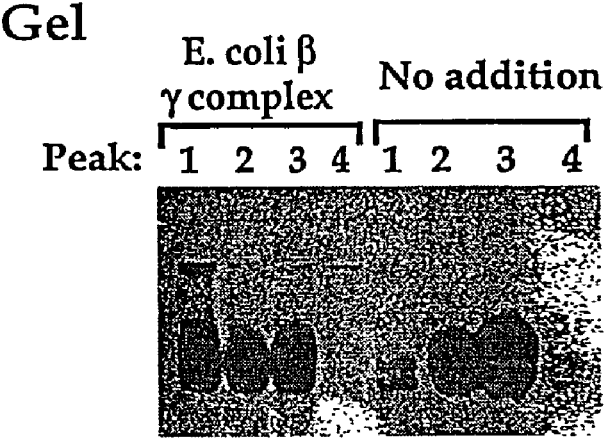
FIGS. 8A-B show that *S. aureus* has two DNA Pol III's. The four DNA polymerases partially purified from *S. aureus* extract, designated peaks I-IV in FIG. 7, were assayed on circular singly primed M13mp18 ssDNA coated with *E. coli* SSB either in the presence or absence of *E. coli* beta (50 ng) and gamma complex (50 ng). Each reaction contained 2 µl of the partially pure polymerase (Peak 1 was Mono Q fraction 24 (1.4 ug), Peak 2 was phosphocellulose fraction 26 (0.016 mg/ml), Peak 3 was phosphocellulose fraction 46 (0.18 mg/ml), and Peak 4 was MonoQ fraction 50 (1 ug).

To test which peak contained a Pol III-type of polymerase, an assay was used in which the *E. coli* gamma complex and beta support formation of full length RFII product starting from *E. coli* SSB coated circular M13mp18 ssDNA primed with a single oligonucleotide. In FIG. 8, both Peaks 1 and 2 are stimulated by the *E. coli* gamma complex and beta subunit, and, in fact, Peaks 2 and 3 are inhibited by these proteins (the quantitation is shown below the gel in the figure). Further, the product analysis in the agarose gel shows full length RFII duplex DNA circles only for peaks 1 and 4. These results, combined with the NEM, pCMB and KCl characteristics in Table 1 below, suggests that there are two Pol III-type DNA polymerases in *S. aureus*, and that these are partially purified in peaks 1 and 4.

Next, it was determined which of these peaks of DNA polymerase activity correspond to DNA polymerases I, II, and III, and which peak is the unidentified DNA polymerase. In the gram postive bacterium *B. subtilis*, Pol III is inhibited by pCMB, NEM, and 0.15 M NaCl, Pol II is inhibited by KCl, but not NEM or 0.15 M KCL, and Pol I is not inhibited by any of these treatments (Gass, et al., "Further Genetic and Enzymological Characterization of the Three *Bacillus subtilis* Deoxyribonucleic Acid Polymerases," *J. Biol. Chem.*, 248: 7688-7700 (1973), which is hereby incorporated by reference). Hence, assays were performed in the presence or absence of pCMB, NEM, and 0.15 M KCl (see Table 1 below). Peak 3 clearly corresponded to Pol I, because it was not inhibited by NEM, pCMB, or 0.15 M NaCl. Peak 2 correspond to Pol II, because it was not inhibited by NEM, but was inhibited by pCMB and 0.15 M NaCl. Peaks 1 and 4 both had characteristics that mimic Pol III; however, peak 4 elutes on MonoQ at a similar position as Pol III-L expressed in *E. coli* (see FIG. 2B). Hence, peak 4 is likely Pol III-L, and peak 1 is likely the unknown polymerase.

TABLE 1

| Expected Characteristics Polymerase | pCMB | NEM | 0.15M KCl |
|---|---|---|---|
| Pol I | not inhibited* | not inhibited | not inhibited |
| Pol II | inhibited** | not inhibited | not inhibited |
| Pol III-L | inhibited | inhibited | not inhibited |
| Observed Characteristics Peak | PCMB | NEM | 0.15M KCL assignment |
| peak 1 | inhibited | inhibited | new polymerase |
| Peak 2 | inhibited | not inhibited | Pol II |
| Peak 3 | not inhibited | not inhibited | Pol I |
| Peak 4 | inhibited | inhibited | Pol III-L |

*Not inhibited is defined as greater than 75% remaining activity
**Inhibited is defined as less than 40% remaining activity Example 13

Demonstration That Peak 1 (Pol 111-2) Functions as a Pol III-Type Replicase With *E. coli* Beta Assembled on DNA by *E. coli* Gamma Complex It is interesting to note that the characteristics of peak 1 are similar to those of a Pol III-type of DNA polymerase. To test whether peak 1 contained a Pol III type of polymerase, an assay in which the *E. Coli* gamma complex and beta support formation of full length RFII product starting from *E. coli* SSB coated circular M13mp18 ssDNA primed with a single oligonucleotide was carried out. In FIG. 8, both Peaks 1 and 2 are stimulated by the *E. coli* gamma complex and beta subunit, and, in fact, Peaks 2 and 3 are inhibited by these proteins (the quantitation is shown below the gel in the FIG. 8). Further, the product analysis in the agarose gel shows full length RFII duplex DNA circles only for peaks 1 and 4. These results, combined with the NEM, pCMB, and KCl characteristics in the Table above, suggests that there are two Pol III-type DNA polymerases in *S. aureus*, and that these are partially purified in peaks 1 and 4.

Example 14

Identification and Cloning of *S. aureus* dnaE

This invention describes the finding of two DNA polymerases that function with a sliding clamp assembled onto DNA by a clamp loader. One of these DNA polymerases is likely Pol III-L, but the other has not been identified previously. Presumably the chromatographic resins used in earlier studies did not have the resolving power to separate the enzyme from other polymerases. This would be compounded by the low activity of Pol III-2. To identify a gene encoding a second Pol III, the amino acid sequences of the Pol III alpha subunit of *Escherichia coli*, *Salmonella typhimurium*, *Vibrio cholerae*, *Haemophilis influenzae*, and *Helicobacter pylori* were aligned using Clustal W (1.5). Two regions about 400 residues apart were conserved and primers were designed for the following amino acid sequences: upstream, LLFERFLNPERVSMP (SEQ. ID. No. 21) (corresponds in *E. coli* to residues 385-399); downstream KFAGYGFNKSHSAAY (SEQ. ID. No. 22) (corresponds in *E. coli* to residues 750-764). The following primers were designed to these two peptide regions using codon preferences for *S. aureus*: upstream, 5'CTTCTTTTTGAAAGATTTCTAAATAAA-GAACGTTATTCAATGCC 3' (SEQ. ID. No. 23); downstream, 5' ATAAGCTGCAGCATGACTTTTAT-TAAAACCATAACCTGCAAATTT 3' (SEQ. ID. No. 24). Amplification was performed using 2.5 units of Taq DNA Polymerase (Gibco, BRL), 100 ng *S. aureus* genomic DNA, 1 mM of each of the four dNTPs, 1 µM of each primer, and 3 mM $MgCl_2$ in 100 µl of Taq buffer. Thirty-five cycles of the following scheme were repeated: 94° C., 1 min; 55° C., 1 min; 72° C., 90 sec. The PCR product (approximately 1.1 kb) was electrophoresed in a 0.8% agarose gel, and purified using a Geneclean III kit (Bio 101). The product was then divided equally into ten separate aliquots, and used as a template for PCR reactions, according to the above protocol, to reamplify the fragment for sequencing. The final PCR product was purified using a Quiagen Quiaquick PCR Purification kit, quantitated via optical density at 260 nM, and sequenced by the Protein/DNA Technology Center at Rockefeller University. The same primers used for PCR were used to prime the sequencing reactions.

Next, additional PCR primers were designed to obtain more sequence information 3' to the amplified section of the sequence of dnaE. The upstream primer was: 5' AGT-TAAAAATGCCATATTTTGACGTGTTTTAGTTCTAAT 3' (SEQ. ID. No. 25), and the downstream primer was, 5' CTTG-CAAAAGCGGTTGCTAAAGATGTTGGAC-GAATTATGGGG 3' (SEQ. ID. No. 26).

These primers were used in a PCR reaction using 2.5 units of Taq DNA Polymerase (Gibco, BRL) with 100 ng. *S. aureus* genomic DNA as a template, 1 mM dNTP's, 1□M of each prmer, 3 mM $MgCl_2$ in 100 l of Taq buffer. Thirty-five cycles of the following scheme were repeated: 94° C., 1 min; 55° C., 1 min; 72° C., 2 min 30 seconds. The 1.6 Kb product was then divided into 5 aliquots, and used as a template in a set of 5 PCR reactions, as described above, to amplify the product for sequencing. The products of these reactions were purified using a Qiagen Qiaquick PCR Purification kit, quantitated via optical density at 260 nm, and sequenced by the Protein/DNA Technology Center at Rockefeller University. The sequence of this product yielded about 740 bp of new sequence 3' of the first sequence. As this gene shows better homology to gram negative pol III subunit compared to gram positive Pol III-L, it will be designated the dnaE gene.

As this gene shows better homology to the gram negative Pol III α subunit compared to gram positive Pol III-L, it will be designated the dnaE gene.

Example 15

Identification and Cloning of *S. aureus* dnaX

The fact that the *S. aureus* beta stimulates Pol III-L and has a ring shape suggests that the gram postive replication machinery is of the three component type. This implies the presence of a clamp loader complex. This is not a simple determination to make as the *B. subtilis* genome shows homologs to only two of the five subunits of the *E. coli* clamp loader (dnaX encoding gamma, and holB encoding delta prime). On the basis of the experiments in this application, which suggests that there is a clamp loader, we now presume these two subunit homologues are part of the clamp loader for the *S. aureus* beta.

As a start in obtaining the clamp loading apparatus, a strategy was devised to obtain the gene encoding the tau/gamma subunit of *S. aureus*. In *E. coli*, these two subunits are derived from the same gene. Tau is the full length product, and gamma is about ⅔ the length of tau. Gamma is derived from the dnaX gene by an efficient translational frameshift mechanism that after it occurs incorporates only one unique C-terminal reside before encountering a stop codon. To identify the dnaX gene of *S. aureus* by PCR analysis, the dnaX genes of *B. subtilis*, *E. coli*, and *H. influenzae* were aligned. Upon comparison of the amino acid sequence encoded by these dnaX genes, two areas of high homology were used to predict the amino acid sequence of the *S. aureus* dnaX gene product. PCR primers were designed to these sequences, and a PCR product of the expected size was indeed produced. DNA primers were designed to two regions of high similarity for use in PCR that were about 100 residues apart. The amino acid sequences of these regions were: upstream, HAYLFSG-PRG (SEQ. ID. No. 27) (corresponds to residues 39-48 of *E. coli*), and downstream, ALLKTLEEPPE (SEQ. ID. No. 28) (corresponds to residues 138-148 of *E. coli*). The DNA sequence of the PCR primers was based upon the codon usage of *S. aureus*. The upstream 38mer was 5'-CGC GGATCCCATGCATATTTATTTTCAGGTCCAAGAGG-3' (SEQ. ID. No. 29). The first 9 nucleotides contain a BamHI site and do not correspond to amino acid codons; the 3' 29 nucleotides correspond to the amino acids: HAYLFSGPRG (SEQ. ID. No.30). The downstream 39 mer was 5'-CCG GAATTCTGGTGGTTCTTCTAATGTTTTTAATAATGC-3' (SEQ. ID. No. 31). The EcoRI site is underlined and the 3' 33 nucleotides correspond to the amino acid sequence: ALLK-TLEEPPE (SEQ. ID. No. 32). The expected PCR product, based on the alignment, is approximately 268 bp between the primer sequences. Amplification was performed using 500 ng genomic DNA, 0.5 mM dNTPs, 1 µM of each primer, 1 mM $MgSO_4$, 2 units vent DNA polymerase in 100 µl of vent buffer. Forty cycles were performed using the following cycling scheme: 94° C., 1 min; 60° C., 1 min.; 72° C., 30s. The approximately 300 bp product was digested with EcoRI and BamHI and purified in a 0.7% agarose gel. The pure digested fragment was ligated into pUC18 which had been digested with EcoRI and BamHI and gel purified in a 0.7% agarose gel. Ligated products were transformed into *E. coli* competent DH5a cells (Stratagene), and colonies were screened for the correct chimera by examining minipreps for proper length and correct digestion products using EcoRI and BamHI. The sequence of the insert was determined and was found to have high homology to the dnaX genes of several bacteria. This sequence was used to design circular PCR primers. Two new primers were designed for circular PCR based on this sequence.

A circular PCR product of approximately 1.6 kb was obtained from a HincII digest of chromosomal DNA that was recircularized with ligase. This first circular PCR yielded most of the remaining dnaX gene. The rightward directed primer was 5'-TTT GTA AAG GCA TTA CGC AGG GGA CTA ATT CAG ATG TG-3' (SEQ. ID. No. 33); the sequence of the leftward primer was 5'-TAT GAC ATT CAT TAC AAG GTT CTC CAT CAG TGC-3' (SEQ. ID. No. 34). Genomic DNA (3 µg) was digested with HincII, purified with phenol/chloroform extraction, ethanol precipitated and redissolved in 70 µl T.E. buffer. The genomic DNA was recircularized upon adding 4000 units T4 ligase (New England Biolabs) in a final volume of 100 µl T4 ligase buffer (New England Biolabs) at 16° C. overnight. The PCR reaction consisted of 90 ng recircularized genomic DNA, 0.5 mM each dNTP, 100 pmol of each primer, 1.4 mM magnesium sulfate, and 1 unit of elongase (GIBCO) in a final volume of 100 µl elongase buffer (GIBCO). 40 cycles were performed using the following scheme: 94° C., 1 min., 55° C., 1 min., and 68° C., 2 min. The resulting PCR product was approximately 1.6 kb. The PCR product was purified from a 0.7% agarose gel and sequenced directly. A stretch of approximately 750 nucleotides was obtained using the rightward primer used in the circular PCR reaction. To obtain the rest of the sequence, other sequencing primers were designed in succession based on the information of each new sequencing run.

This sequence, when spliced together with the previous 300 bp PCR sequence, contained the complete N-terminus of the gene product (stop codons are present upstream) and possibly lacked only about 50 residues of the C-terminus. The amino terminal region of *E. coli* gamma/tau shares appears the most conserved region of the gene as this area shares homology with RFC subunit of the human clamp loader and with the gene 44 protein of the phage T4 clamp loader. An alignment of the N-terminal region of the *S. aureus* gamma/tau protein with that of *B. subtilis* and *E. coli* is shown in FIG. 10. Among the highly conserved residues are the ATP binding site consensus sequence and the four cystine residues that form a Zn++ finger.

After obtaining 1 kb of sequence in the 5' region of dnaX, it was sought to determine the remaining 3' end of the gene. Circular PCR products of approximately 800bps, 600bps, and 1600bps were obtained from Apo I, or Nsi I or Ssp I digest of chromosomal DNA that were recircularized with ligase. The rightward directed primer was 5'-GAGCACTGATGAACT-TAGAATTAGATATG-3'(SEQ. ID. No. 35); the sequence of the leftward primer was 5'-GATACTCAGTATCTTTCTCA-GATGTTTTATTC-3'(SEQ. ID. No. 36). Genomic DNA (3 g) was digested with, Apo I, or Nsi I or Ssp I, purified with phenol/chloroform extraction, ethanol precipitated, and redissolved in 70 I T.E. buffer. The genomic DNA was recircularized upon adding 4000 units of T4 ligase (New England Biolabs) in a final volume of 100 1 T4 ligase buffer (New England Biolabs) at 16° C. overnight. The PCR reaction consisted of 90 ng recircularized genomic DNA, 0.5 mM each dNTP, 100 pmol of each primer, 1.4 mM magnesium sulfate, and 1 unit of elongase (GIBCO) in a final volume of 100 1 elongase buffer (GIBCO). 40 cycles were performed using the following scheme: 94° C., 1 mm.; 55° C., 1 mm.; 68° C., 2 mm. The PCR products were directly cloned into pCR II TOPO vector using the TOPO TA cloning kit (Invitrogen Corporation) for obtaining the rest of the C terminal sequence of *S. aureus* dnaX. DNA sequencing was performed by the Rockefeller University sequencing facility.

Example 16

Identification and Cloning of *S. aureus* dnaB

In *E. coli*, the DnaB helicase assembles with the DNA polymerase III holoenzyme to form a replisome assembly. The DnaB helicase also interacts directly with the primase to complete the machinery needed to duplicate a double helix. As a first step in studying how the *S. aureus* helicase acts with the replicase and primase, *S. aureus* was examined for presence of a dnaB gene.

The amino acid sequences of the DnaB helicase of *Escherichia coli*, *Salmonella typhimurium*, *Haemophilis influenzae*, and *Helicobacter pylori* were aligned using Clustal W (1.5). Two regions about 200 residues apart showed good homology. These peptide sequences were: upstream, DLIVAARPSMGKT (SEQ. ID. No. 37) (corresponds to residues 225-238 of *E. coli* DnaB), and downstream, EIIIGKQRNGPIGTV (SEQ. ID. No. 38) (corresponds to residues 435-449 of *E. coli*). The following primers were designed from regions which contained conserved sequences using codon preferences for *S. aureus*: The upstream primer was 5' GACCT-TATAATTGTAGCTGCACGTCC TTCTAT GGGAAAAAC 3' (SEQ. ID. No. 39); the dowstream primer was 5' AACAT-TATTAAGTCAGCATCTTGT TCTATTGATCCAGAT-TCAACGAAG 3' (SEQ. ID. No. 40). A PCR reaction was carried out using 2.5 units of Taq DNA Polymerase (Gibco, BRL) with 100 ng. *S. aureus* genomic DNA as template, 1 mM dNTP's, 1 µM of each primer, 3 mM MgCl$_2$ in 100 µl of Taq buffer. Thirty-five cycles of the following scheme were repeated: 94° C., 1 min.; 55° C., 1 min.; and 72° C., 1 min. Two PCR products were produced, one was about 1.1 kb, and another was 0.6 kb. The smaller one was the size expected. The 0.6 kb product was gel purified and used as a template for a second round of PCR as follows. The 0.6 kb PCR product was purified from a 0.8% agarose gel using a Geneclean III kit (Bio 101) and then divided equally into five separate aliquots, as a template for PCR reactions. The final PCR product was purified using a Quiagen Quiaquick PCR Purification kit, quantitated via optical density at 260 nM, and sequenced by the Protein/DNA Technology Center at Rockefeller University. The same primers used for PCR were used to prime the sequencing reaction. The amino acid sequence was determined by translation of the DNA sequence in all three reading frames, and selecting the longest open reading frame. The PCR product contained an open reading frame over its entire length. The predicted amino acid sequence shares homology to the amino acid sequences encoded by dnaB gene of other organisms.

Additional sequence information was determined using the circular PCR technique. Briefly, *S. aureus* genomic DNA was digested with various endonucleases, then religated with T4 DNA ligase to form circular templates. To perform PCR, two primers were designed from the initial sequence. The first primer, 5' GATTTGTAGTTCTGGTAATGTTGACT-CAAACCGCTTAAGAACCGG 3' (SEQ ID. No. 41), matches the coding strand; the second primer, 5' ATACGT-GTGGTTAACTGATCAGCAAC-CCATCTCTAGTGAGAAAATACC 3' (SEQ ID. No. 42), matches the sequence of the complementary strand. These two primers are directed outwards from a central point, and allow determination of new sequence information up to the ligated endonuclease site. A PCR product of approximately 900 bases in length was produced using the above primers and template derived from the ligation of *S. aureus* genomic DNA which had been cut with the restriction endonuclease Apo I. This PCR product was electrophoresed in a 0.8% agarose gel, eluted with a Qiagen gel elution kit, divided into five separate aliquots, and used as a template for reamplification by PCR using the same primers as described above. The final product was electrophoresed in an 0.8% agarose gel, visualized via staining with ethidium bromide under ultraviolet light, and excised from the gel. The excised gel slice was frozen, and centrifuged at 12,000 rpm for 15 minutes. The supernatant was extracted with phenol/chloroform to remove ethidium bromide, and was then cleaned using a Qiagen PCR purification kit. The material was then quantitated from its optical density at 260 nm and sequenced by the Protein/DNA Technology Center at the Rockefeller University.

The nucleotide sequence contained an open reading frame over its length, up to a sequence which corresponded to the consensus sequence of a cleavage site of the enzyme Apo I.

Following this point, a second open reading frame encoded a different reading frame up to the end of the product. The inital sequence information was found to match the inital sequence and to extend it yet further towards the C-terminus of the protein. The second reading frame was found to end in a sequence which matched the 5'-terminus of the previously determined sequence and, thus, represents an extension of the sequence towards the N-terminus of the protein.

Additional sequence information was obtained using the above primers and a template generated using *S. aureus* genomic DNA circularized via ligation with T4 ligase following digestion with Cla I. The PCR product was generated using 35 cycles of the following program: denaturation at 94° C. for 1 min.; annealing at 55° C. for 1 min.; and extension at 68° C. for 3 minutes and 30 s. The PCR products were electrophoresed in a 0.8% agarose gel, eluted with a Qiagen gel elution kit, divided into five separate aliquots, and used as a template reamplification via PCR with the same primers described above. The final product was electrophoresed in an 0.8% agarose gel, visualized via staining with ethidium bromide under ultraviolet light, and excised from the gel. The excised gel slice was frozen, and centrifuged at 12,000 rpm for 15 min. The supernatant was cleaned using a Qiagen PCR purification kit. The material was then quantitated via optical density at 260 nm and sequenced by the Protein/DNA Technology Center at Rockefeller University. The open reading frames continued past 500 bases. Therefore, the following additional sequencing primers were designed from the sequence to obtain further information:

```
                                                (SEQ. ID No. 43)
    5' CGTTTTAATGCATGCTTAGAAACGATATCAG 3' and, (SEQ. ID No. 44)
    5' CATTGCTAAGCAACGTTACGGTCCAACAGGC 3'.
```

The N-terminal and C-terminal nucleotide sequence extensions generated using this circular PCR product completed the 5' region of the gene (encoding the N-terminus of DnaB); however, a stop codon was not reached in the 3' region and, thus, a small amount of sequence is still needed to complete this gene.

The alignment of the *S. aureus* dnaB with *E. coli* dnaB and the dnaB genes of *B. subtilis* and *S. typhimurium* is shown in FIG. 11.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated *Staphylococcus* polypeptide consisting of the amino acid sequence according to SEQ ID NO: 4.

* * * * *

UNITED STATES PATENT AND TRADEMARK OFFICE
CERTIFICATE OF CORRECTION

| | | |
|---|---|---|
| PATENT NO. | : 7,557,184 B2 | Page 1 of 1 |
| APPLICATION NO. | : 10/282287 | |
| DATED | : July 7, 2009 | |
| INVENTOR(S) | : O'Donnell et al. | |

It is certified that error appears in the above-identified patent and that said Letters Patent is hereby corrected as shown below:

Col. 1 at lines 9-12, delete "The present invention was made with funding from National Institutes of Health Grant No. GM38839. The United States Government may have certain rights in this invention." And insert -- This invention was made with government support under grant GM38839 awarded by National Institutes of Health. The government has certain rights in the invention -- in its place.

Signed and Sealed this
Fifteenth Day of March, 2011

David J. Kappos
*Director of the United States Patent and Trademark Office*